United States Patent
Ambrisco et al.

(12) 
(10) Patent No.: US 6,319,268 B1
(45) Date of Patent: *Nov. 20, 2001

(54) ADJUSTABLE BLOOD FILTRATION SYSTEM

(75) Inventors: William M. Ambrisco; Richard O. Murphy, both of Mountain View; Timothy J. Wood, Campbell; Roman Turovskiy, San Francisco; Tracy D. Maahs, Santa Clara; Bruce S. Addis, Redwood City, all of CA (US)

(73) Assignee: Embol-X, Inc., Mountain View, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/630,805

(22) Filed: Aug. 2, 2000

Related U.S. Application Data

(63) Continuation of application No. 09/392,059, filed on Sep. 8, 1999, now Pat. No. 6,152,947, which is a continuation of application No. 09/070,660, filed on Apr. 29, 1998, now Pat. No. 6,007,557.

(51) Int. Cl.$^7$ .................................................. A61B 17/00
(52) U.S. Cl. ............................................................ 606/200
(58) Field of Search ................................... 606/200, 159, 606/198, 194, 108; 128/898; 604/104, 284, 96, 101

(56) References Cited

U.S. PATENT DOCUMENTS

| | | |
|---|---|---|
| 4,665,906 | 5/1987 | Jervis . |
| 4,723,549 | 2/1988 | Wholey . |
| 4,873,978 | 10/1989 | Ginsburg . |
| 4,955,895 | 9/1990 | Sugiyama et al. ............... 606/194 |
| 5,053,008 | 10/1991 | Bajaj .................................. 604/104 |
| 5,330,451 | 7/1994 | Gabbay ............................. 604/284 |
| 5,370,685 | 12/1994 | Stevens ................................ 623/2 |

(List continued on next page.)

FOREIGN PATENT DOCUMENTS

| | | |
|---|---|---|
| PI 9301980 | 10/1993 | (BR) . |
| 3417738 A1 | 11/1985 | (DE) . |
| 079134A1 | 2/1997 | (EP) . |
| 2567405 | 7/1984 | (FR) . |
| WO97/17100 | 5/1997 | (WO) . |

OTHER PUBLICATIONS

Barbut et al., "Cerebral Emboli Detected During Bypass Surgery Are Associated With Clamp Removal," *Stroke*, 25(12):2398–2402 (1994).

(List continued on next page.)

*Primary Examiner*—Olik Chaudhuri
*Assistant Examiner*—(Vikki) Hoa B. Trinh
(74) *Attorney, Agent, or Firm*—Lyon & Lyon LLP

(57) ABSTRACT

A modular blood filter device and delivery system, comprising a hollow vessel insertion device with a modular filter apparatus. The insertion device, which can be an introducer, includes a distal end adapted to enter an artery, and a proximal end adapted to receive a modular filter apparatus. When the insertion device is a cannula, the modular filter apparatus is received through a side port. The modular filter apparatus includes a shaft and an adjustable filter device or a removable filter associated with the shaft. The adjustable filter includes filter mesh, an adjustable frame capable of assuming enlarged and contracted conditions and a frame sizing mechanism associated with the frame. The adjustable frame may be self-adjusting or externally adjusted to fit the vessel and to capture embolic material in the mesh. The frame may be collapsed to the contracted condition, and may be removed from the vessel or embolic debris may be removed by an aspiration tube. The modular filter cartridge may be removed from the cannula, and a new modular filter cartridge may then be received therein.

18 Claims, 47 Drawing Sheets

U.S. PATENT DOCUMENTS

| | | | |
|---|---|---|---|
| 5,695,519 | 12/1997 | Summers et al. | 606/200 |
| 5,846,260 * | 12/1998 | Maahs | 606/200 |
| 5,989,281 * | 11/1999 | Barbut et al. | 606/200 |
| 6,007,557 * | 12/1999 | Ambrisco et al. | 606/200 |
| 6,142,987 * | 11/2000 | Tsugita et al. | 606/194 X |
| 6,152,947 * | 11/2000 | Ambrisco et al. | 606/200 |
| 6,165,200 * | 12/2000 | Tsugita et al. | 606/200 |

OTHER PUBLICATIONS

Barbut et al., "Comparison of Transcranial Doppler Ultrasonography and Transesophageal Echocardiography to Monitor Emboli During Coronary Artery Bypass Surgery," *Stroke* 27(1):87–90 (1996).

Barbut et al., "Aortic Atheromatosis and Risks of Cerebral Embolization," *Journal of Cardiothoracic and Vascular Anesthesia* 10(1):24–30 (1996).

van der Linden et al., "When Do Cerebral Emboli Appear During Open Heart Operations? A Transcrainial Doppler Study," *Ann. Thorac. Surg. 51*:237–241 (1991).

* cited by examiner

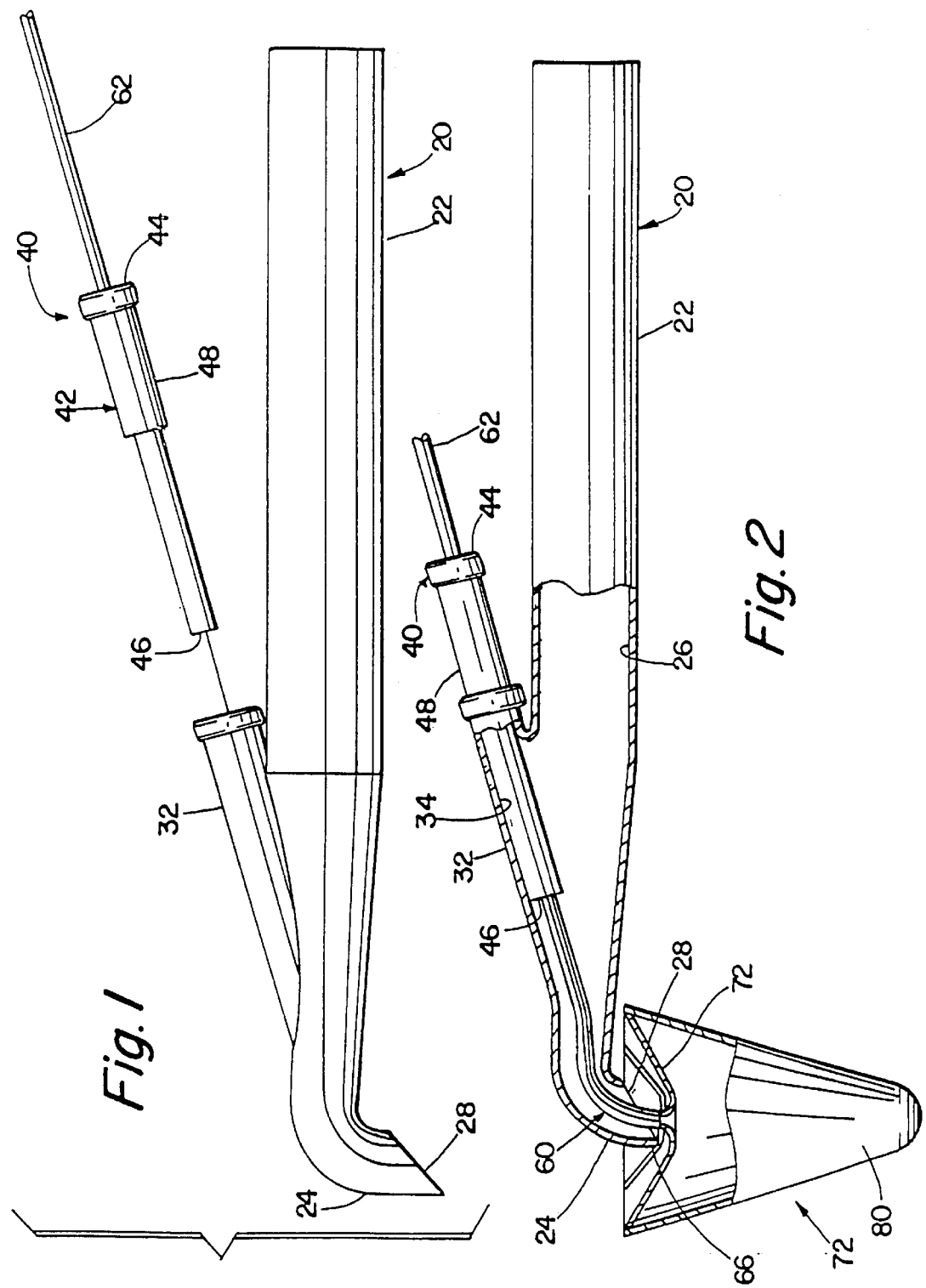

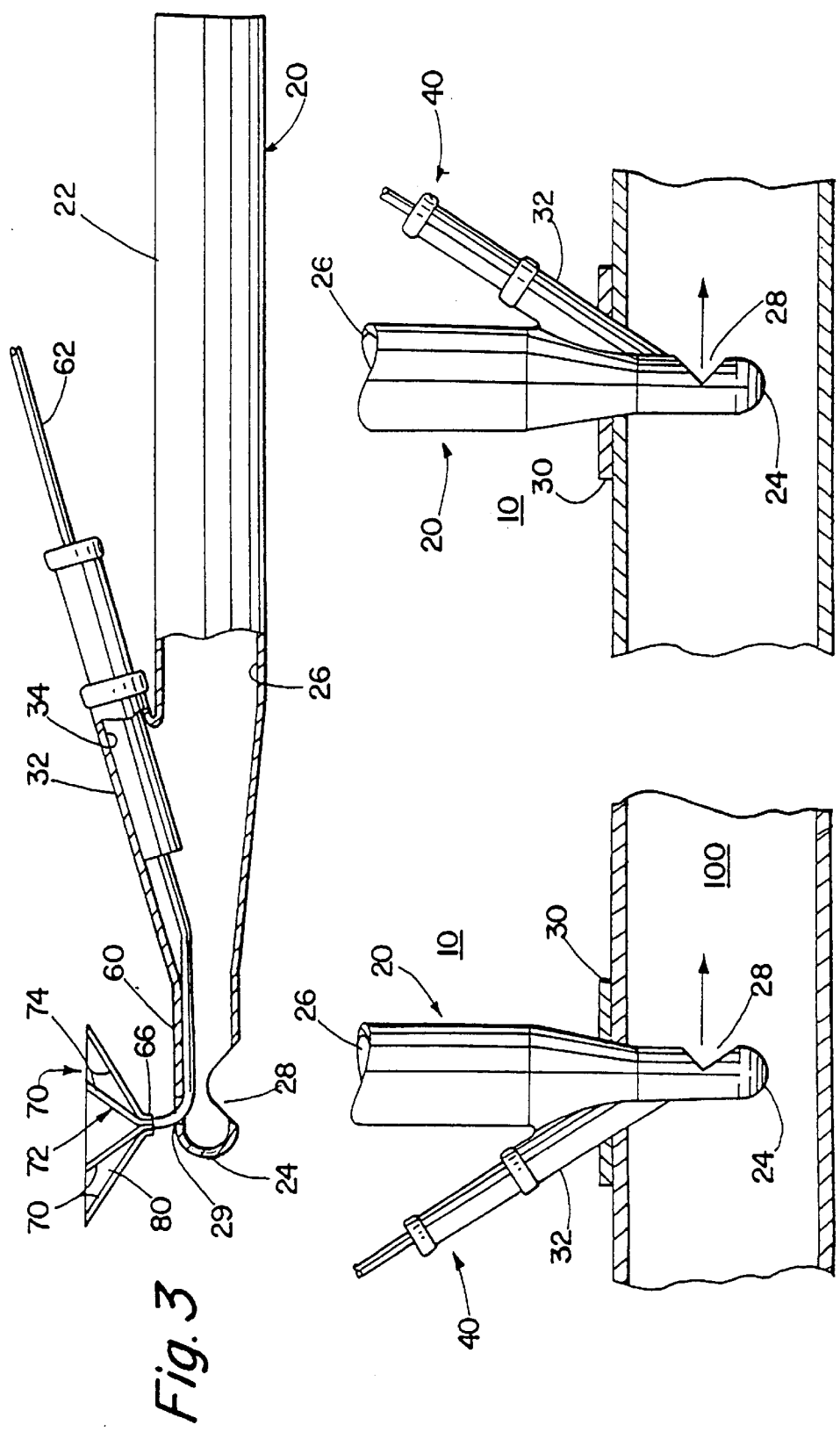

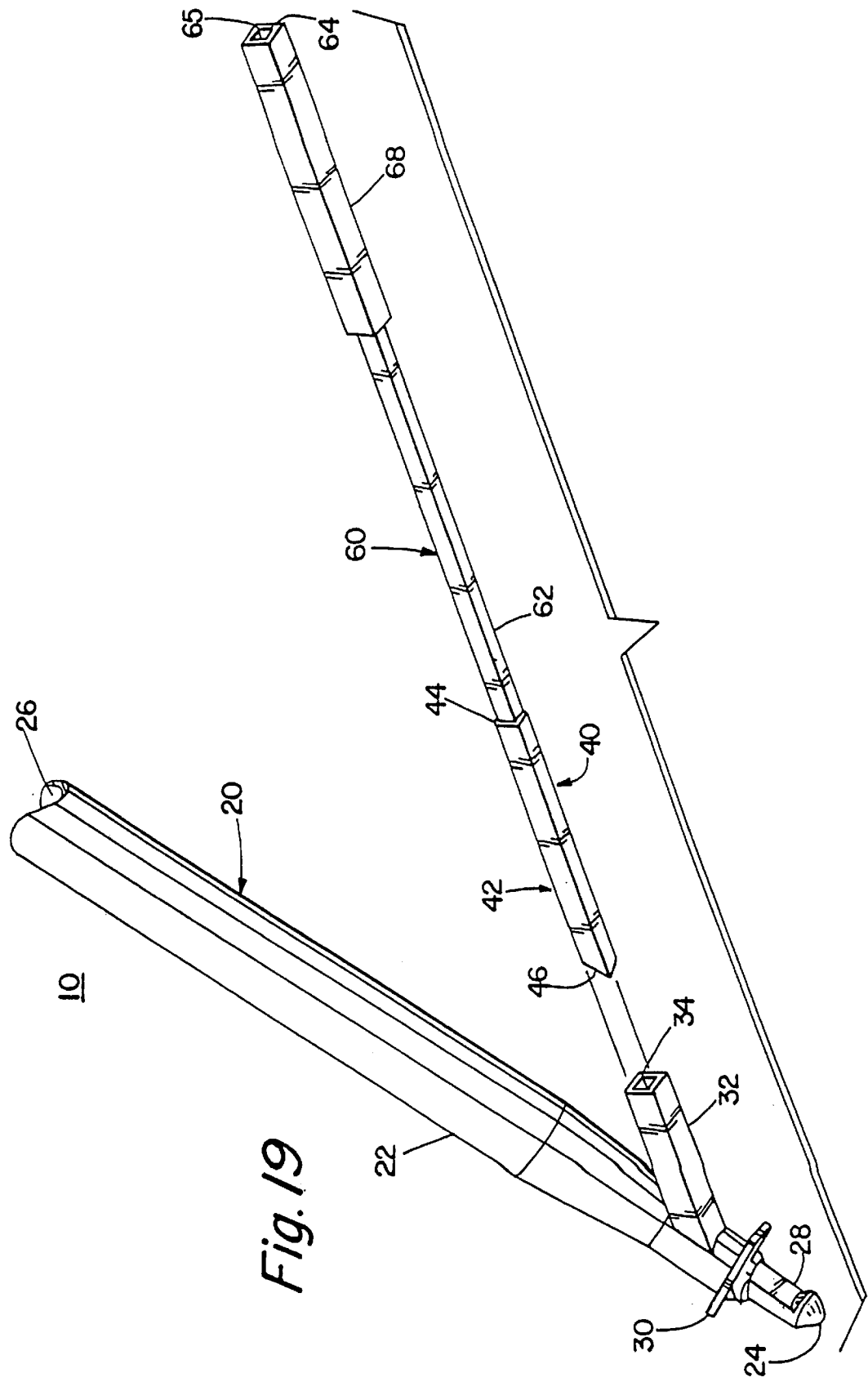

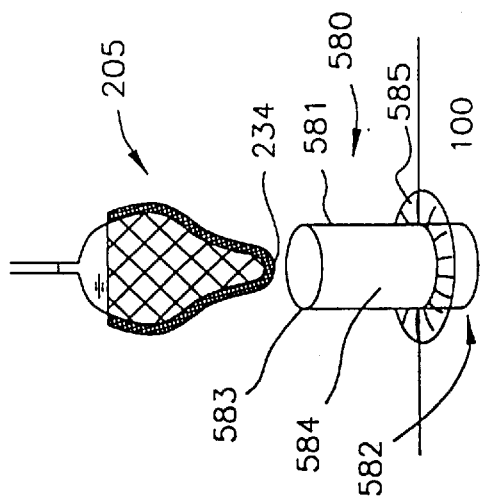
FIG. 20B
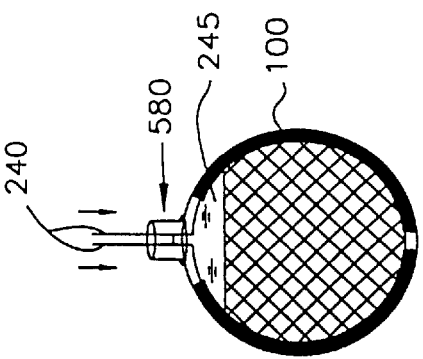
FIG. 20C
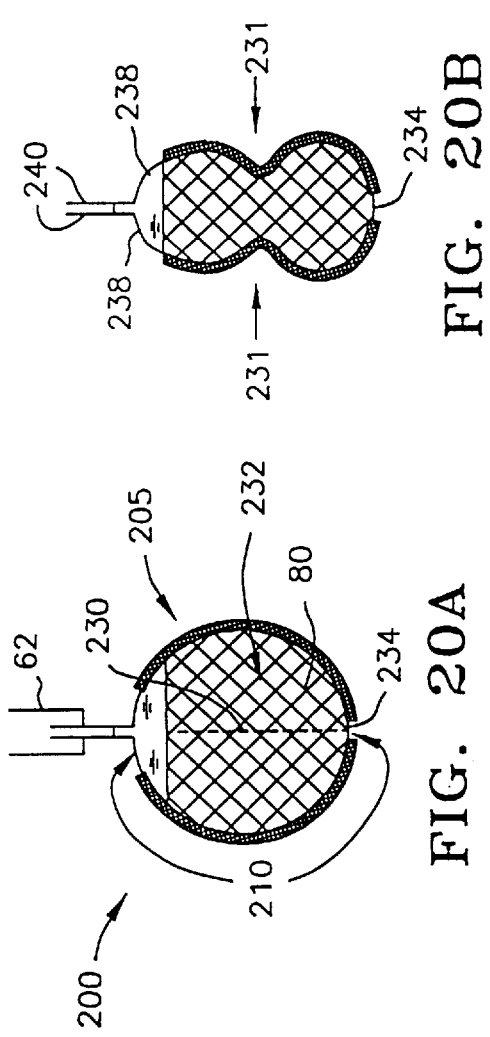
FIG. 20A
FIG. 20D
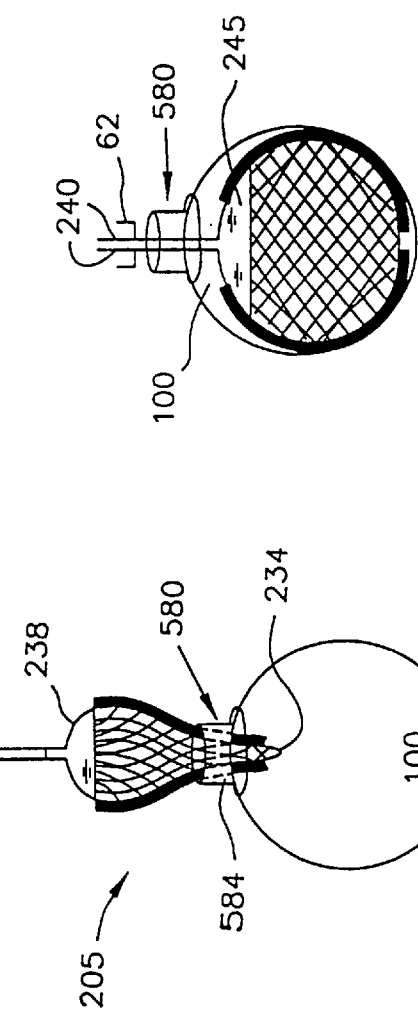
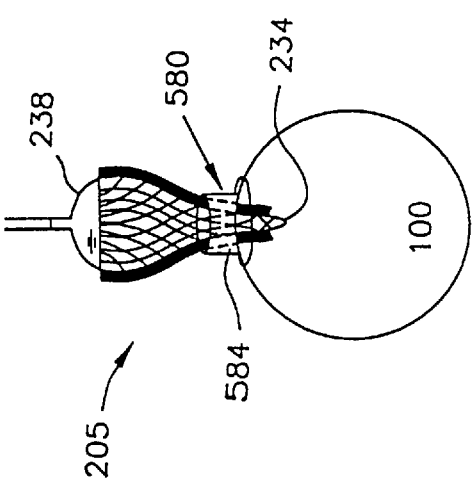
FIG. 20E
FIG. 20F

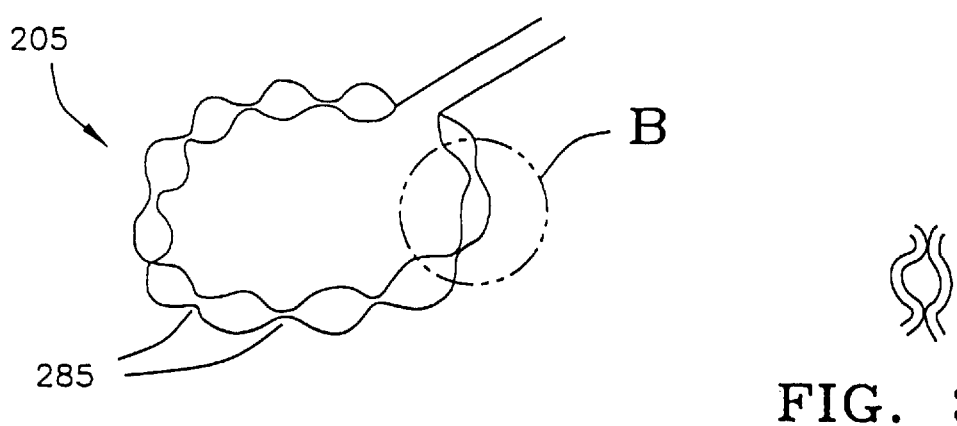
FIG. 30A
FIG. 30B
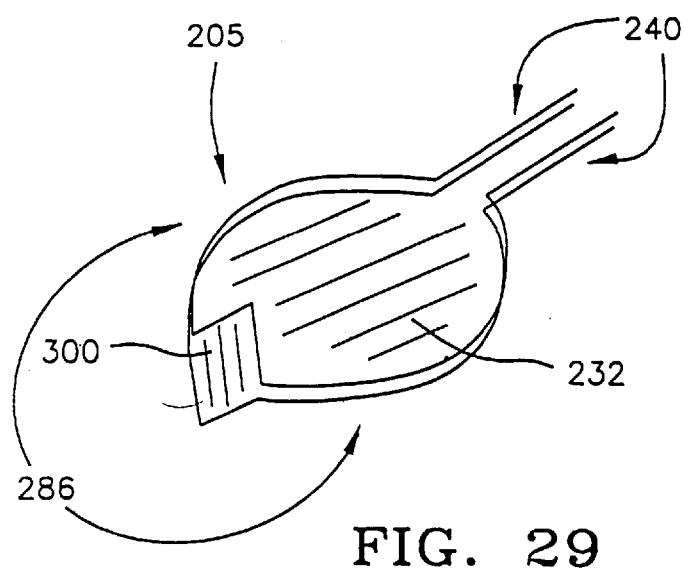
FIG. 29
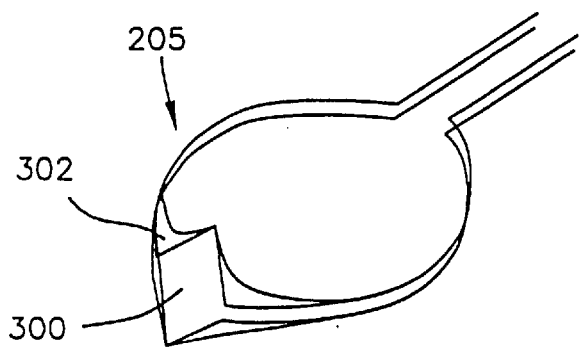
FIG. 29A

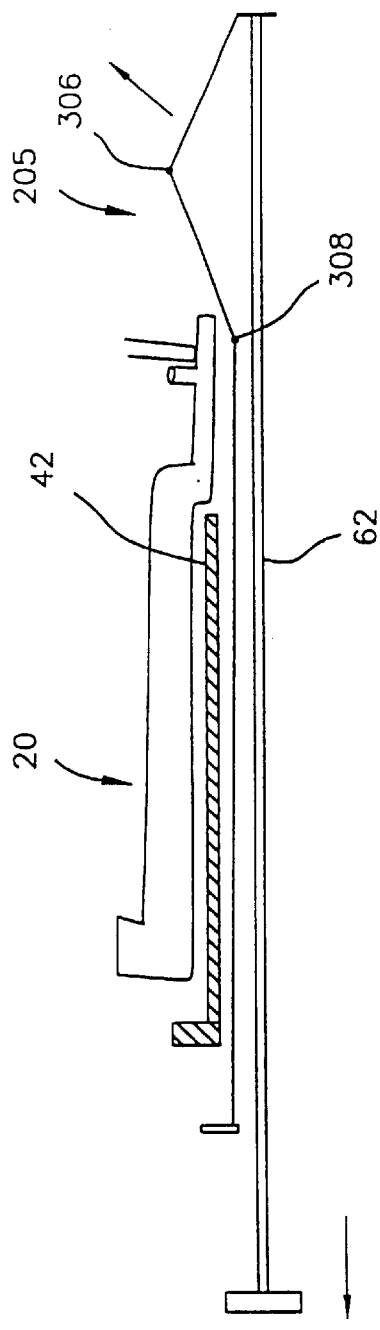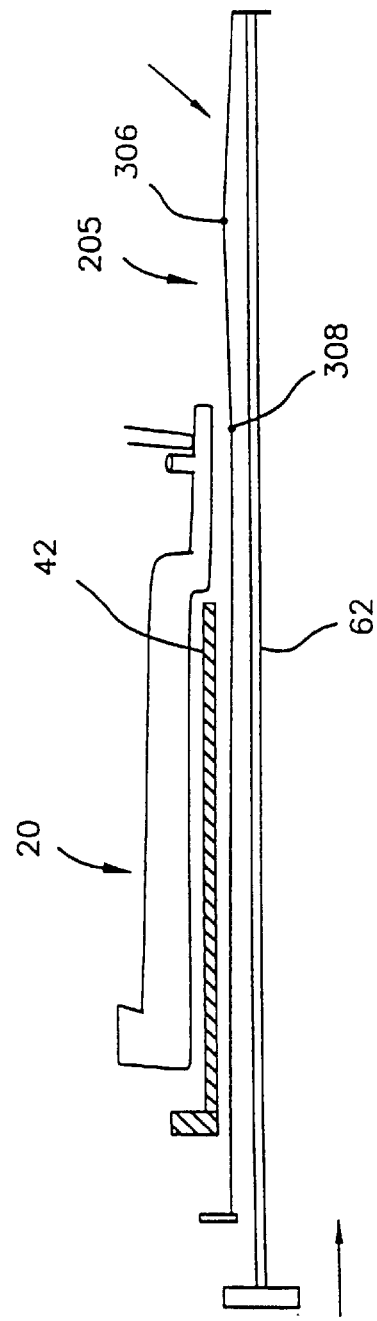

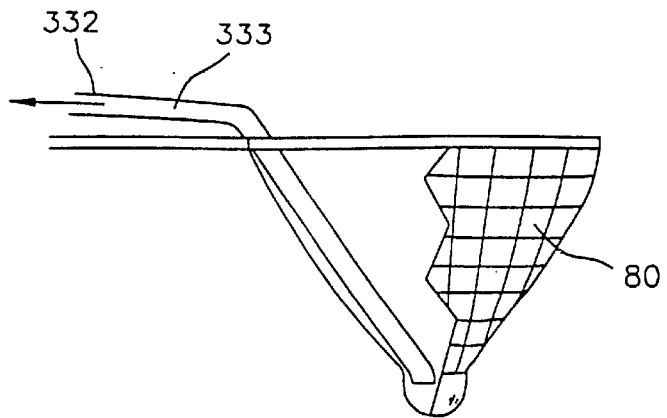
FIG. 39B
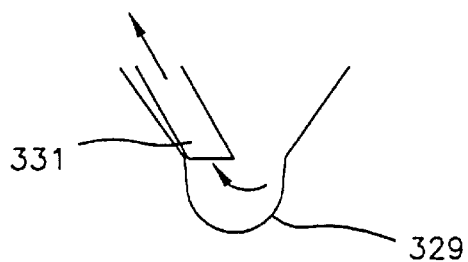 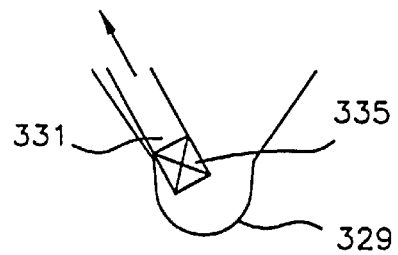
FIG. 39C    FIG. 39D
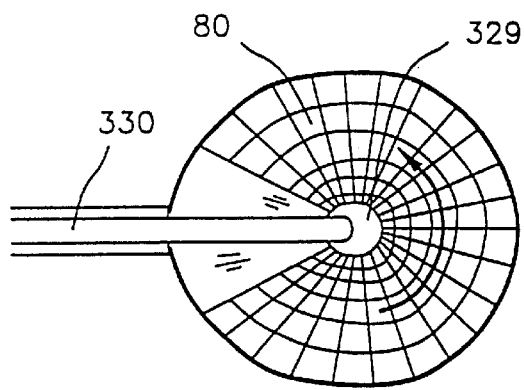
FIG. 39E

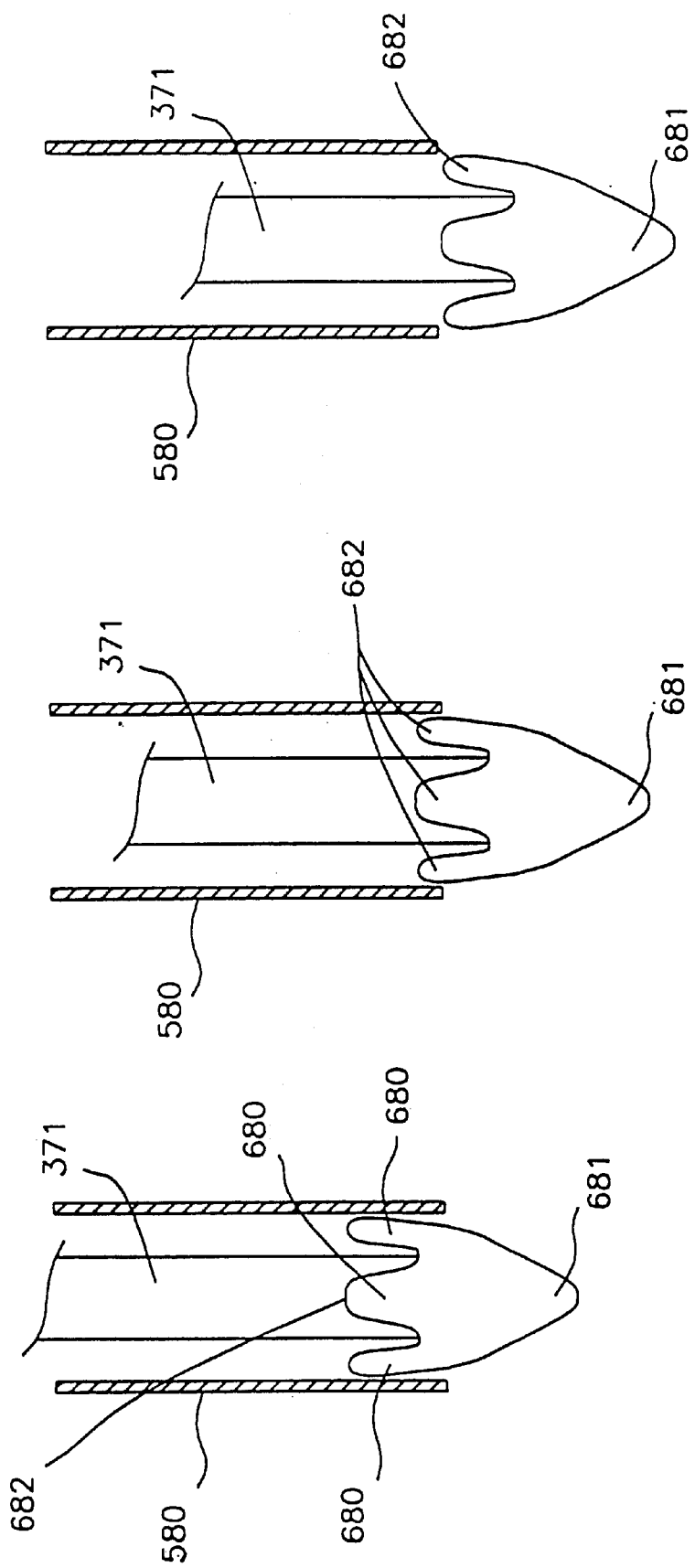

ADJUSTABLE BLOOD FILTRATION SYSTEM

This is a continuation of U.S. application Ser. No. 09/392,059, filed Sep. 8, 1999, now U.S. Pat. No 6,152,947, which is a continuation of U.S. application Ser. No. 09/070,660, filed Apr. 29, 1998, now U.S. Pat. No. 6,007,557, the contents of which are expressly incorporated herein by reference in their entirety.

FIELD OF THE INVENTION

The present invention relates generally to blood filter and associated devices for temporary placement in a blood vessel to capture embolic material, and more particularly to a hollow vessel insertion device with an adjustable filter apparatus for placement in a blood vessel to carry blood to the vessel and to entrap embolic material in the vessel, for example when delivering blood to the aorta from a bypass-oxygenator system during cardiac surgery. The present invention also relates to methods for protecting a patient from embolization that may be caused by procedures, such as incising, clamping and unclamping, which may dislodge atheromatous material from an artery.

BACKGROUND

During cardiac surgery, it is often necessary to introduce a cannula into an artery or other blood vessel. For example, an arterial cannula is typically introduced into the aorta to deliver blood from a bypass-oxygenator system. Such a cannula generally includes a proximal end for receiving blood from a bypass-oxygenator machine, a distal end for entry into an artery and a lumen extending between the proximal and distal ends.

One concern with such procedures is that calcified plaque or other embolic material may be dislodged, particularly when clamping or unclamping arteries such as the aorta. See Barbut et al., "Cerebral Emboli Detected During Bypass Surgery Are Associated With Clamp Removal," *Stroke*, 25(12):2398–2402 (1994), which is incorporated herein by reference in its entirety. Such embolic material may travel downstream, possibly becoming lodged in another portion of the blood vessel or possibly reaching a vital organ, such as the brain, where the material can cause substantial injury to the patient.

For this reason, some arterial cannulas may include a blood filter device attached directly to them. For example, an expandable filter device may be mounted on the distal end of a cannula, allowing the filter to capture any loose embolic material once the cannula is introduced into the vessel. Generally, such devices include an expandable frame, such as an inflation seal or an umbrella frame, and a filter mesh attached to the frame, the mesh being adapted to capture embolic material of a predetermined minimum size. The frame may be attached externally to the distal end, or alternatively, it may be retractably deployed from a lumen within the cannula.

The use of a cannula with such a filter device, however, may not be as effective as desired. For example, because the filter is generally attached to the distal end of the cannula, the filter may be exposed within the vessel for the entire duration of the procedure, sometimes several hours. Because of the length of time of most cardiac procedures, the filter mesh may eventually become clogged due to thrombus formation or buildup of embolic material, preventing the device from effectively capturing additional material and/or possibly impairing blood flow through the filter. If the filter is retractable, it may be closed within the vessel when it becomes clogged, but this prevents capture of embolic material throughout the remainder of the procedure.

Accordingly, there is a need for a filter device for use with an arterial cannula or other hollow vessel insertion device, such as an introducer, that minimizes the exposure of the filter within a blood vessel, thereby reducing the risk of clogging the filter mesh. Certain types of self-expanding modular filter devices have been described in U.S. Pat. No. 5,846,260, which is incorporated herein by reference in its entirety. However, there is a need for a modular filter apparatus with a filter that can be adjusted to fit various sizes of vessels. The exterior of such a device should optimally conform to the size and shape of the inner lumen of the vessel through which the emboli may pass to reduce the possibility of emboli escape around the exterior of the filter. The size of such a filter should be either self-adjusting or adapted to external operation to adjust the size to fit the vessel in which the filter resides. Further, there is a need for associated devices such as vessel sizing tools, expandable obturators, cannula liners and blood filtering system indexing/locking devices to assist in the use of the blood filtering system.

SUMMARY OF THE INVENTION

The present invention is directed to a modular adjustable blood filter device and a delivery system for intermittently introducing the filter device into a blood vessel during an extended surgical procedure and to methods for using such a device. The present invention is also directed to a hollow vessel insertion device, such as an introducer or an arterial cannula, with modular filter device for temporary placement in a blood vessel to carry blood to the vessel and to entrap embolic material in the vessel, for example when delivering blood to the aorta from a bypass-oxygenator system during cardiac surgery.

Generally, an embodiment of a blood filtering system includes a modular filter apparatus and a hollow vessel insertion device, such as an arterial cannula or an introducer, capable of receiving the filter for capturing embolic material in a blood vessel. The insertion device may be a stand-alone device, or may be part of a blood filtering system with the modular filtering apparatus. When the insertion device and the filter are used together, certain embodiments include indexing and locking mechanisms to assure proper alignment of the filter in the device. These indexing/locking mechanisms may also be included when the insertion device is used with other apparatuses, for example obturators.

When a cannula is used, it has a distal end adapted to enter an artery, a proximal end adapted to receive blood from a bypass oxygenator machine, and a lumen that extends from the proximal end to the distal end. The cannula can be a hybrid of extruded, drawn or welded metal tubing and molded or machined plastics, or could be made entirely of metal or of plastic. The cannula also includes a port for receiving the modular filter apparatus. The port may be attached to or integrally formed on the outer surface of the cannula, the inner surface of the cannula, such as a lumen parallel with the main cannula lumen, possibly on the front (downstream area), back (upstream area) or side of the cannula. Preferably, a side port is located adjacent the distal end of the cannula, for example above a suture flange thereon. More preferably, the side port extends diagonally from the outer surface to facilitate directing the filter device towards the distal end of the cannula. A passage extends from the side port to the lumen in the cannula, or alternatively, may extend distally from the side port along a wall of the cannula to an outlet on or adjacent the distal end of the cannula. The side port may include a hemostatic valve across the passage to provide a fluid-tight seal, yet allow a modular filter cartridge to be received in and removed from the side port. The cannula may also include a cannula liner to prevent the escape of blood from the outlet.

The filter apparatus includes a shaft with an adjustable filter frame disposed about the distal end of the shaft. The frame is adjustable between a contracted condition and an enlarged condition. The filter also includes a frame sizing mechanism and a filter mesh coupled to the frame for capturing embolic material. The filter apparatus may be a stand-alone device or may be removably insertable into the arterial cannula or introducer. Upon insertion through the cannula into the artery, the frame sizing mechanism adjusts the diameter of the filter frame to conform to the inner lumen of the vessel.

Embodiments of the modular filter apparatus include a semi-rigid shaft with some embodiments having a handle on the shaft proximal end. The frame may be metal, plastic, gel or foam or any combination thereof The filter mesh pore size ideally ranges from 40 to 120 microns, but other sizes may be used depending on the clinical need. The mesh may be plastic, fibrous, or metal, polyester, nylon, Teflon(k, or the like, and may be woven, stamped, etched, laser machined, molded, spun or layered. In some embodiments, the mesh is coated with a non-thrombogenic material, for example, heparin, or with a lubricious material. The frame sizing mechanism may be self-adjusting upon deployment, or may be controlled from the proximal end of the shaft. In the former case, for example, the adjustable frame may be formed from a superelastic or shape memory material, such as a Nitinol ring, that opens automatically when deployed. Preferably, the ring includes kinks where the ring is attached to the shaft, biasing the ring against the wall of a vessel, and maximizing the cross-section of the vessel intersected by the filter. Thus, once deployed, the ring automatically expands across the vessel, opening the filter, such as a substantially conical mesh, to capture embolic material in the vessel.

Alternatively, the frame sizing mechanism can be coupled to an external manipulating mechanism associated with the shaft, so that the size of the expansion frame may be externally controlled. For example, the adjustable frame may include an annular inflation seal, such as a silicon balloon, that may be filled with fluid to open the mesh across the vessel into which the device is deployed. In this embodiment, the shaft may include an inflation lumen extending between the proximal and distal ends thereof for injecting and removing fluid.

The frame sizing mechanism may also be mechanically operated, such as by a guide wire or a spring connected to the frame, generally controlled from the proximal end of the shaft. For example, the adjustable frame may include a plurality of struts that may be biased to the contracted condition, possibly using a shape memory material or a spring. A ring attached to the struts may be directed axially to expand and contract the struts respectively between the enlarged and contracted conditions.

Certain embodiments of the modular filter device also includes a tubular cartridge into which the expandable filter device may be inserted. Generally, the cartridge is a tubular member providing a hemostatic seal or a one-way valve between the shaft on the filter device and the port on the cannula or the introducer, or the cartridge may include a hemostatic valve to provide a fluid-tight seal between the cartridge and the filter device inserted therein. The cartridge generally has a shape similar to the port, as well as to the shaft on the filter device. Preferably, these components have similar cross-sections, such as a substantially square, rectangular or oval shape, that limit the arterial cannula with modular filter device to a predetermined assembled orientation that ensures that the filter device is deployed across the vessel in the proper orientation. The distal end of the filter is generally inserted into the cartridge, such that the frame and mesh are substantially contained within the cartridge, thereby providing a modular filter cartridge.

The modularity and adjustability of the filter apparatus, combined with its capability of insertion into an introducer or the port of the cannula, arc important features in the methods of use that are also described. One method of temporarily filtering embolic material from the blood in a blood vessel includes the steps of first inserting the distal end of the insertion device into a blood vessel, such as the aorta, using conventional procedures. A modular filter apparatus is then inserted into the device and is advanced into the vessel. The frame sizing mechanism is operated to enlarge or contract the adjustable filter frame to conform to the size of the vessel thus opening the filter mesh substantially across the vessel and capturing any embolic material traveling therethrough. At any time, the adjustable frame may be closed to its contracted condition, either automatically by withdrawing the adjustable filter, or by mechanically closing it as described above, entrapping any embolic material captured by the mesh. The adjustable filter may be withdrawn into the insertion device by pulling the shaft proximally, and the filter may then be removed from the device if desired. A new modular filter may be then be inserted into the device, and the new filter introduced into the vessel.

Certain embodiments of the method just described include providing an elongated aspiration tube having a lumen connecting openings in its proximal and distal ends. The proximal end is adapted to connect to an aspiration source and the distal end is slideably insertable into the proximal end of a hollow filter shaft that is also provided. Once the filter is deployed within the vessel, the aspiration tube is slideably inserted through the shaft of the filter until the distal end of the tube lies near the inner surface of the filter mesh. Negative pressure is then applied to the proximal end of the aspiration tube and embolic debris is drawn out of the filter and into the tube. The tube may then be removed from the vessel.

The ability to replace the filter at any time during a procedure is particularly useful in cardiac surgery. For example, a cannula and filter may be deployed as described above within the aorta. The aorta may then be clamped in preparation for a bypass procedure, possibly dislodging embolic material from the wall of the aorta and traveling downstream. With the filter deployed, however, embolic material released during this action may easily be captured by the filter device. Once the aorta is clamped, the risk of embolic material breaking loose is substantially reduced, and so the filter may be removed without substantial concern about embolic material escaping to other areas of the patient.

Later in the surgery, a new filter may be introduced into the aorta when the risk of embolic material becoming dislodged is again increased, as for example when the aorta is unclamped. Because a new filter may be deployed, any embolic material that is dislodged has a much greater likelihood of being captured by the filter without substantially impairing blood flow through the vessel. Thus, a cannula with modular filter apparatus may more effectively capture and remove embolic material released during extended procedures, such as coronary bypass surgery.

Associated devices are also described. For instance, it is often helpful to know in advance the size of the vessel into which a filter is to be deployed. Therefore, a vessel sizing tool is described that includes a vessel sizing shaft that is slideably insertable into a vessel or a hollow vessel insertion device. The shaft has a plurality of visible markings along the shaft indicating units of distance, one of which aligns with an indicator on the insertion device, or with the top of the vessel, when the distal end of the shaft has engaged the wall opposite the insertion point. Other embodiments include a vessel sizing cartridge into which the shaft is inserted.

Methods of using the tool are also described. First, a hollow vessel insertion device adapted to receive a vessel sizing tool and a vessel sizing tool adapted to slideably insert into the insertion device are provided. Next, the distal end of the insertion device is introduced into the vessel. Then the distal end of the vessel sizing tool is slideably inserted into the insertion device, and the tool is advanced through the lumen in the insertion device until the most distal marking on the tool aligns with the indicator on the device, indicating that the distal end of the tool has just entered the vessel. Next, the tool is carefully advanced until the distal end of the tool touches the vessel wall opposite the insertion point, and the visible marking that now aligns with the indicator on the insertion device is noted. This visible marking denotes the depth of the tool in the vessel and thus the vessel diameter.

It is also useful to reduce trauma to the vessel that can be caused by a hollow vessel insertion device and thus an expandable obturator is also described. One embodiment of an obturator includes an obturator shaft that has a tapered distal end, a distal region and an outer surface and a plurality of spaced collet segments arranged coaxially around the distal region of the obturator shaft. Each segment is expandable between a contracted condition and an expanded condition and each segment has an inner surface that conforms to the outer surface of the obturator shaft and a proximal end coupled to the distal region of the shaft. The segment also includes an outwardly flaring elongated member that is expandable away from the outer surface of the obturator shaft. This elongated member forms a collet head at the distal end of the collet segment. The collet head has a proximal end that gradually thickens from the elongated member thereby forming a recess in the region where the elongated member is associated with the collet head. The distal end of the collet head is tapered to a thickness less than the proximal end of the head. This configuration allows the distal end of the insertion device to rest in the recess behind the collet head, and the overall profile of the collet head and distal end of the shaft is smoothly tapered to advance the entering insertion device.

Methods of using the expandable obturator are also described. In one embodiment, the obturator is slideably inserted into the proximal end of the insertion device, causing the collet segments of the obturator to contract about the shaft. The obturator is then advanced through the lumen of the insertion device until the collet heads of the obturator project just beyond the distal end of the insertion device. The collet segments then flare to an expanded condition and the distal end of the insertion device rests in the recesses formed behind the collet heads. The insertion device and associated obturator are then advanced through an incision in the vessel until the distal end of the insertion device enters the vessel. The obturator may then be removed by pulling on the proximal end and causing the proximal portion of the collet heads to slide under the distal end of the insertion device thereby forcing the collet heads to once again assume a contracted condition suitable for removal.

Accordingly, a principal object of the present invention is to provide a modular adjustable blood filter apparatus and delivery system that allows the filter to be decoupled from the delivery system when not needed, and that allows a new filter to be introduced to more effectively capture embolic material within the vessel, such as during an extended surgical procedure.

It is also an object of the present invention to provide an insertion device with modular filter apparatus that substantially minimizes the likelihood of the blood filter becoming clogged and ineffective during use.

Additional objects and features of the present invention will become apparent from consideration of the following description taken in conjunction with the accompanying drawings.

BRIEF DESCRIPTION OF THE DRAWINGS

FIG. 1 is a side view of an embodiment of an arterial cannula receiving a modular filter cartridge therein.

FIG. 2 is a partially cut-away side view of the arterial cannula of FIG. 1 with the modular filter cartridge received therein, showing the filter partially deployed.

FIG. 3 is another partially cut-away side view of another preferred embodiment of an arterial cannula with the modular filter cartridge received therein, showing an alternative arrangement of the deployed filter.

FIGS. 4 and 5 are side views of the distal end of an arterial cannula introduced into a blood vessel, showing the side port located on the back and on the front, respectively, of the cannula.

FIG. 19 is a perspective view of a distal portion of the arterial cannula with modular filter device of FIG. 18, prior to the modular filter cartridge being received in the arterial cannula.

FIGS. 20A–F are top elevations of an embodiment of an adjustable filter device showing the insertion of the device through a hollow vessel insertion device and into a vessel.

FIG. 29 shows a perspective elevation of an adjustable frame with a stabilizing plate.

FIG. 29A shows the embodiment of FIG. 29, where the stabilizing plate is covered with a protective covering.

FIG. 30A shows another embodiment of an adjustable frame where the sizing mechanism permits flexion and extension of the frame material.

FIG. 30B is a detail of the frame of FIG. 30A.

FIGS. 34A–B show the device of FIG. 33A as it is expanded and contracted by manipulating the arms of the frame.

FIG. 39B shows a partial cutaway of the embodiment of FIG. 39A.

FIG. 39C shows a detail of the sac region of an embodiment of a filter device with an aspiration tube.

FIG. 39D shows a detail of the sac region of an embodiment of a filter device with an aspiration tube that has a turbine at its distal tip.

FIG. 39E shows a top elevation of an embodiment of a rotating filter with an aspiration tube.

FIGS. 43A–C show a lateral cross-section of another embodiment of an expandable obturator as it progresses through and out the distal end of an insertion device.

DETAILED DESCRIPTION OF THE PREFERRED EMBODIMENTS

Figure 16:
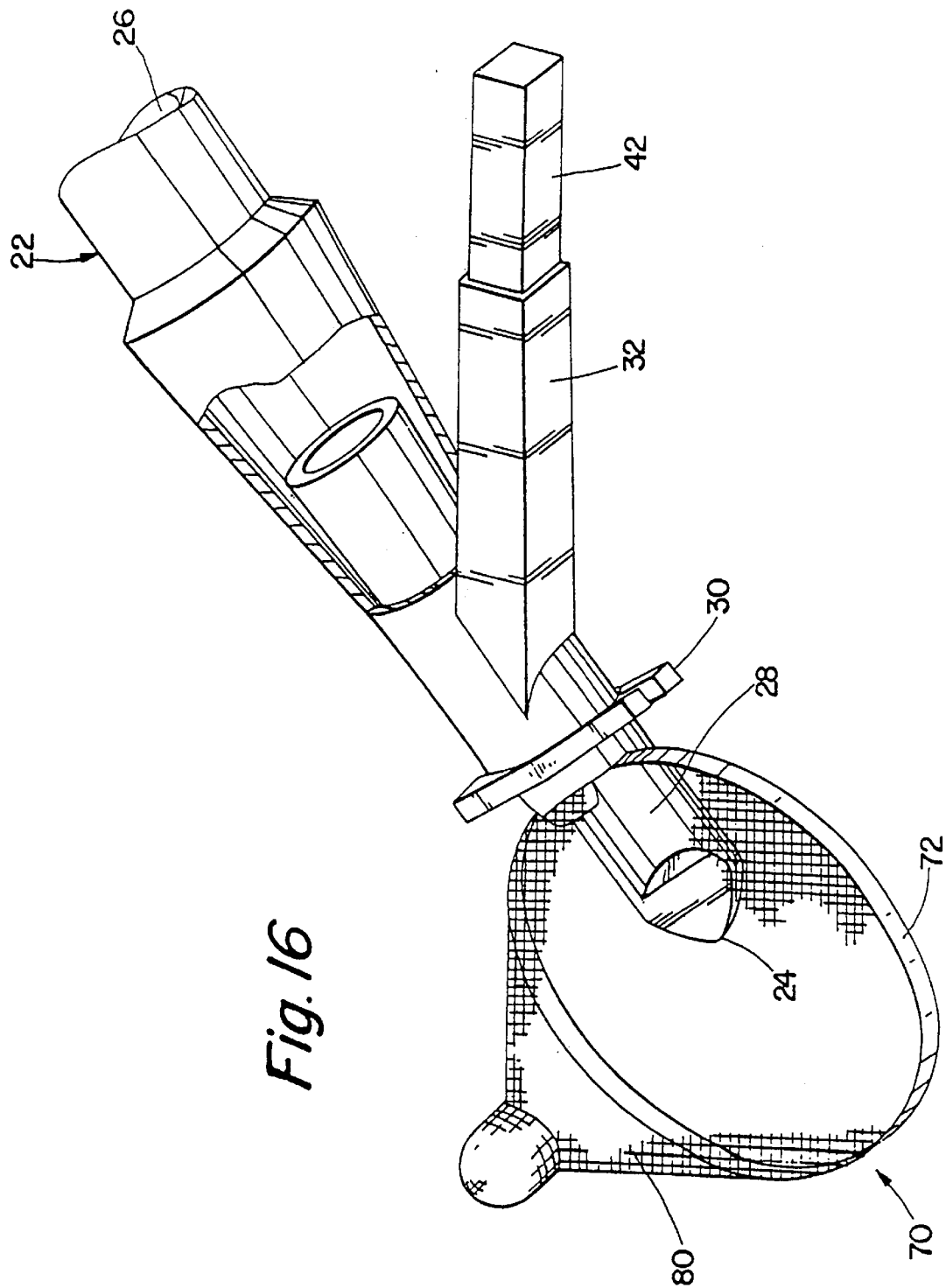
FIGS. 16 and 17 are perspective views of the distal portion of a cannula with modular filter device with the expandable filter device deployed.
Figure 17:
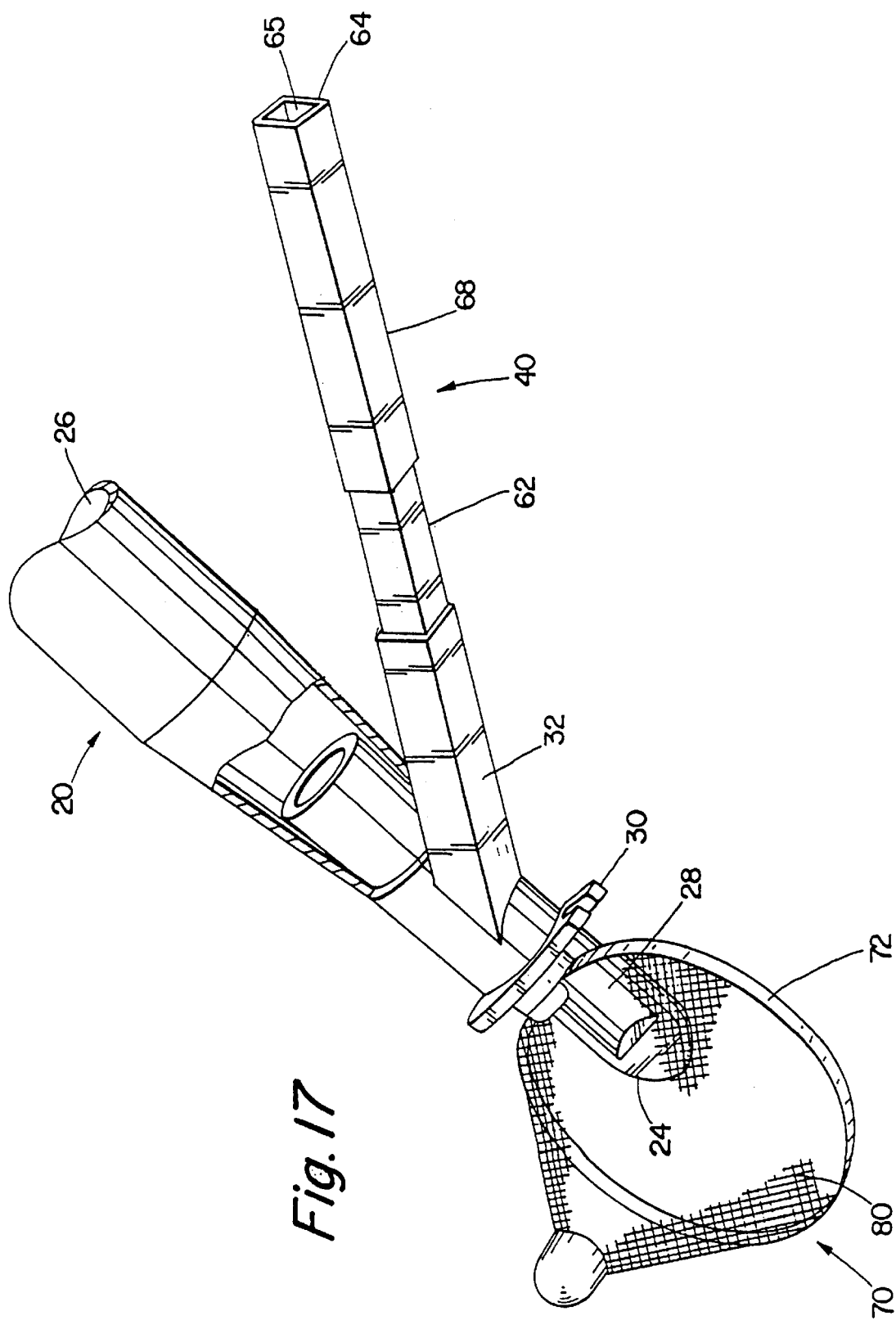
Figure 18:
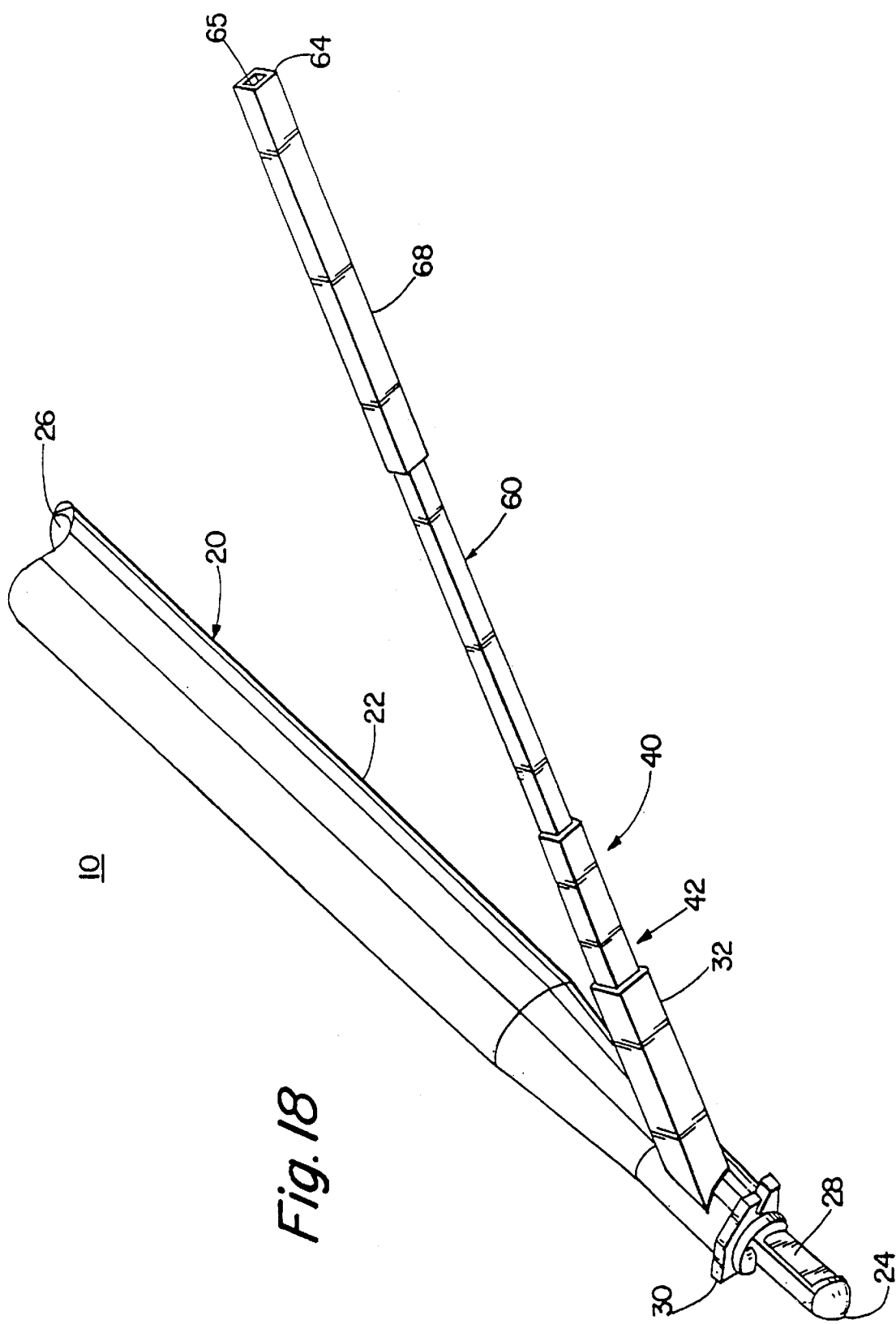
FIG. 18 is a perspective view of a distal portion of an arterial cannula with modular filter device, showing the modular filter cartridge after being received in the arterial cannula.
Figure 20G:
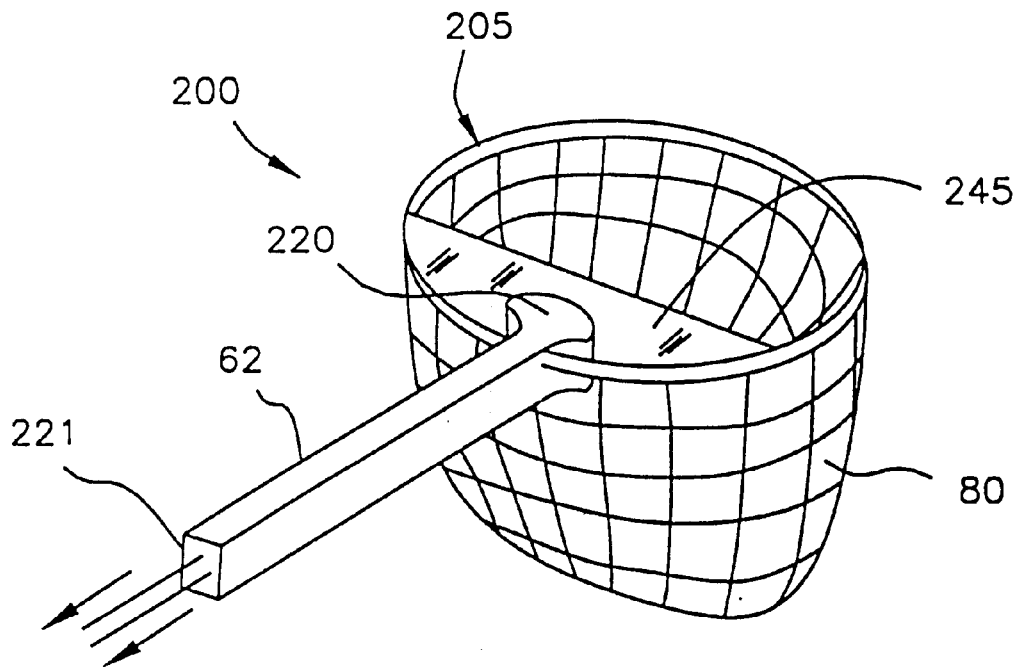
FIG. 20G is a perspective elevation of the device of FIG. 20A.
Figure 20H:
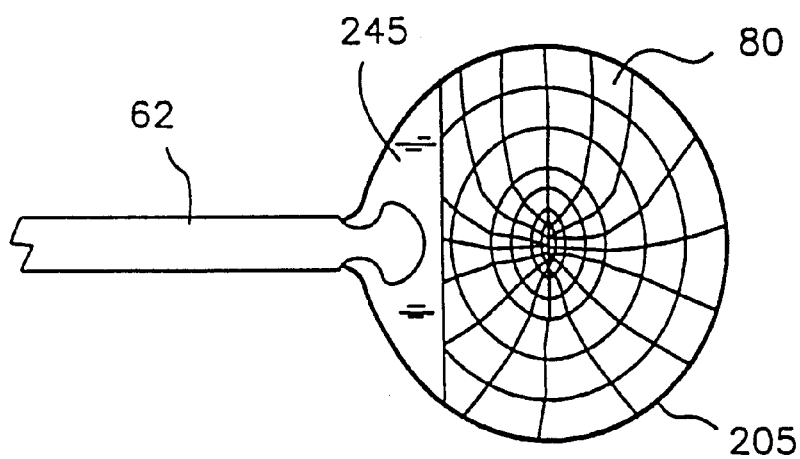
FIG. 20H is a top elevation of the device of FIG. 20A.

Turning now to the drawings, FIGS. 1–5 and 16–19 show embodiments of an arterial cannula with modular filter device 10. As shown in FIGS. 18 and 19, the device 10 generally includes three components, namely a cannula 20, a tubular cartridge 42 and an expandable filter device 60. In certain embodiments, the latter two components together defining a modular filter apparatus 40.

The cannula 20 is an elongate tubular member 22, having a proximal end (not shown), a distal end 24, and a lumen 26 which extends between the proximal and distal ends 24. The proximal end is adapted for receiving blood from a bypass-oxygenator machine (not shown). The distal end 24 has a tapered, curved and/or rounded end adapted to enter an artery (not shown), and includes an outlet 28 communicating with the lumen 26. The cannula 20 may be formed from a substantially rigid material.

The cannula 20 includes a side port 32 for receiving the modular filter apparatus 40. The side port 32 may be attached to or integrally formed on the cannula 20, possibly on the front (downstream area), back (upstream area) or side of the cannula, as shown, for example, in FIGS. 4 and 5. Preferably, the side port 32 is located adjacent the distal end 24 of the cannula 20 above a suture flange 30 thereon, and extends diagonally from the cannula 20. A passage 34 extends from the side port 32 to the lumen 26 in the cannula 20, as shown in FIG. 2. Alternatively, the passage 34 may communicate with the lumen 26 of the cannula 20, and the distal end 24 of the cannula 20 may include a separate filter outlet 29, as shown in FIG. 3, or the passage 34 may be isolated from the lumen 26 and extend distally from the side port 32 along a wall of the cannula 20 to a filter outlet (not shown) on or adjacent the distal end 24 of the cannula 20. Preferably, the side port 32 also has a predetermined cross-sectional configuration corresponding to the modular filter apparatus 40, as explained below. Optionally, the side port 32 may include a hemostatic valve (not shown) across the passage 34, providing a fluid-tight seal that prevents fluid flow out of the passage 34 from the lumen 26 of the cannula 20, yet allows the modular filter apparatus 40 to be received in and removed from the side port 32.

The tubular cartridge 42 is generally an elongate tubular member having a proximal end 44, a distal end 46 and a channel (not shown) for receiving the filter device 60. The cartridge 42 facilitates the modular nature of the device 10, providing a hemostatic seal between the filter device 60 and the side port 32 on the cannula 20. The cartridge 42 may have an outer wall 48 shaped similarly to the passage 34 in the side port 32 as shown in FIGS. 18 and 19, thereby providing a fluid-tight seal when the modular filter apparatus 40 is received in the side port 32. The channel in the cartridge 42 may also have a shape similar to the filter device 60 to provide a fluid-tight seal between the cartridge 42 and the filter device 60. Alternatively, a hemostatic valve (not shown) may be provided across the channel, for example at the proximal end 44 of the cartridge 42 to provide a fluid-tight seal, yet allow the filter device 60 to be slideably received in and possibly removed from the cartridge 42. Preferably, the cartridge 42 is provided from molded plastic materials that provide a hemostatic seal when the outer wall 48 of the cartridge 42 slideably engages the passage 34 in the side port 32, and when the shaft 62 of the filter device 60 slideably engages the channel in the cartridge 42.

Referring to FIGS. 16–19, the expandable filter device 60 generally includes a shaft 62, a handle 68 and an expandable filter 70. The shaft 62 is generally an elongate member, having the handle 68 on its proximal end 64 and the expandable filter 70 on its distal end 66. Optionally, the shaft 62 may include a passage 65, such as for an inflation lumen or a mechanical control apparatus for the expandable filter 70, extending between the proximal end 64 and the distal end (not shown). The shaft 62 may be provided from a resilient semi-rigid material that is biased to a particular shape, for example to remain substantially straight, but is sufficiently flexible to follow the contour of the passage 34 and/or the lumen 26 in the cannula 20. Exemplary materials include plastic or metal. Generally, the shaft 62 may have a cross-section corresponding to the channel in the cartridge 42, thereby providing a hemostatic seal that prevents flow of fluid through the channel, although alternatively, the cartridge 42 may include a separate seal as described above, or the shaft 62 may include a seal (not shown).

Preferably, the cross-sections of the side port 32, the cartridge 42 and the shaft 62 have a substantially square, rectangular, circular, oblong or other similar shape. The corresponding shape or the indexing/locking mechanisms hereinafter described, preferably limit the device 10 to being assembled in a single orientation. This may be particularly important to ensure that the expandable filter 70 is deployed within a blood vessel such that it intersects the vessel, and substantially engages the wall of the vessel to effectively capture embolic material. The side port 32 also helps orient the surgeon using the device 10 with respect to the vessel. For example, with the side port 32 on the side of the cannula 20 as shown in FIGS. 16 and 17, the surgeon may orient the side port 32 perpendicular to the vessel to ensure that the outlet is directed downstream and that the filter is oriented for proper deployment. Alternatively, an indexing/locking mechanism may provide such orientation for circular shaped devices.

Figure 8:
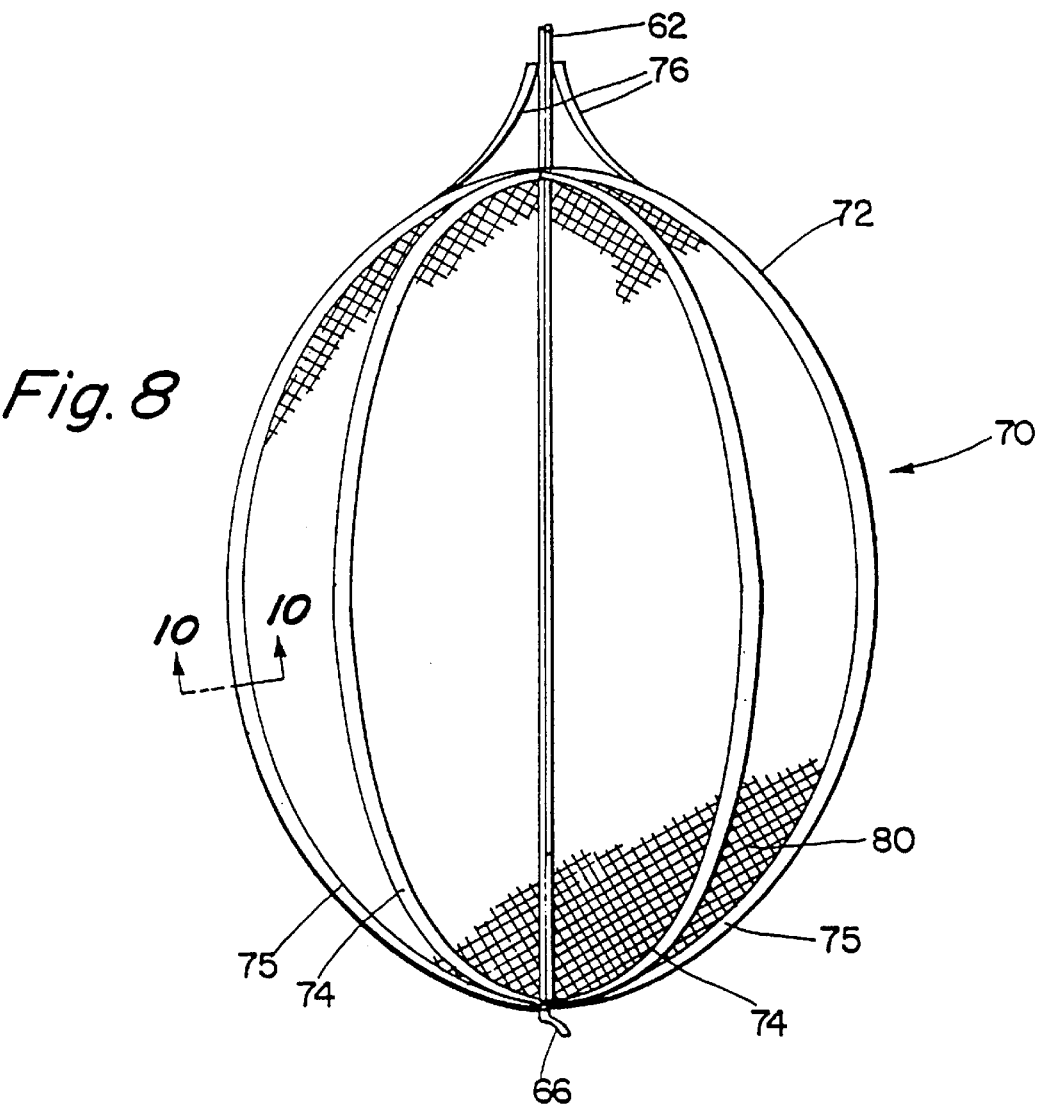
FIG. 8 is a back view of an embodiment of an expandable filter device in accordance with the present invention.
Figure 9:
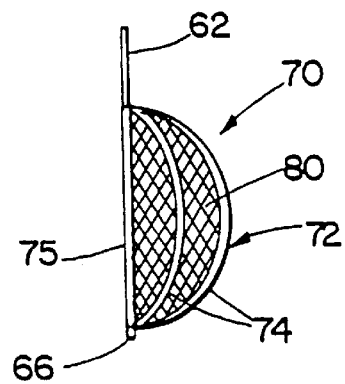
FIG. 9 is a side view of the expandable filter device of FIG. 8.

Turning now to FIGS. 8 and 9, an embodiment of an expandable filter 70 is shown that may be provided on or near the distal end 66 of the shaft 62. The expandable filter 70 generally includes an expansion frame 72 capable of assuming enlarged and contracted conditions, and filter mesh 80. Preferably, the expansion frame 72 includes a plurality of struts 74 that may be expanded and contracted to define respectively the enlarged and contracted conditions. Filter mesh 80 is attached to the struts 74, 75 of the expansion frame 72. For a complete explanation of the design and construction of a filter mesh for use herein, the reader is referred to Barbut et al., U.S. Pat. No. 5,769,816, Barbut et al., U.S. application Ser. No. 08/553,137, filed Nov. 7, 1995, Barbut et al., U.S. application Ser. No.

08/580,223, filed Dec. 28, 1995, Barbut et al., U.S. application Ser. No. 08/584,759, filed Jan. 9, 1996, Barbut et al., U.S. application Ser. No. 08/645,762, filed May 14, 1996, and U.S. application Ser. No. 08/842,727, filed Apr. 16, 1997. The disclosure of these references and any others cited herein are expressly incorporated herein by reference.

In the preferred embodiment of FIGS. 8 and 9, the struts 74, 75 may open automatically into a substantially hemispherical shape when deployed, for example, by providing them from plastic, spring stainless steel, or a superelastic and/or shape memory material, such as Nitinol, that is biased to expand to define the hemispherical shape. Stabilizers 76 may be provided to stabilize the expansion frame 72, or may be omitted if the bias of the struts 74, 75 provides sufficient stability. In addition, the struts 74, 75 may be attached to the shaft 62 using hinged joints to facilitate expanding and contracting the expansion frame 72.

Figure 10:
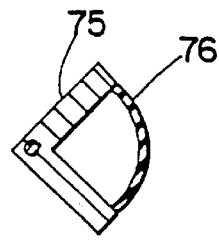
FIG. 10 is a cross-section of a support strut taken along line 10—10 of FIG. 9, including an inflation seal for engaging the wall of a vessel when the expandable filter device is deployed.
Figure 11:
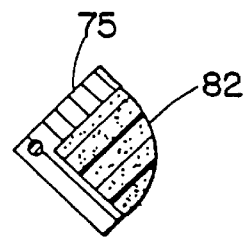
FIG. 11 is a cross-section of an alternative embodiment of a support strut taken along line 10—10 of FIG. 9, including a self-expanding foam for engaging the wall of a vessel.

The open end struts 75 may also include seals for engaging the wall of a blood vessel to substantially minimize embolic material traveling around the periphery of the deployed expandable filter 70. For example, as shown in FIG. 10, the struts 75 may include a silicone or urethane balloon 76 attached along their length that may be inflated from a lumen (not shown) extending between the struts 75 and the shaft 62. The balloon 76 may also be used to expand the expansion frame 72 to its enlarged condition if the struts 74, 75 are unbiased or are biased to the contracted condition. Alternatively, as shown in FIG. 11, the struts 75 may include a self-expanding foam 82, such as silicone, that will expand when the expandable filter 70 is deployed to substantially engage the wall of the vessel.

Alternatively, as shown in FIG. 3, the struts 74 may have an umbrella-like configuration, which may be particularly useful when the expandable filter 70 is deployed out a filter outlet 29 on the back (upstream side) of the cannula 20. The struts 74 may be biased to expand to the enlarged condition. To remove the expandable filter 70, the shaft 62 may be pulled proximally, closing the struts 74 as they enter the filter outlet 29.

Figure 6:
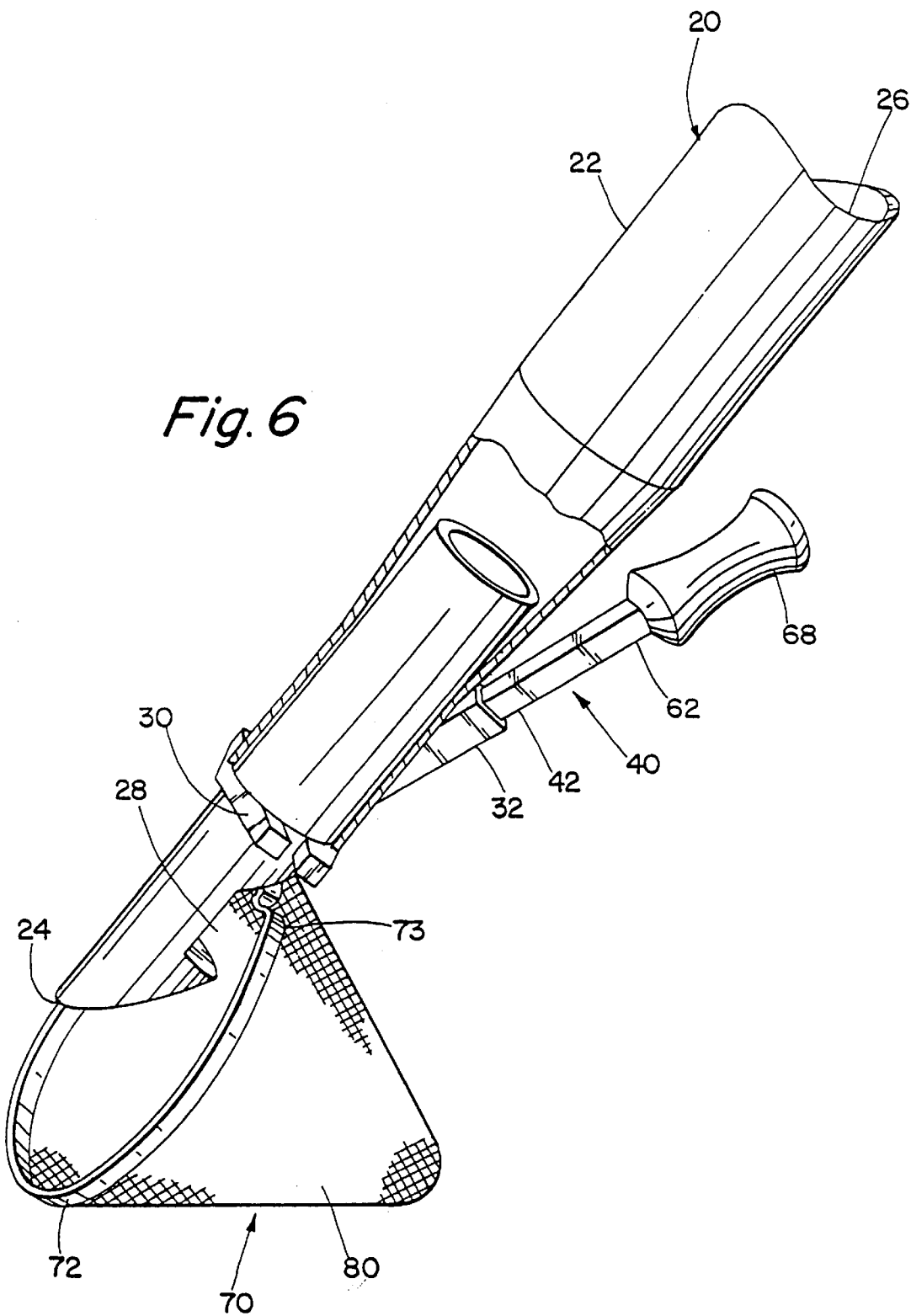
FIG. 6 is a perspective view of a distal portion of an arterial cannula from a generally upstream position, showing a conical filter device fully deployed.
Figure 7:
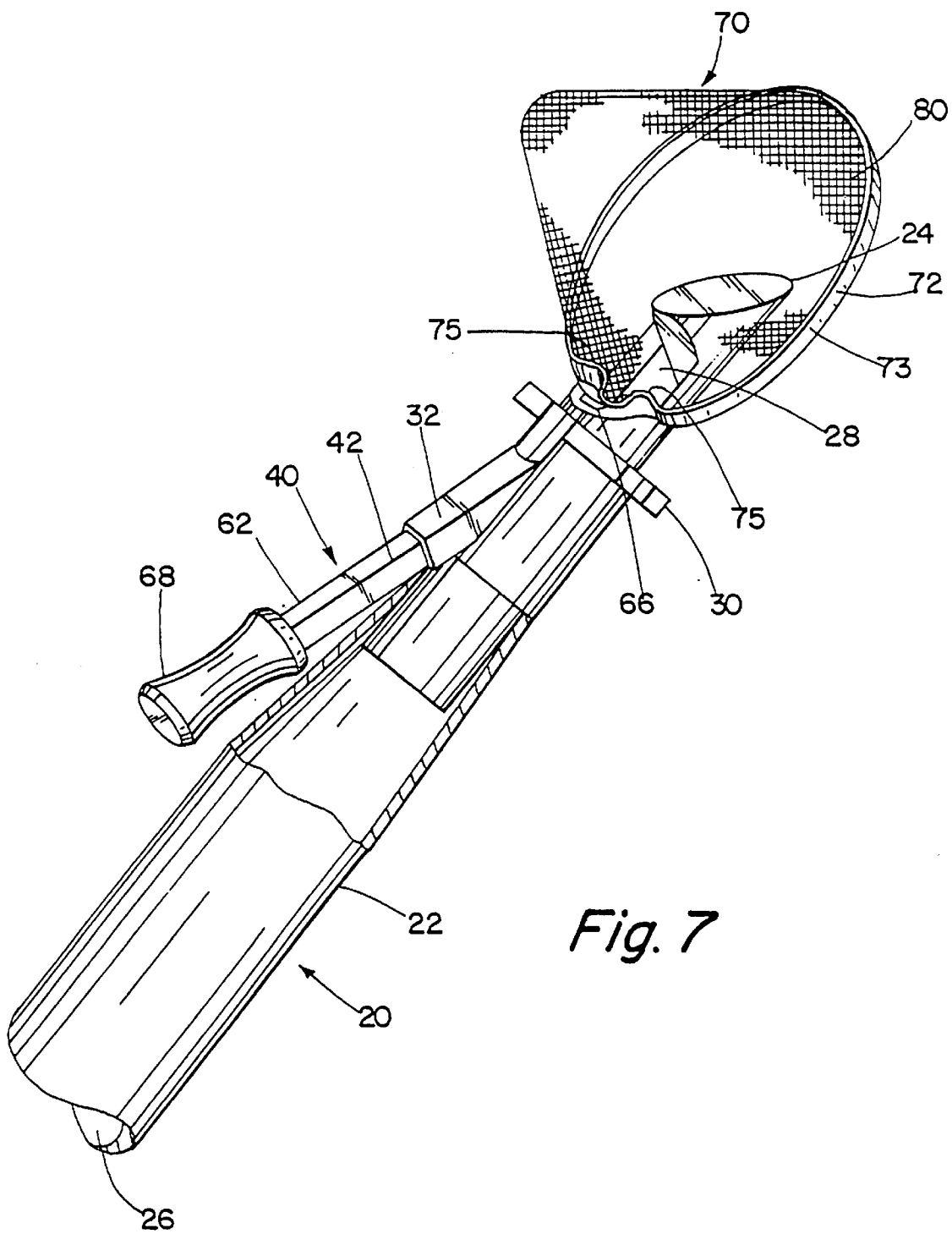
FIG. 7 is a perspective view of the distal end of the arterial cannula of FIG. 6 from a generally downstream position.

In another preferred embodiment, such as that shown in FIGS. 6 and 7, the expansion frame 72 is a self-expanding ring 73 formed from spring stainless steel or a superelastic and/or shape memory material, such as Nitinol. The ring 73 may be compressed for insertion into the cartridge 42, but, because of the shape memory of the material, it is biased to open automatically into an annular shape when the expandable filter 70 is deployed. Preferably, the ring 73 also includes a kink 75 adjacent the distal end 66 of the shaft 62 to bias the ring 73 against the wall of the vessel, and maximize the cross-section of the vessel intersected by the expandable filter 70. Without the kink 75, the ring may deform slightly, creating an imperfect circular cross-section that may allow embolic material to escape around the periphery of the deployed expandable filter 70. The filter mesh 80 attached to the ring 75 preferably has a substantially conical shape, such that when the ring 75 expands across the vessel, the mesh 80 is pulled open downstream by blood flow in the vessel to capture any embolic material traveling through the vessel.

Figure 15:
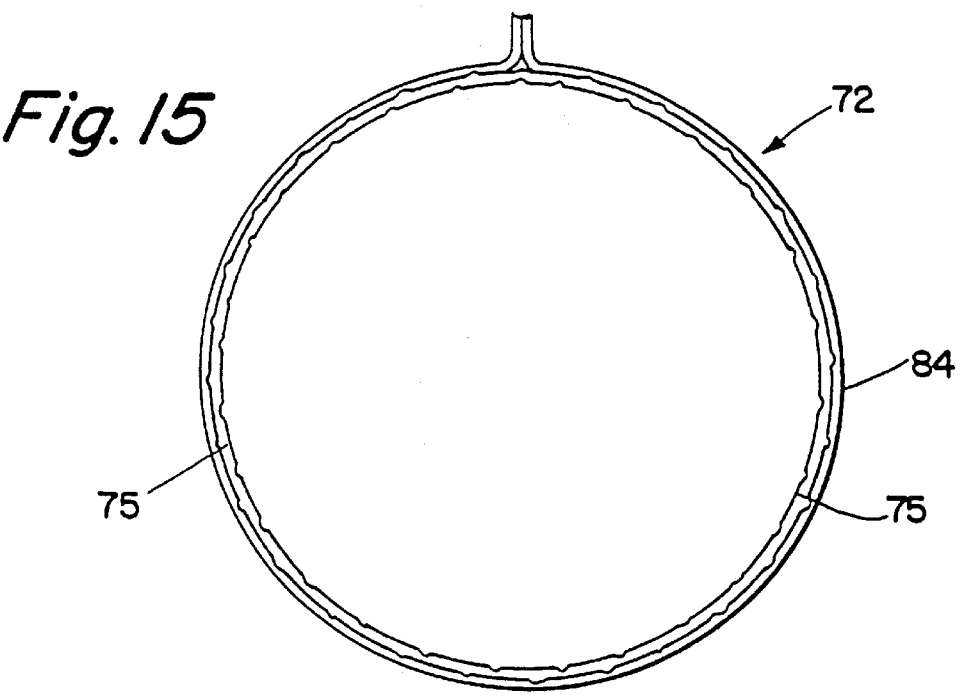
FIG. 15 is a side view of an embodiment of an expansion frame having "sausage" struts and an inflation seal.

Alternatively, as shown in FIG. 15, the expansion frame 72 may include a ring 75 having a "sausage" configuration, that is, having hinges or dimples on several locations around the ring 75, allowing the ring 75 to enlarge and contract more easily, and conform tightly to vessel lumen topography. Preferably, this embodiment also includes a balloon 84 attached around the periphery of the ring 75 to guide the ring 75 to assume a substantially round configuration when the balloon 82 is inflated.

Figure 12:
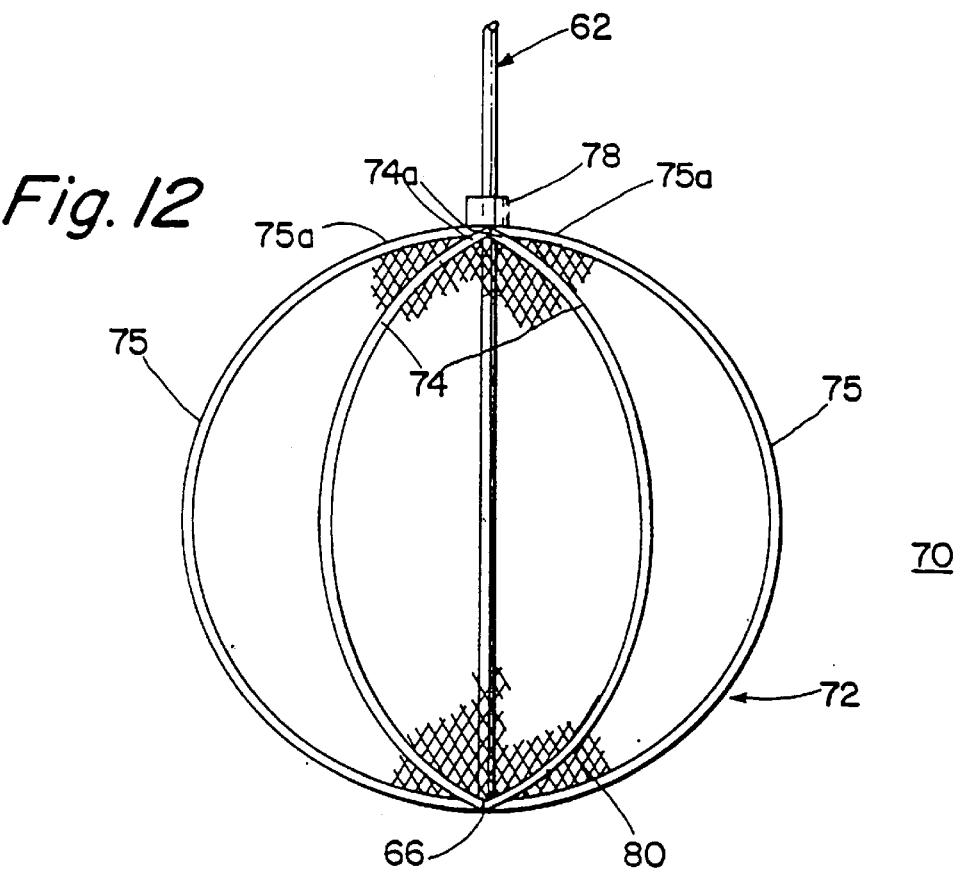
FIGS. 12 and 13 are side views of alternative embodiments of expansion frames for use in an expandable filter device.
Figure 13:
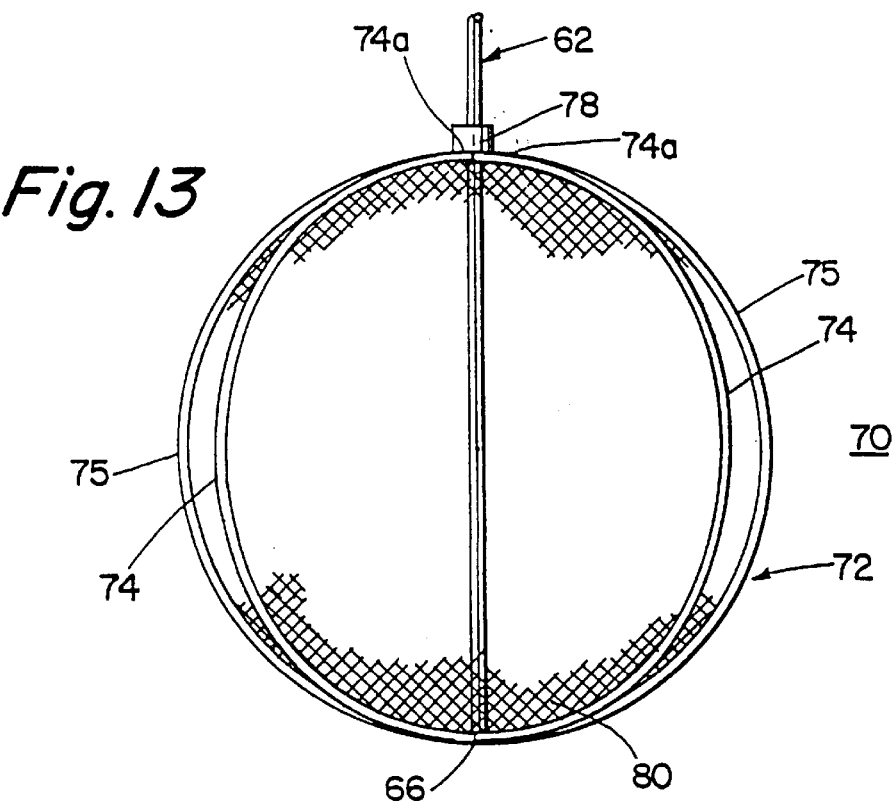

In still another preferred embodiment, a mechanically-operated expansion frame 72 may be provided. For example, the expansion frame 72 of FIGS. 12 and 13 includes a ring 78 to which one end 74a, 75a of the struts 74, 75 are attached. The ring 78 may be slideable axially in relation to the shaft 62, for example by use of a control wire or sleeve (not shown) to expand and contract the struts 74, 75. Alternatively, the ring 78 may be twisted radially to open and/or close the struts 74, 75.

Figure 14:
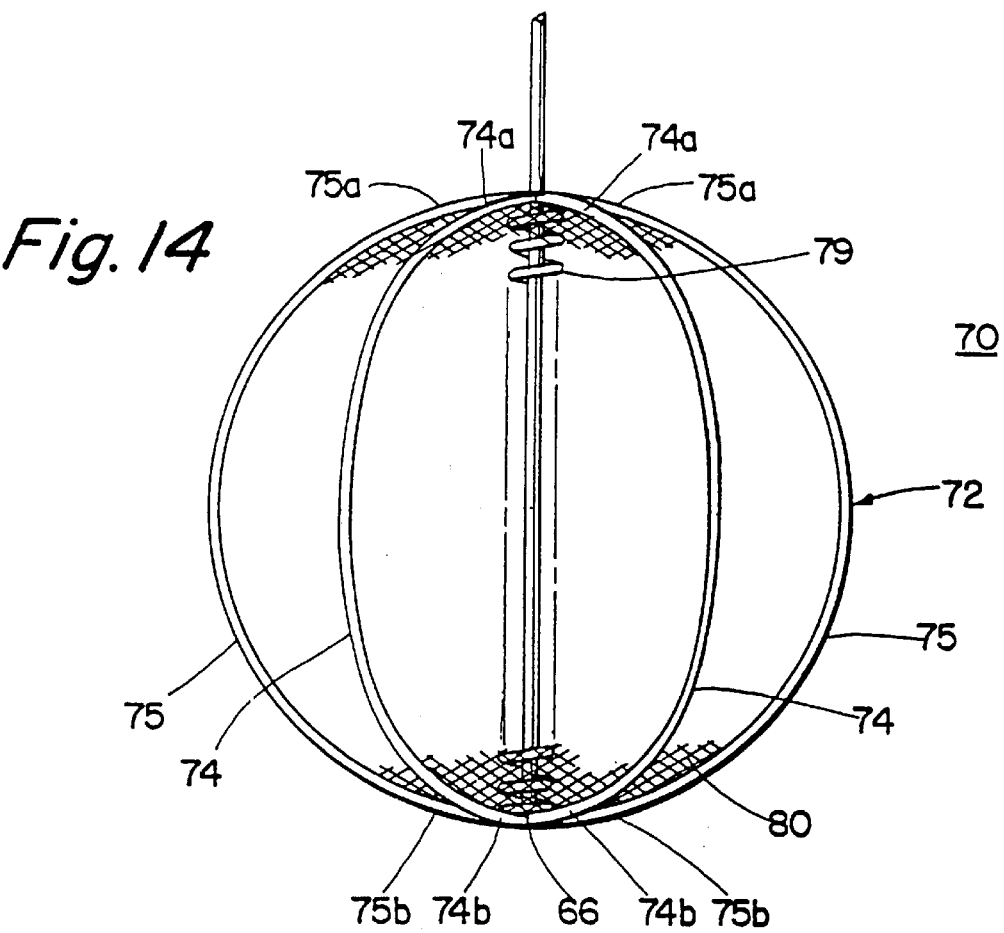
FIG. 14 is a side view of a spring-activated expansion frame for an expandable filter device.

As shown in FIG. 14, a spring 79 may be provided between the ends 74a, 75a, 74b, 75b of the struts 74, 75. The spring 79 may be compressed by use of a control wire or like apparatus (not shown) to expand the struts 74, 75 to the enlarged condition. When the filter 70 is to be removed, the spring 79 biases the expansion frame 72 to compress the struts 74, 75 to the contracted condition, entrapping embolic material in the mesh 80.

Alternatively, the open end struts 75 may themselves be provided from compressed springs (not shown), thus biasing them to the contracted condition. Such struts may conform more easily to the shape of the wall of the vessel than solid struts.

Generally, as shown in FIG. 19, the cannula 20 and the modular filter device 40 are furnished separately, although alternatively, the device 10 may be provided preassembled as in FIG. 18. The cartridge 42 and filter device 60, however, are generally pre-assembled, thereby providing the modular filter cartridge 40. This is accomplished by compressing the expandable filter (not shown) and directing the distal end (not shown) of the shaft 62 into the channel (not shown) in the cartridge 42, such that the expansion frame and mesh (not shown) are substantially contained within the cartridge 42.

Prior to use, the modular filter cartridge 40 may be inserted into the side port 32 of the cannula 20, as shown in FIG. 18. The distal end 24 of the cannula 20 may then be introduced into a blood vessel 100, such as the aorta, using conventional procedures, as illustrated in FIGS. 4 and 5, allowing blood to be carried into the vessel 100 from the lumen 26. Once the distal end 24 of the cannula 20 is in position within the vessel 100 and the cannula 20 is secured to the patient, such as using the suture flange 30, the expandable filter may be deployed into the vessel, as shown in FIGS. 16 and 17.

As shown in FIGS. 2 and 3, the shaft 62 of the filter device 60 may be directed distally to deploy the expandable filter 70 on its distal end 66. This causes the expandable filter 70 to pass through the passage 34, through the lumen 26 in the cannula 20 and to exit the distal end 24 of the cannula 20 either through the outlet 28 (FIG. 2) or the filter outlet 29 (FIG. 3), into the vessel (not shown in FIGS. 2 and 3). The expansion frame 72 may open automatically, or may be mechanically expanded to its enlarged condition, thereby opening the filter mesh 80 substantially across the vessel and capturing any embolic material traveling therethrough. At any time, the expansion frame 72 may be closed to its contracted condition, entrapping any embolic material captured by the mesh 80, and the expandable filter 70 withdrawn by pulling proximally on the shaft 62. The expandable filter 70 may be returned into the cartridge 42, which may then be removed from the side port 32. A new modular filter cartridge 40 may be inserted into the side port 32 at any time thereafter, allowing a new expandable filter 70 to be introduced into the vessel, as desired during a surgical procedure.

The modular filter devices and delivery systems described are particularly useful in cardiac surgery. A cannula with modular filter as described above may be deployed within the aorta, for example, upstream of the carotid arteries. The aorta may be clamped upstream of the cannula with modular filter in preparation for a bypass procedure. This clamping generally substantially increases the risk of embolic deposits breaking loose from the wall of the aorta and traveling downstream. With the filter deployed, however, embolic material dislodged during this action may be captured by the filter device. Once the aorta is clamped, the risk of further embolic material being dislodged may be substantially reduced, and so the filter may be removed without substantial concern about embolic material escaping and possibly injuring the patient.

Later in the surgery, a new filter device may be introduced through the cannula into the aorta prior to any action which may substantially increase the risk of further embolic material breaking loose, such as when the aorta is unclamped. Because a new filter may be deployed, any embolic material that is dislodged may be captured more effectively, as opposed to a filter which must remain in the aorta throughout the procedure which may become clogged and impair blood flow through the vessel.

Similarly, the cannula with modular filter may be used to capture embolic material when balloon occlusion is used instead of clamping to close the aorta in bypass procedures. In this procedure, the occlusion balloon may be provided on the same cannula providing the modular filter. Alternatively, a catheter may be introduced into the aorta upstream of the bypass cannula, possibly through a cardioplegic cannula. A filter may be deployed prior to inflation of the occlusion balloon, thereby capturing any embolic material released by the balloon as it engages the walls of the aorta. This procedure may be slightly disfavored, however, since it may reduce the work space available for the bypass cannula and modular filter device.

An important feature is that the filter may be placed immediately downstream of the location which is likely to generate emboli within the bloodstream, such as within the aorta. In addition, a filter device in accordance with the present may more effectively capture embolic material, because the expansion frame in the enlarged substantially engages the wall of the vessel extending the mesh across the vessel, and because the expansion frame may be closed before removal, entrapping the captured material. Thus, the arterial cannula with modular filter device may more effectively capture and remove embolic material released during extended procedures, such as coronary bypass surgery, without clogging the filter and impairing blood flow through the vessel.

In some cases, it may desirable to provide the filter upstream of the cannula outlet through a separate filter outlet, as shown in FIG. 3. For example, this embodiment eliminates filtering the bypass blood which may accelerate clogging of the filter. It also may allow a variety of nozzle designs to be provided on the cannula, without concern that the outlet may be partially obstructed by the shaft of the filter device, as may occur with filters deployed through the cannula outlet.

Certain embodiments of the modular filter apparatus are directed to devices that include adjustable filter frames, where the frame is either self-adjusting, as previously described, or can be adjusted manually by operating a mechanism outside the vessel. Some of these embodiments are depicted in FIGS. 20–37.

FIGS. 20A–H depict an embodiment of a modular filter apparatus 200 for insertion into a hollow vessel insertion device 580 for filtering embolic material from a blood vessel 100 into which the insertion device is introduced. The insertion device 580 is an elongated tube having an outer surface 581, a distal end 582, adapted to enter an artery, a proximal end 583 and a lumen 584 therebetween. The embodiment of FIG. 20 also includes a flange 585 disposed about the distal region. In some embodiments, the hollow vessel insertion device is a cannula, as previously described. In other embodiments, the insertion device is an introducer, hereinafter described. The filter apparatus includes a shaft 62 having a proximal end 221 and a distal end 220. An adjustable filter frame 205 is disposed about the distal end 220 of the shaft 62, and the frame 205 is adjustable between a contracted condition and an enlarged condition. The particular embodiment of FIGS. 20A–H can be externally adjusted. The frame 205 has a diameter 230 and an interior area 232, and a frame sizing mechanism 210 associated with the frame. In the case of this embodiment, the frame sizing mechanism includes a center hinge 234, which in this depiction is a thinner section of frame material, together with a proximal region 238 that includes two thin frame areas and two frame arms 240 that protrude out of the vessel and may be externally manipulated to cause the frame to enlarge and contract to fit the vessel size. In certain embodiments, the frame and mesh coupled thereto are demountable from the shaft. The embodiment of FIGS. 20A–H also includes an expandable sheet 245 coupled to a portion of the proximal region of the frame 238. The sheet stretches and contracts as the frame is enlarged or contracted. The apparatus also includes a filter mesh 80 coupled to the frame for capturing embolic material. The modular filter apparatus is removably insertable into a hollow vessel insertion device 580, and upon insertion through the device and into the vessel 100, the frame sizing mechanism is operated to adjust the diameter of the filter frame to conform to the inner lumen of the vessel.

FIGS. 20A–F show the insertion of the filter apparatus into the insertion device 580. First the frame 205 is pinched along the sides 231, as shown in FIG. 20B, until the center hinge 234 buckles forming a point as shown in FIG. 20C. The frame 205 is then inserted into the insertion device 580, as shown in FIG. 20D. When the proximal region 238 of the frame has cleared the insertion device and has entered the vessel, the frame enlarges as shown in FIG. 20E. If the frame diameter has not conformed to the vessel size, as shown in FIG. 20E, and needs to enlarge, the arms 240 of the frame may be externally manipulated by pushing them into the insertion device. As shown in FIG. 20F, the frame then further enlarges and the expandable sheet 245 in the proximal region 238 stretches as the frame fully conforms to the vessel size. Conversely, if the frame were too large, the arms 240 of the frame could be pulled thus contracting the frame size to fit the vessel.

Figure 21B:
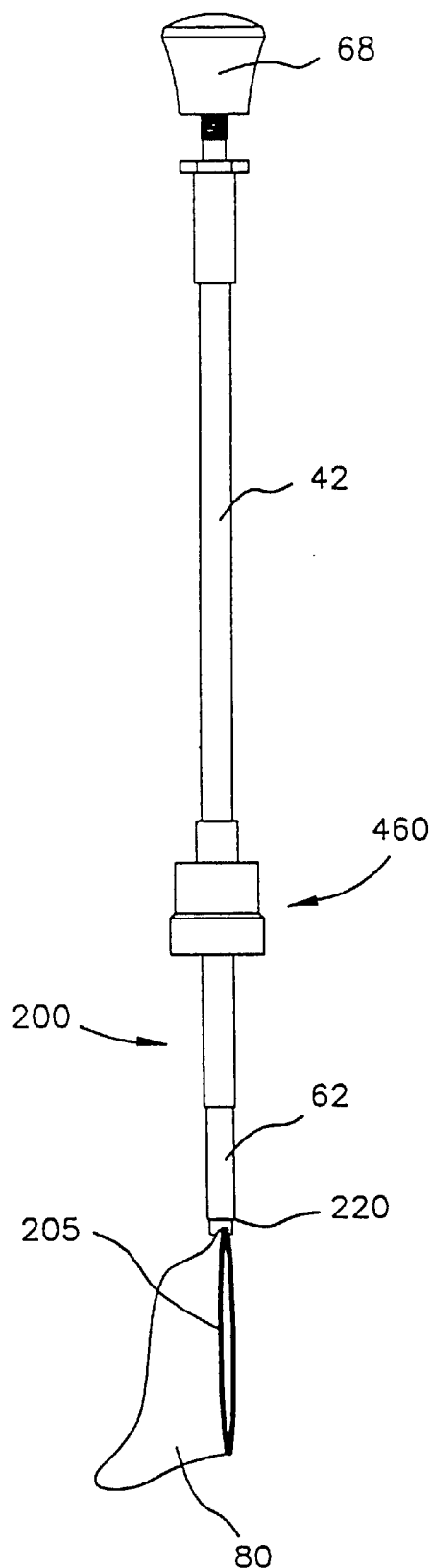
FIG. 21B is a lateral elevation of the embodiment of FIG. 21A.
Figure 21A:
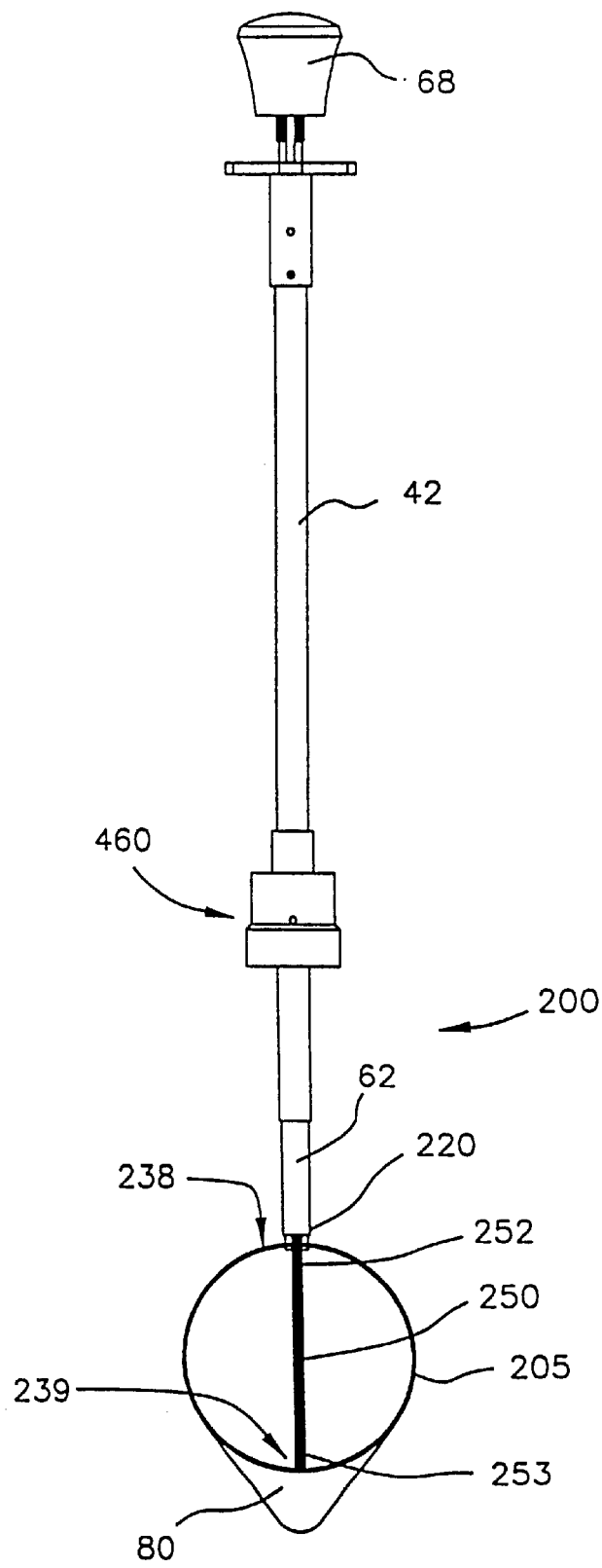
FIG. 21A is a top elevation of an embodiment with a slideable cantilever beam and a filter cartridge.
Figures 21C, 21D, 21E:
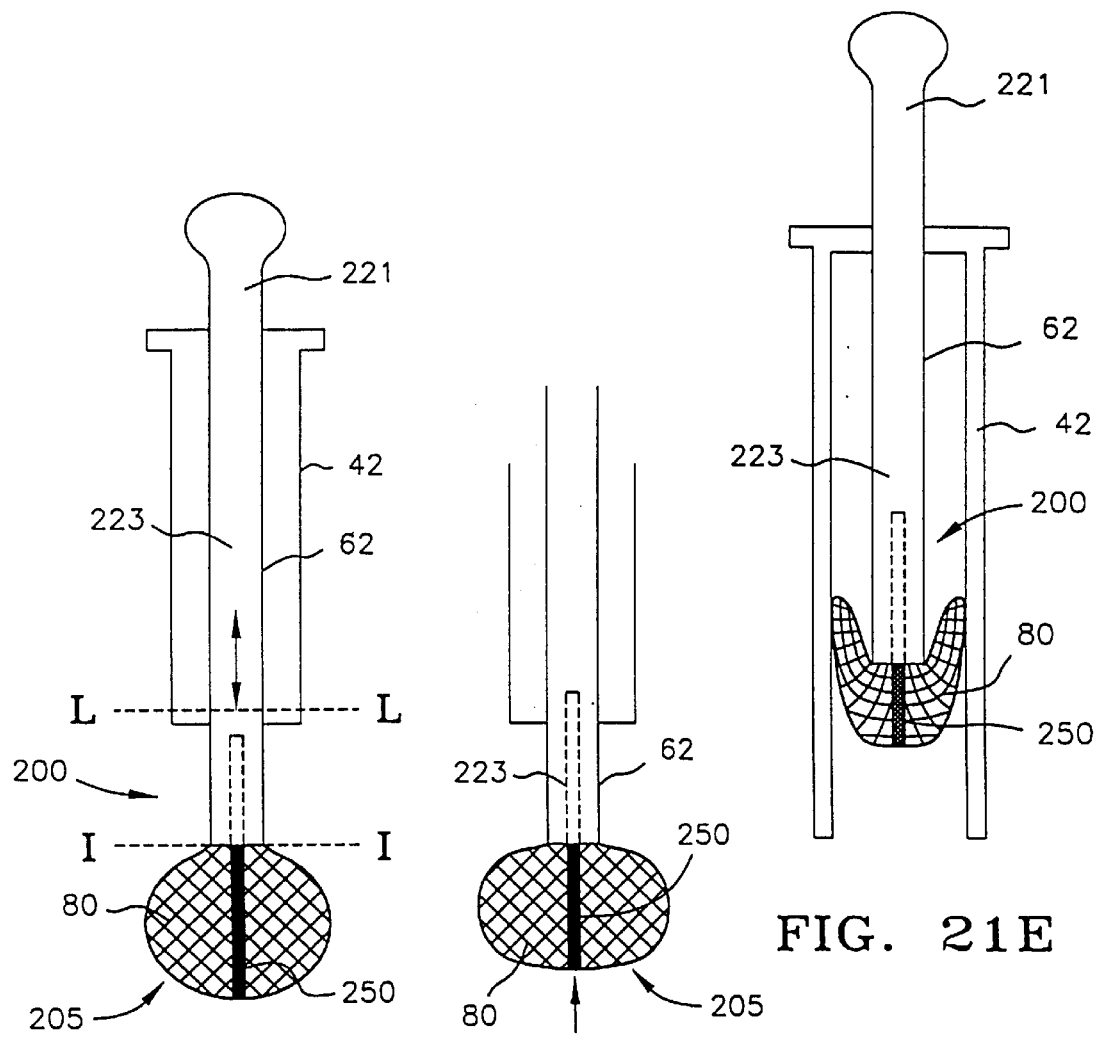
FIGS. 21C–H show the distal region of the embodiment of FIG. 21A as the device withdraws into and protrudes out of a filter cartridge.
Figure 21F:
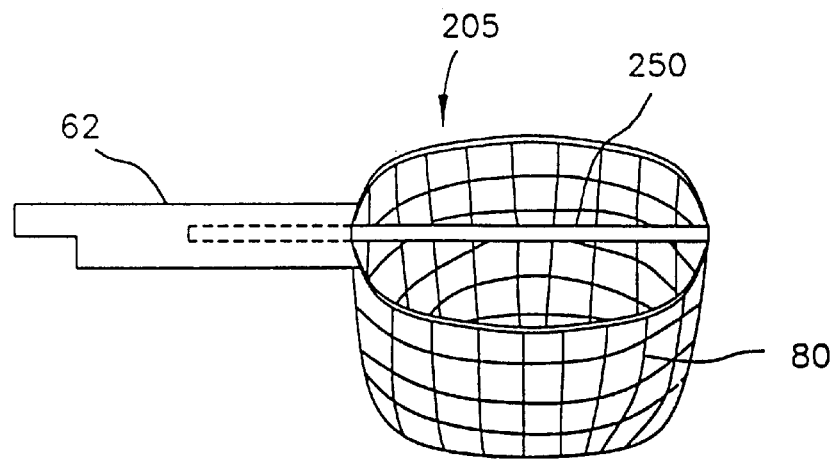
Figure 21G:
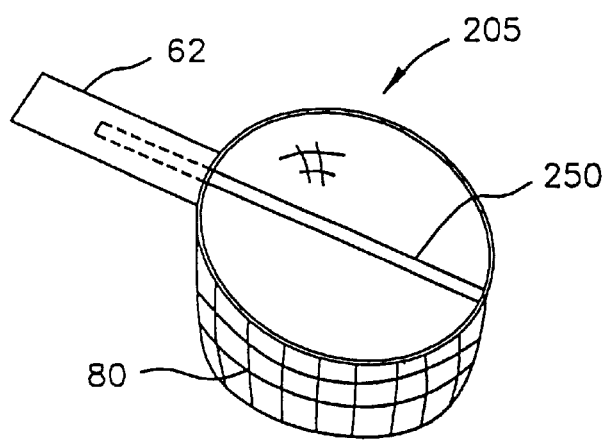
Figure 21H:
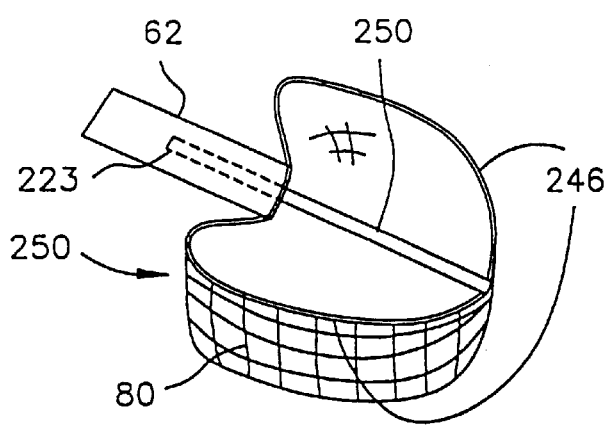
Figures 21I, 21J:
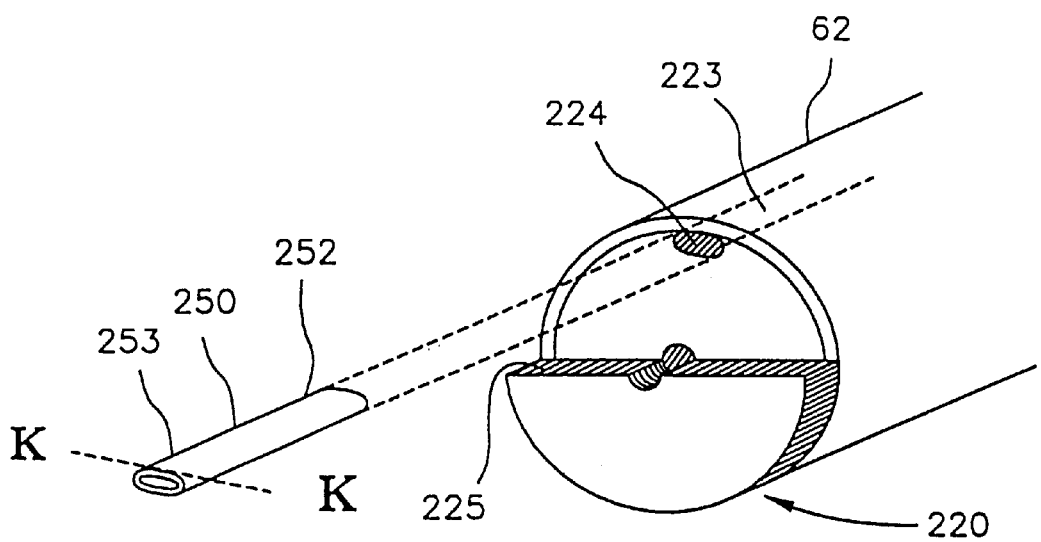
FIG. 21I shows a perspective elevation of an exploded view of a detail of the device of FIG. 21C along line 1—1.
FIG. 21J is a detail of the cantilever beam of the embodiment of FIG. 21 A.
Figures 21K, 21L:
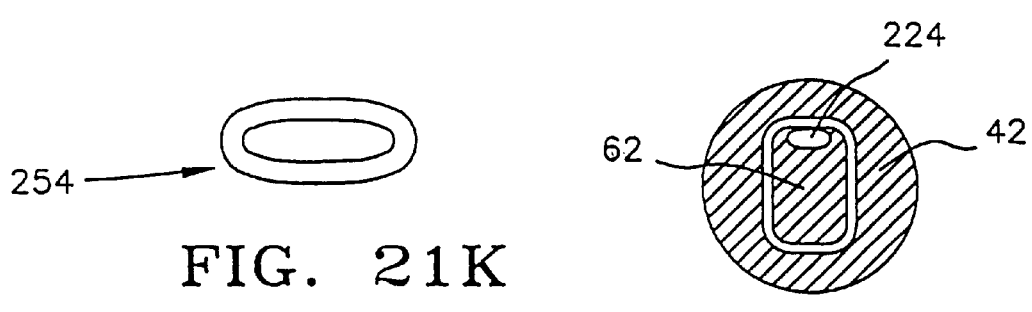
FIG. 21K is an end view of the cantilever beam of the device of FIG. 21J along line K—K.
FIG. 21L is a cross-section of the embodiment of FIG. 21C along line L—L.

FIGS. 21A–L show an embodiment of a modular filter apparatus that also includes a tubular cartridge 42 for receiving the distal end of the filter shaft 62 and protecting the adjustable frame 205 and mesh 80. The cartridge is removably insertable into an insertion device (not shown). In certain embodiments, the tubular cartridge 42 provides a hemostatic seal or one-way valve between the filter shaft 62 and the insertion device into which the cartridge may be inserted. In some embodiments, the cross-section of the shaft 62 is non-round and the lumen in the cartridge 42 conforms to the shape of the shaft 62, as shown in FIG. 21L. Such a configuration inhibits rotation of the shaft in the cartridge thereby fixing alignment of the frame in an orientation determinable from the orientation of the cartridge. The embodiments shown in FIGS. 21A and B also include a distal region 460 that can include an indexing or indexing/locking mechanism as hereinafter described in more detail.

Certain embodiments of the modular filter apparatus, as depicted in FIGS. 21, 25, 26, 33 and 34, include a cantilever beam configuration to help stabilize the filter frame and, in some cases, to assist in frame sizing. As shown in FIGS. 21A–L, these devices have a frame 205 with a proximal region 238, a distal region 239 and a cantilever beam 250 that has a proximal end 252, a distal end 253 and a cross-section 254. The distal end 253 of the beam 250 is associated with the distal region 239 of the frame 205, and the proximal end 252 of the beam is associated with the distal end 220 of the filter shaft 62. In certain embodiments of the cantilever beam configuration, as shown in FIGS. 25A–C and FIG. 26A, the proximal end of the beam is continuous with the distal end of the shaft. However, in the embodiment of FIGS. 21A–L, the proximal end 252 of the beam is not continuous with the distal end 220 of the shaft 62. In some embodiments, the proximal region of the frame is associated with the distal end of the shaft, and in other embodiments, the proximal region of the frame is associated with the proximal end of the beam. In the embodiment of FIGS. 21A–L, the proximal region 238 of the frame is coupled to the distal end 220 of the shaft 62, and the distal end 253 of the beam is coupled to the distal region 239 of the frame. In certain embodiments, the proximal end of the cantilever beam is coupled to the distal end of the filter shaft. In other embodiments, such as depicted in FIGS. 21A–L, the filter shaft 62 has a lumen 223 that extends from the proximal end of the shaft (not shown) to an opening 224 in the distal end of the shaft. The proximal end 252 of the cantilever beam 250 is slideably insertable into the distal opening 224 of the shaft 62. The slideably insertable cantilever beam 250 is also part of the frame sizing mechanism.

The embodiment of FIGS. 21A–L also has a frame anti-rotating mechanism to help stabilize the orientation of the frame relative to the shaft and thus inhibit rocking of the frame or frame migration along the vessel. In one embodiment, as shown in FIGS. 21I–21K, the cross-section 254 of the cantilever beam 250 is non-round, in this case oval, and the opening 224 in the distal end of the filter shaft is of a shape that conforms to the shape of the cross-section 254 of the cantilever beam. In other embodiments, the cantilever beam cross-section may be other shapes such as rectangular, triangular or the like. The embodiment of FIG. 21I also has a shelf 225 on the distal end 220 of the shaft to support the proximal region 238 of the frame to further inhibit rotation of the frame on the shaft. During use, the shape of the opening 224 in the distal end of the filter shaft 62, the shape of the cross-section 254 of the beam 250, and in the case of the embodiment of FIG. 21I, the shelf 225 all inhibit rotation of the beam 250 in the lumen 223 of the shaft and thus inhibit the frame from rotating as it resides in the vessel.

The sequence of FIGS. 21C–21H shows how the modular filter apparatus 200 can be withdrawn into the tubular cartridge 42 and how the slideable cantilever beam 250 assists in sizing the frame to the vessel. FIG. 21C shows the frame 205 in its fully enlarged condition. In FIG. 21D, pressure has been applied to the distal region 239 of the frame, and the beam 250 has started to slide into the lumen 223 of the shaft 62. In FIG. 21E, the proximal end of the shaft 221 has been pulled and the modular filter apparatus 200 has been withdrawn into the filter cartridge 42. FIG. 21H shows how the frame 205 may adjust to fit a smaller vessel by slideable insertion of the beam 250 into the lumen 223 of the shaft 62. The segments 246 of the frame on either side of the beam rock upward creating a smaller frame profile capable of fitting a smaller vessel.

Figure 26A:
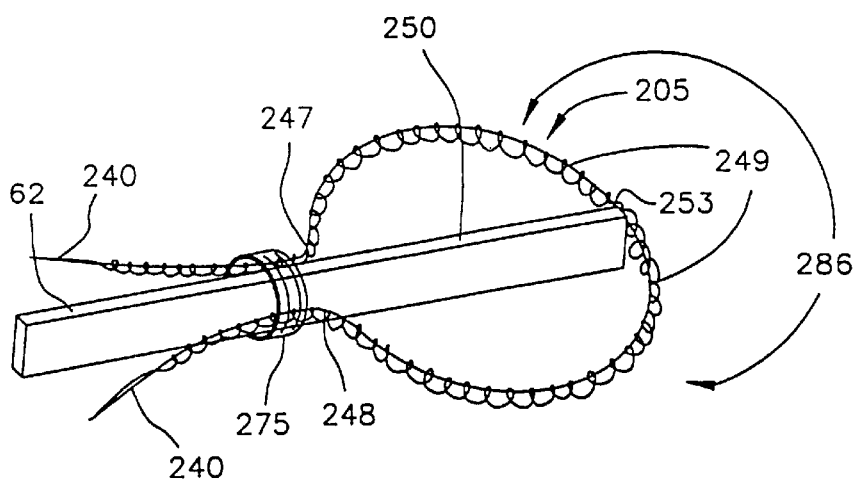
FIG. 26A shows another embodiment of an adjustable spring cable frame suspended from a cantilever beam.

In some embodiments, as shown in FIGS. 25A–C and FIG. 26A, the proximal end of the beam is continuous with the distal end of the shaft. These embodiments include a frame 205 with an open loop 286 with two ends 247, 248 one on each side of the opening of the loop, and a length 249 between the ends. The frame also includes two arms 240, 240, each with a proximal end 270 and a distal end 271. The distal ends 271, 271 of each arm 240, 240 are coupled to an end 247, 248 of the open loop of the frame 205. The distal end 253 of the beam 250 is coupled to the approximate middle of the length 249 of the loop 286 in a cantilever beam configuration with the arms 240, 240 of the frame lying along the shaft 62. During use, the arms 240, 240 may be pushed distally or pulled proximally to adjust the loop 286 of the frame 205 to fit the vessel in which the frame resides. In some embodiments, such as the depiction in FIG. 25C, the arms 240, 240 of the frame are made of less compliant material that the length 249 between the ends 247, 248 of the loop 286. In these embodiments, the relative rigidity of the arms lends support as the arms are pushed or pulled to adjust the size of the loop portion 286 of the frame. In other embodiments, such as the depiction in FIG. 25B, the distal ends 271, 271 of the arms 240, 240 are made of spring cable to create a very flexible area between the arms and the loop portion 286 of the frame which allows a more circular configuration of the loop portion 286 as the arms are pushed pulled to adjust the frame to the vessel. FIG. 26A shows an embodiment where the entire loop portion 286 and the distal portion of the arms 240, 240 are made of spring cable and the embodiment further includes a retaining ring 275 that slideably receives the shaft 62 and the arms 240, 240 of the frame. This retaining ring 275 helps to hold the arms closer to the sides of the shaft for greater control when the arms are pushed or pulled to adjust the size of the frame. In still other embodiments, such as the depiction in FIG. 25A, the arms 240, 240 are made of wire material.

Figure 26B:
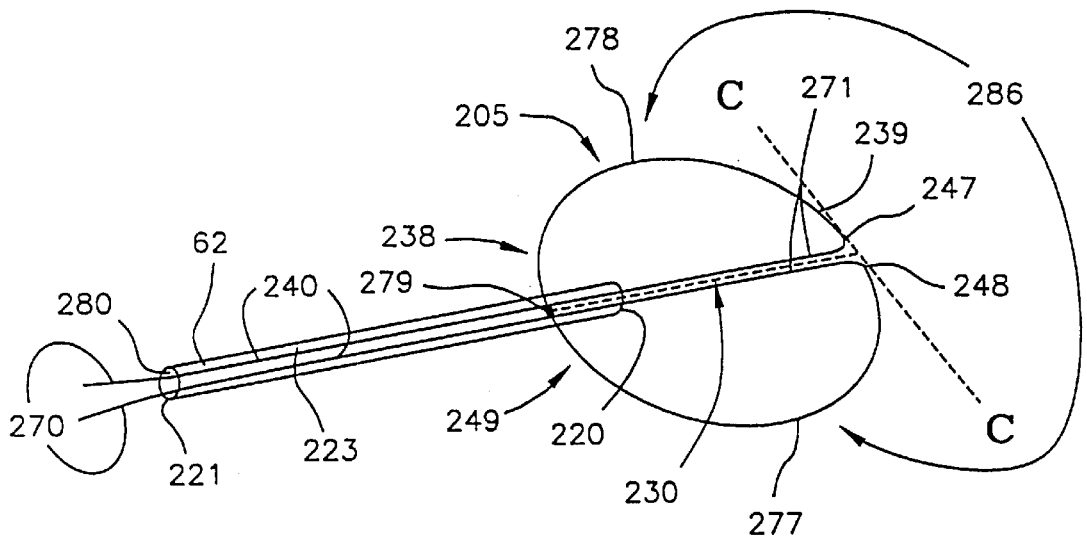
FIG. 26B depicts a "coin-purse" type cantilever beam embodiment.
Figure 26C:
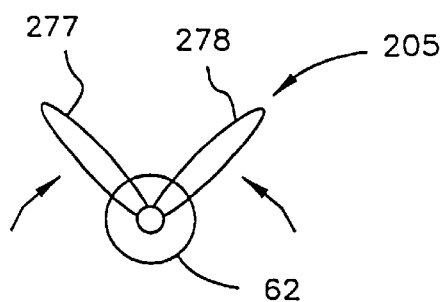
FIG. 26C shows the embodiment of FIG. 26B along line C—C upon closure.

Another embodiment with a type of cantilever configuration is depicted in FIG. 26B–C. The frame 205 of this embodiment has open loop 286 with an end 247, 248 on each side of the opening of the loop and a length 249 between the ends The loop portion 286 of the frame has a proximal region 238 and a distal region 239, a diameter 230 running from the proximal region 238 to the distal region 239, a right segment 277 and a left segment 278 on either side of the diameter 230. The frame 205 also has two arms 240, 240 each with a proximal end 270, 270 and a distal end 271, 271. Each arm distal end 271, 271 is coupled to an end 247, 248 of the loop portion 286 of the frame. The arms 240, 240 extend proximally near the diameter 230 of the loop portion in a cantilever beam configuration. The filter shaft 62 has a distal region 279 pivotally coupled to the proximal region 238 of the loop portion of the frame. The shaft also has a lumen 223 which extends from an opening 280 in the proximal end 221 to an opening (not shown) in the distal end 220. The distal end 220 opening is adapted to slideably receive the proximal ends 270, 270 of the filter arms 240, 240. Both proximal ends 270, 270 the filter arms 240, 240 are slideably insertable into the opening in the distal end 220 of the filter shaft 62, through the lumen 223 of the shaft 62 and out the opening 280 in the shaft proximal end 221. During use, the proximal ends 270, 270 of the arms 240, 240 of the filter frame 205 are adjusted by pulling the ends proximally or pushing them distally causing the diameter 230 of the loop 286 to shorten or lengthen and causing each segment 277, 278 of the loop to pivot radially about the shaft 62 to adjust to the size of the vessel in which the frame resides. FIG. 26C is an end view of the embodiment of FIG. 26B along line C—C, showing the effect of pulling on the arms 240, causing the right and left segments 277, 278 of the frame 205 to pivot radially toward one another in a coin-purse closure action.

Figure 22B:
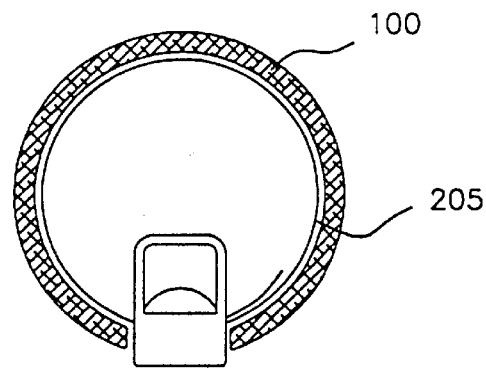
FIG. 22B shows the adjustable filter of the device of FIG. 22A expanded inside the lumen of a vessel.
Figure 22A:
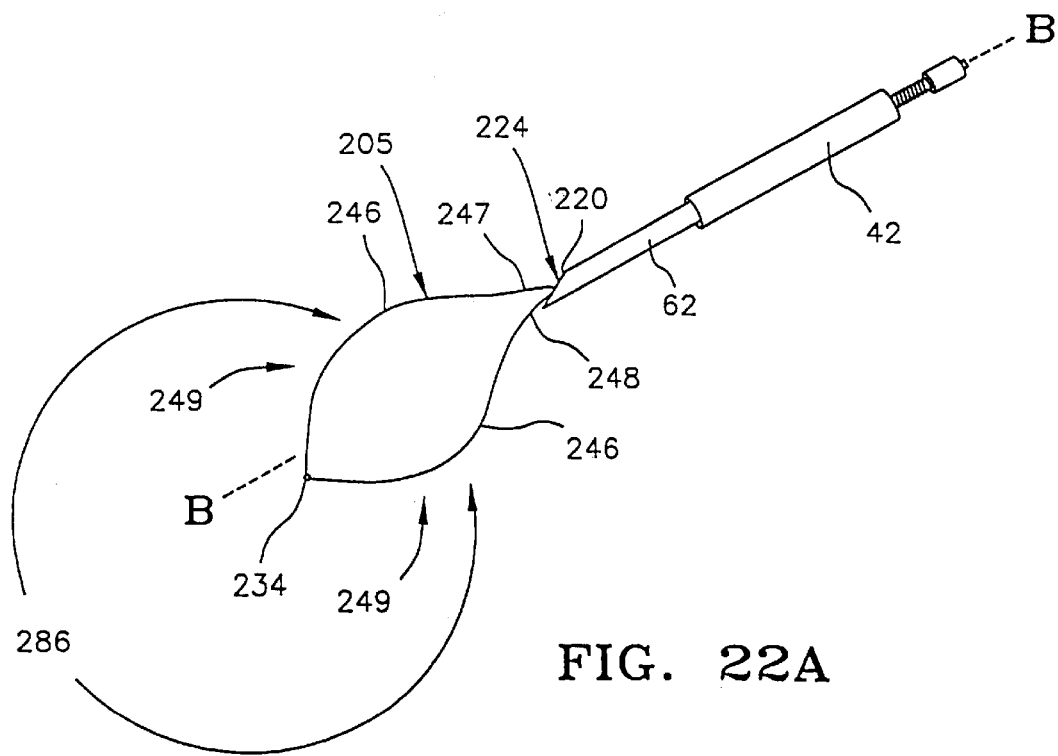
FIG. 22A shows a top elevation of a center-hinged adjustable filter device.

Other loop frames that are not cantilever configurations are also described. The embodiment of FIGS. 22A–B is a loop frame where the loop 286 has a first end 247 and a second end 248 and length 249 between the two ends. As described previously, the shaft 62 has a lumen (not shown) which extends from an opening in the proximal end (not shown) to an opening in the distal end 224 that is adapted to slideably receive the two ends 247, 248 of the loop frame 205. Both ends 247, 248 of the loop frame are slideably insertable into the opening 224 in the distal end of the filter shaft 62, through the lumen of the shaft and out the opening in the proximal end (not shown). During use, the ends of the filter frame are adjusted by pulling them proximally or pushing them distally causing the frame to adjust to the size of the vessel in which the frame resides.

The embodiment of FIGS. 22A–B also includes a center hinge 234 in the approximate middle of the length 249 of the loop 286, thus dividing the frame length into two segments 246, 246. During use, each frame segment 246, 246 pivots around the center hinge 234 as the frame ends 247, 248 are pushed or pulled causing the frame 205 to adjust to the size of the vessel in which the frame resides. FIG. 22B shows the loop frame 205 of FIG. 22A, as viewed along axis line B—B, fully enlarged in a vessel 100.

Figure 27:
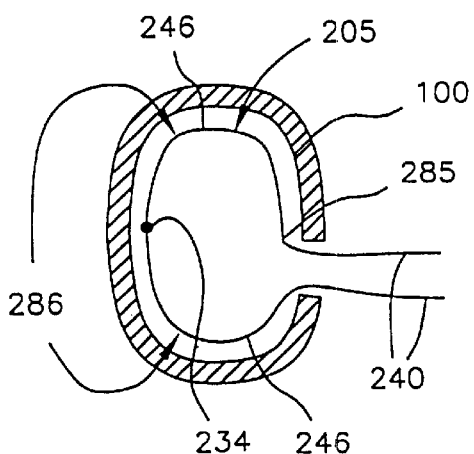
FIG. 27 shows a top elevation of an adjustable frame inside a vessel, where the sizing mechanism is a fixed break point and varying lengths of frame material.

FIG. 27 is also an embodiment of a loop frame with a center hinge 234 in the frame 205. This embodiment also has a kink 285 in the frame in a position where one of the arms 240, 240 connects with the loop 286 portion of the frame. The sizing mechanism includes the kink 285, the hinge 234 and the arms 240, 240. The kink functions as a fixed break point biasing the frame in the direction of the vessel wall as the arms are pushed or pulled to enlarge or contract the frame, and the hinge acts as a pivot point for the segments 246, 246 of the loop on either side of the hinge 234 to rotate.

Figure 23B:
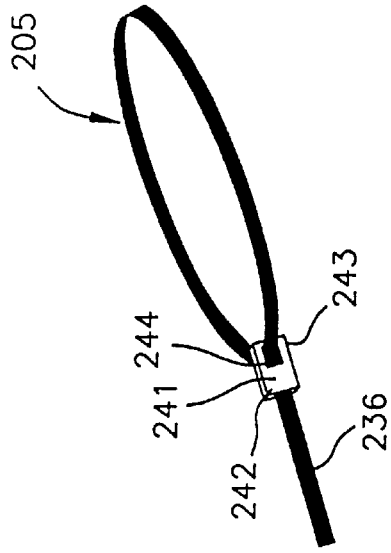
FIG. 23B is a lateral elevation of the device of FIG. 23A.
Figure 23D:
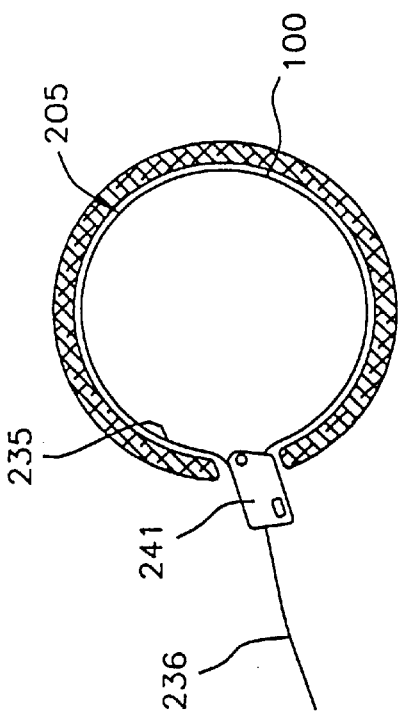
FIGS. 23C–D show the embodiment of FIG. 23A where the adjustable frame conforms to the inner lumen of two vessels of different sizes.
Figure 23A:
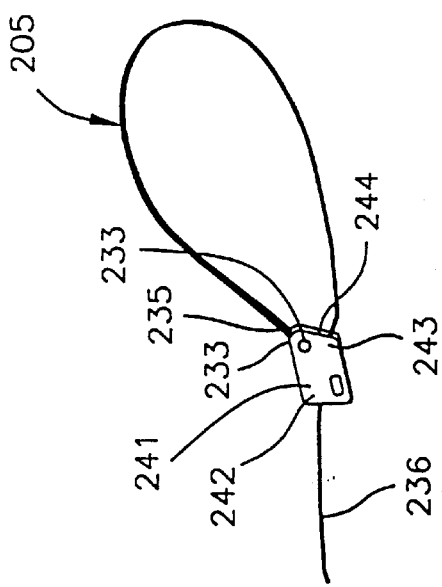
FIG. 23A is a perspective elevation of another embodiment of the adjustable filter frame where the frame sizing mechanism is an adjustable slip joint.
Figure 23C:
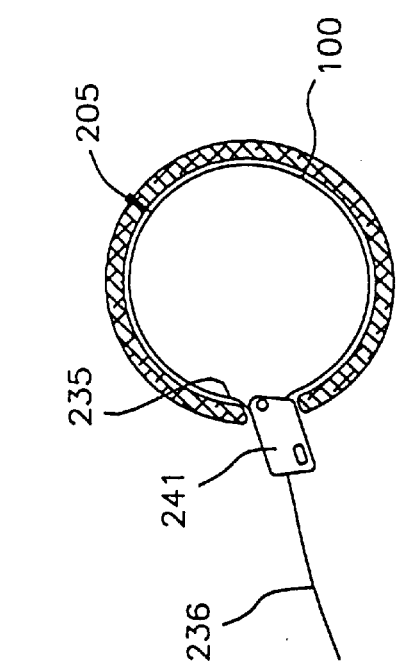

Certain embodiments of the modular filter apparatus include various types of slip joints, some self-adjusting and others that are externally adjustable. FIGS. 23A–D depicts an embodiment of an externally adjustable slip-joint filter frame. The apparatus includes a filter frame 205 that has a fixed end 235 and an adjustable end 236 and a sizing mechanism that includes a slip joint 241, having a proximal end 242 and a distal end 243 and a lumen (not shown) that extends from an opening in the proximal end 244 to an opening in the distal end (not shown). The slip joint 241 is associated with the filter shaft (not shown). The distal end 243 of the slip joint 241 is pivotally coupled 233 to the fixed end of the frame 235. The distal opening 244 of the slip joint 241 is adapted to slideably receive the adjustable end 236 of the frame, which slideably inserts through the opening 244 and is advanced along the shaft of the filter (not shown). During use, the adjustable end 236 of the frame is manually pushed distally or pulled proximally causing the frame to slide into or out of the slip joint 241 and adjust to the size of the inner lumen of the vessel in which the frame resides. FIGS. 23C and 23D show the embodiment of the adjustable slip-joint frame of FIG. 23A in vessels 100 that are of two different diameters.

Figure 24:
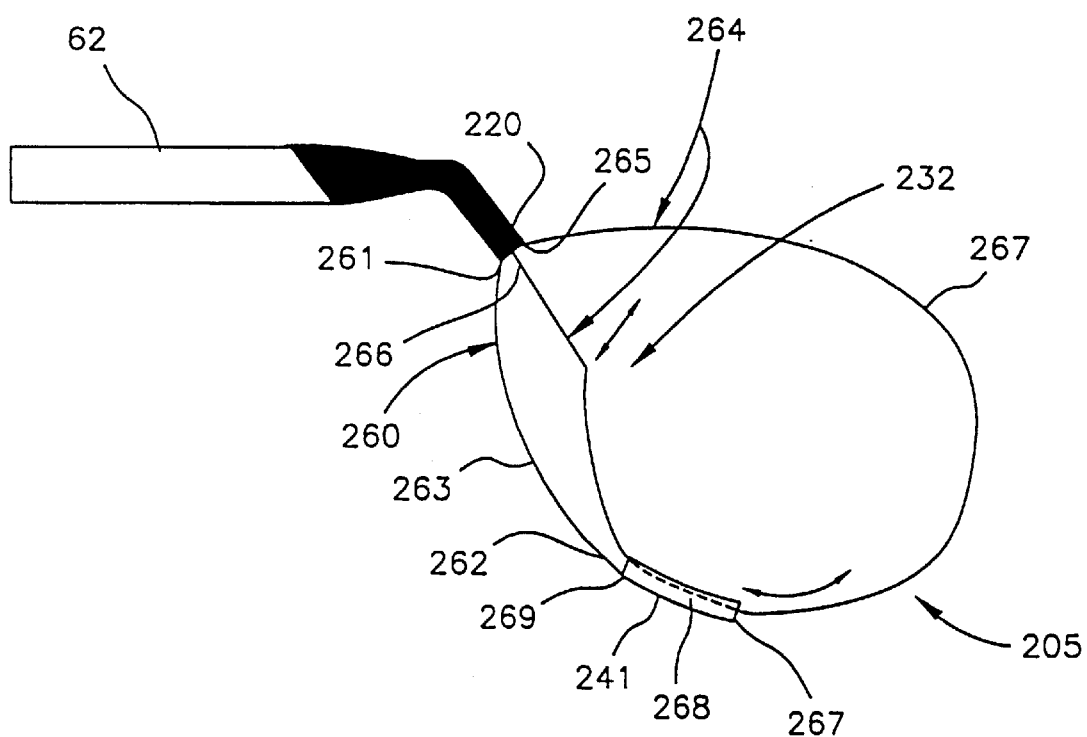
FIG. 24 is another embodiment of a filter device with an adjustable frame where the frame sizing mechanism is a slip joint.
Figure 25A:
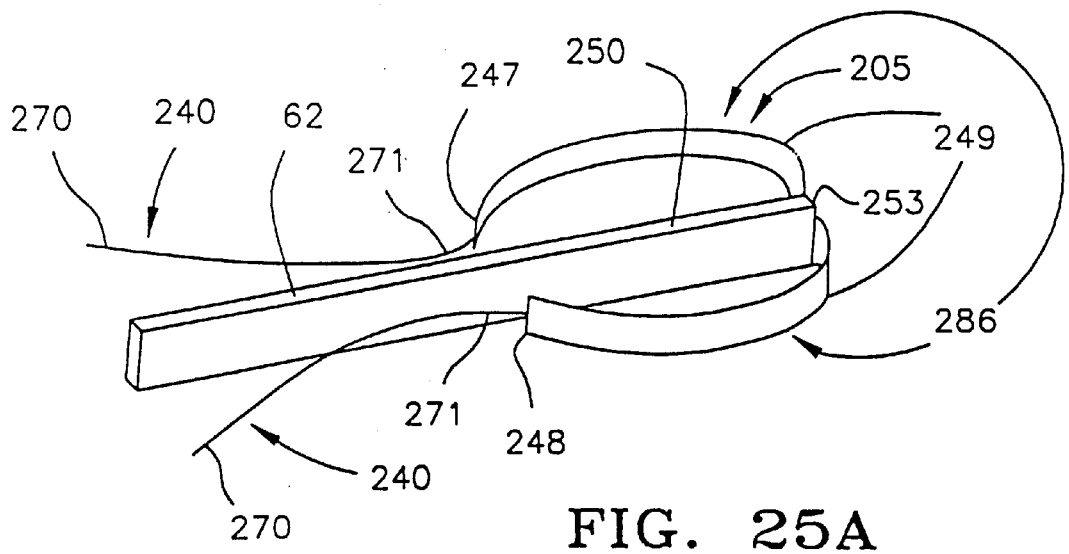
FIGS. 25A–C show various embodiments of a self-adjusting frame suspended from a cantilever beam.
Figure 25B:
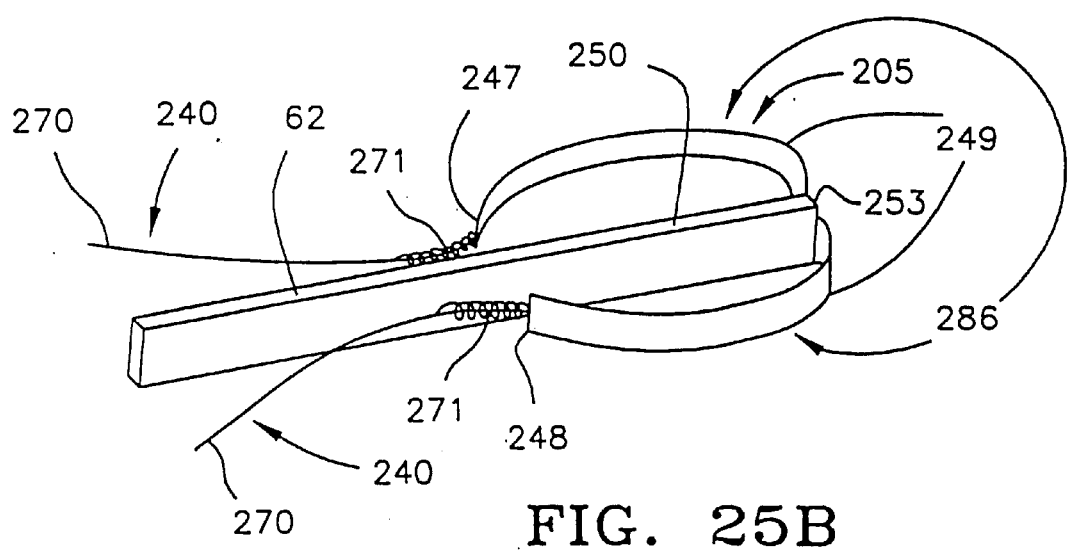
Figure 25C:
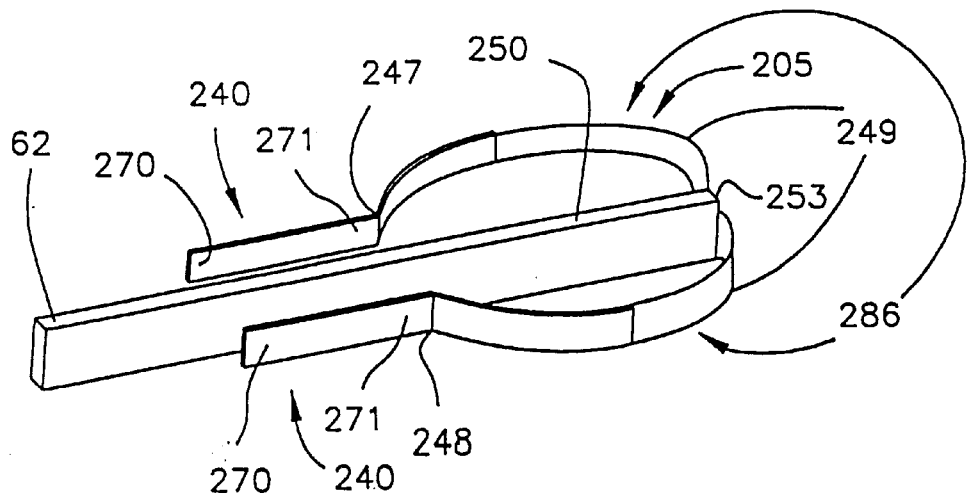

In other embodiments of the modular filter apparatus, the slip joint is self-adjusting. FIG. 24 depicts a self-adjusting modular filter apparatus that includes a filter frame 205 that has a fixed portion 260 and a variable portion 264. The fixed portion 260 has a first end 261 coupled to the distal end of the filter shaft 62, a second end 262 and a first length 263. The variable portion 264 has a first end 265 coupled to the distal end of the shaft, a second end 266 and a second length 267. The second length 267, which is the length of the variable portion is greater than the first length 263, which is the length of the fixed portion. The sizing mechanism further includes a slip joint 241, that has a first end 269, a second end 267 and a lumen 268 that extends from an opening (not shown) in the first end 269 to an opening (not shown) in the second end 267. The first end 269 of the slip joint is coupled to the second end 262 of the fixed portion 263 of the frame. The second end 267 of the slip joint 241 is adapted to slideably receive the second end 266 of the variable portion 264 of the frame 205. The second end 266 of the variable portion 264 is slideably inserted into the opening in the second end 267 of the slip joint 241, through the lumen 268 of the slip joint 241 and out the opening in the first end 269 of the slip joint and is coupled to the distal end 220 of the shaft 62. During use, the variable portion 264 of the frame 205 contracts by sliding into the slip joint 241 and thus buckling into the interior area 232 of the frame or enlarges by sliding out of the slip joint 241 to self-adjust to the size of the inner lumen of the vessel in which the frame resides.

Figure 28A:
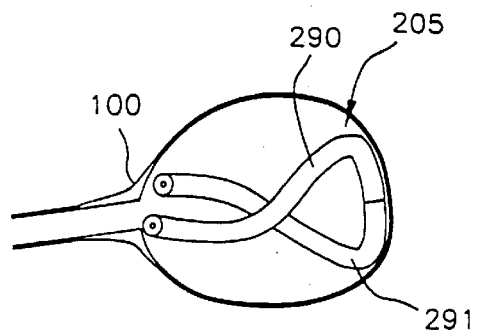
FIGS. 28A–D show an embodiment of an adjustable frame where the sizing mechanism is a segmented frame.
Figure 28B:
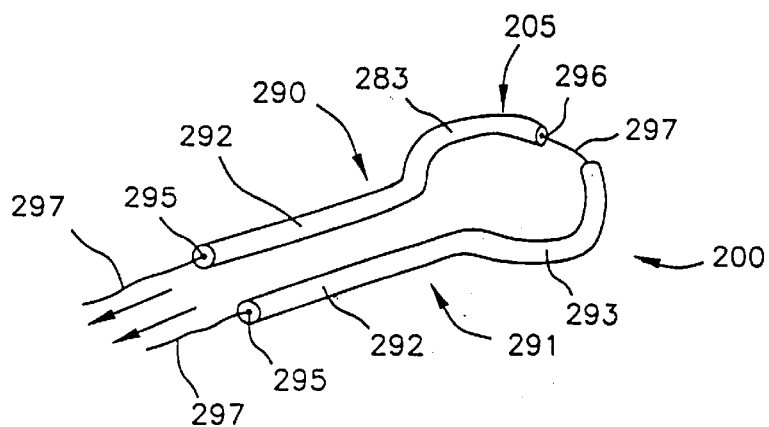
Figure 28D:
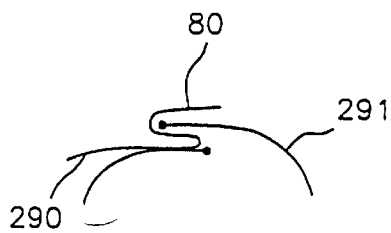
Figure 28C:
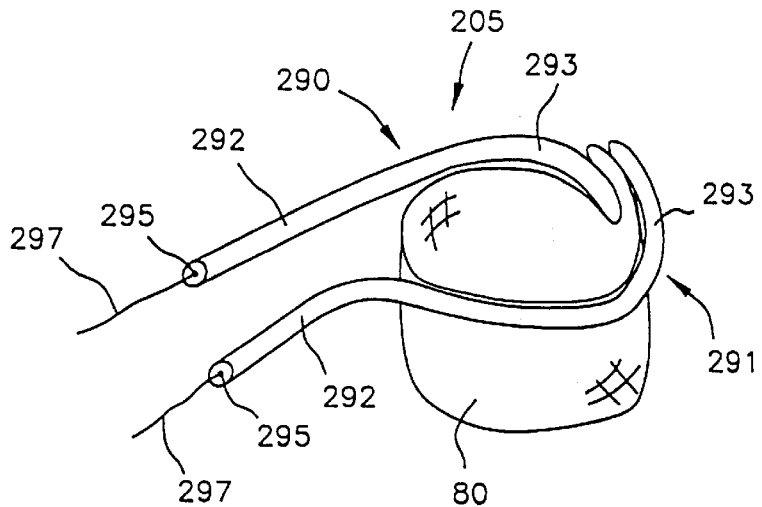

FIGS. 28A–D depict an embodiment of a modular filter apparatus 200 that includes a segmented tubular frame that acts as a frame sizing mechanism for external adjustment of the frame. The frame 205 includes a first segment 291 and a second segment 290, each segment having a relatively straight proximal end 292, an approximately semicircular distal end 293 and a lumen (not shown) that extends from an opening 295 in each proximal end 292 to an opening 296 in each distal end. The apparatus also includes a mesh 80 (not shown in FIGS. 28A and B.) Each segment is oriented so that the straight proximal ends 292 are aligned together and the distal ends 293 curve away from one another forming an approximate circle. The frame 205 also includes a wire 297, as shown in FIG. 28B, slideably inserted into the opening 295 in the proximal end 292 of the first segment 291, out an opening (not shown) in the distal end of the first segment 291, into an opening 296 in the distal end of the second segment 290 and out an opening 295 in the proximal end of the second segment 290. During use, the ends of the wire 297, 297 that lie proximal to the proximal openings 295, 295 of the two segments 290, 291 may be pushed either distally or pulled proximally to push apart or bring together the semicircular ends 293, 293 of the two segments 290, 291 to adjust the loop portion of the frame to fit the vessel in which the frame resides. FIG. 28C shows how the two semicircular ends 293, 293 of the segments 290, 291 may be caused to overlap by externally operating the two relatively straight proximal ends 292, 292 of the frame to contract the frame to conform to the vessel in which the frame resides. FIG. 28C also shows the mesh 80 attached to the segments. FIG. 28D is a top elevation of the embodiment of FIG. 28C showing how the mesh 80 will fold back on itself as the two segments 290, 291 of the frame overlap. FIG. 28A shows the two segments 290, 291 crossed inside a vessel upon insertion, and FIG. 28B shows the effect of externally operating the wires 297 to adjust the segments to their desired positions.

FIG. 29 depicts an embodiment of a loop frame 205 that includes a flat stabilizing plate 300 located in the approximate middle of the loop 286. The plane of the plate is oriented orthogonal to the plane of the frame interior area 232. During use, the stabilizing plate 300 anchors the frame 205 against the inner wall of the vessel in which the frame resides and inhibits frame rocking or migration along the vessel as the frame arms 240, 240 are pushed or pulled to adjust to the size of the frame. FIG. 29A further includes a compliant protective covering 302 over the stabilizing plate.

Figure 31B:
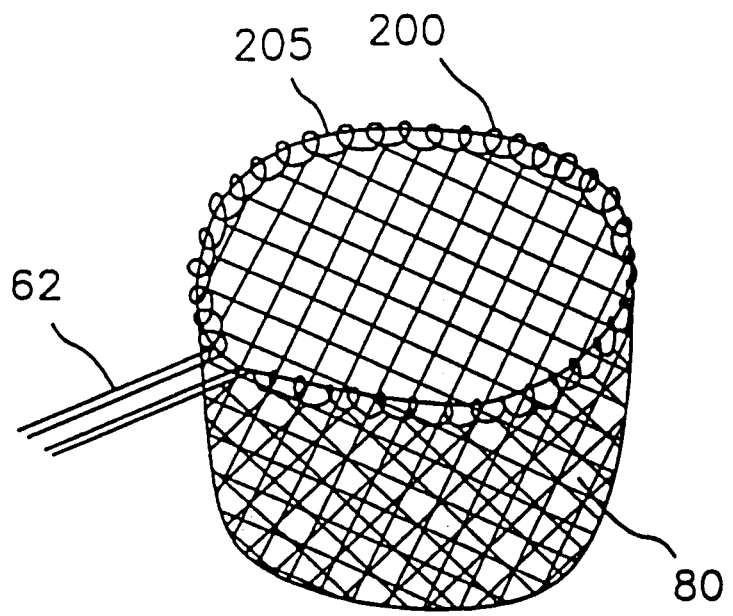
FIG. 31B shows perspective elevation of a filter mesh coupled to a spring coil wound around an adjustable frame.
Figure 31A:
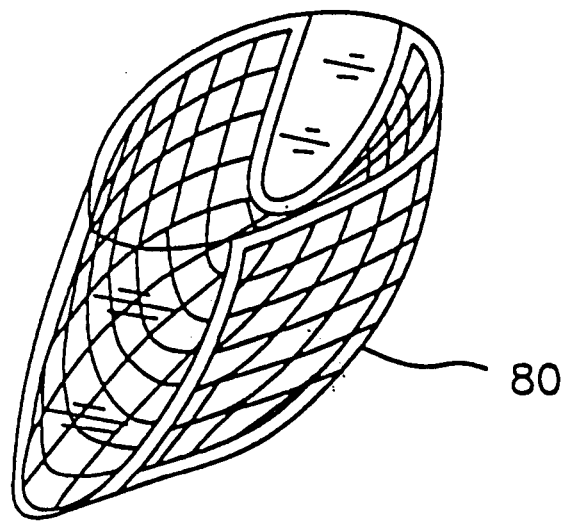
FIG. 31A shows a filter mesh that can be coupled to a filter frame.
Figure 32A:
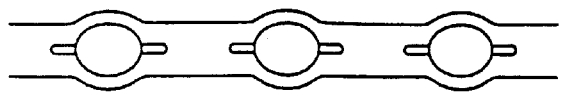
FIGS. 32A–F show details of various embodiments of the adjustable frame material.
Figure 32B:
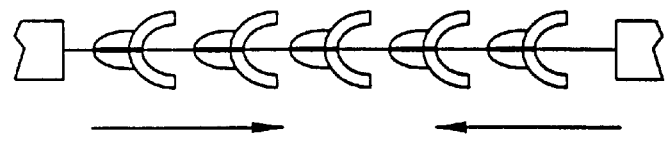
Figure 32C:
Figure 32D:
Figure 32E:
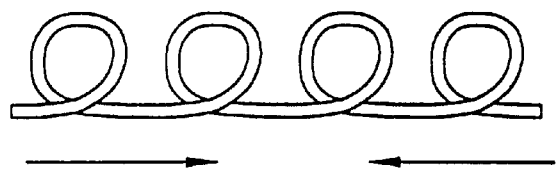
Figure 32F:
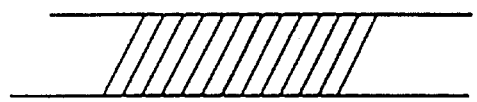

FIG. 30A shows yet another embodiment of a loop frame 205 that has a series of kinks 285 in the frame to enhance flexibility in sizing the frame to the vessel. FIG. 30B is a detail of area B of FIG. 30A. FIG. 31A shows an embodiment of a mesh 80 that may be coupled to a filter frame (not shown). The filter mesh pore size ideally ranges from 40–120μ, but other sizes may be used depending upon the clinical need. The mesh may be plastic fibrous, metal, polyester, nylon, Teflon®, or the like, and may be worn, stamped, etched, laser-machined, molded, spun or layered. FIG. 31B shows another embodiment of a mesh 80 coupled to a spring coil 700 that is wound over a frame 205. The spring coil evenly spaces the mesh over frames of different sizes. FIGS. 32A–F show various embodiments of frame material that may be used in producing the filter frame.

Figure 33A:
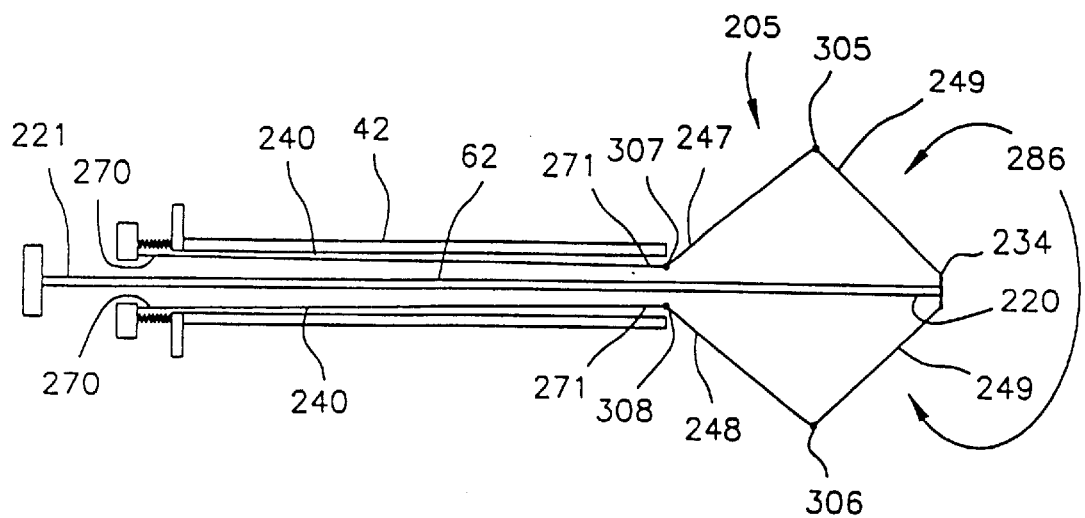
FIG. 33A is a top elevation of a five hinge cantilever beam filter device protruding out the end of a filter cartridge.
Figure 33B:
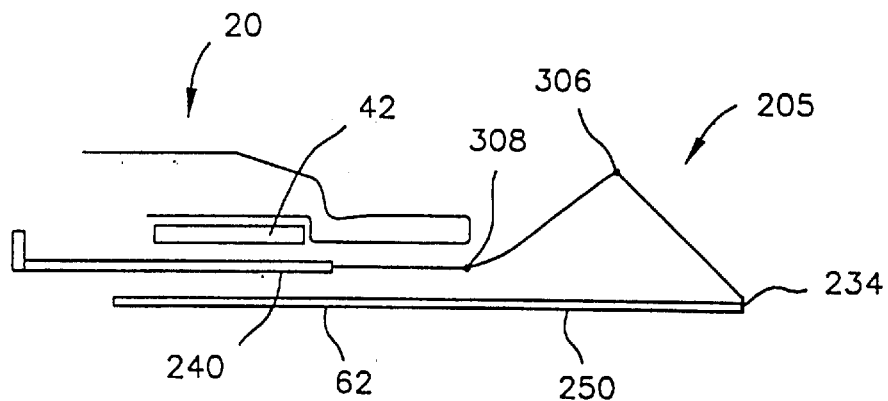
FIG. 33B is a lateral elevation of the embodiment of FIG. 33A.
Figure 33C:
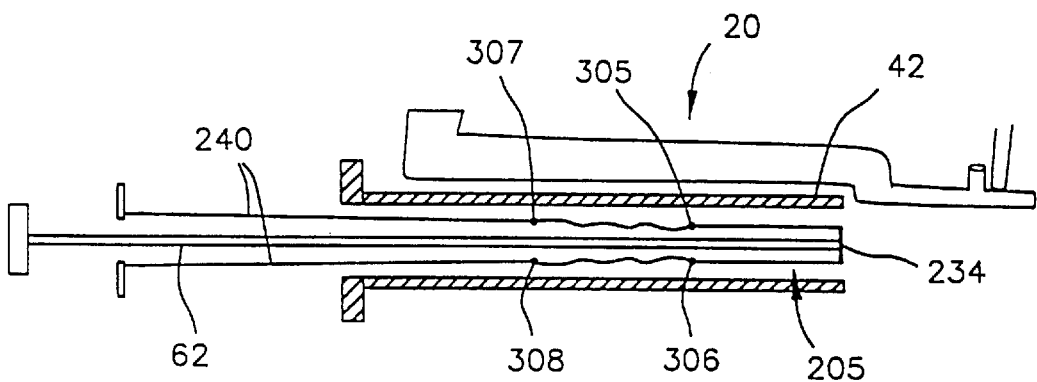
FIG. 33C shows the embodiment of FIG. 33A where the filter device is retracted inside the filter cartridge.

FIGS. 33A–C and 34A–B show an embodiment of a five hinge loop frame in a cantilever beam configuration where the beam 250 is continuous with the shaft 62. The frame 205 includes an open loop 286 with ends 247, 248 on each side of the opening and a length 249 between the ends 247, 248. The frame further includes a hinge 234 in the approximate middle of the length 249 of the loop 286. There are two additional hinges 305, 306, each lying between the center hinge 234 and an end 247, 248 of the loop 286. The frame further includes two arms 240, 240 each with a proximal end 270 and a distal end 271. Each distal end 271, 271 is hinged 307, 308 to an end 247, 248 of the open loop 286. The distal end 220 of the beam 250 is coupled to the center hinge 234 of the loop in a cantilever beam configuration. The arms 240, 240 of the frame 205 lie along, the shaft 62 which is continuous with the beam 250. During use, the arms 240, 240 may be pushed distally or pulled proximally as each of the five hinges 234, 305, 306, 307, 308 flexes or extends to adjust the size of the loop 286 of the frame 205 to fit the vessel in which the frame resides. The apparatus also includes a mesh (not shown). FIG. 33B is a lateral elevation of the embodiment of FIG. 33A, further depicting a cannula 20 and a frame cartridge 42, which are also shown in FIG. 33C. FIG. 33C shows the effect of withdrawing the modular filter frame 205 into the cartridge 42. FIG. 34A shows the effect of pulling on the shaft 62 which causes the side hinges 306, 308 to flex and the frame to decrease in diameter. (The other hinges are not shown.) FIG. 34B shows the effect of pushing on the shaft 62 which causes the hinges 306, 308 to extend and the frame to increase in diameter.

Figure 35:
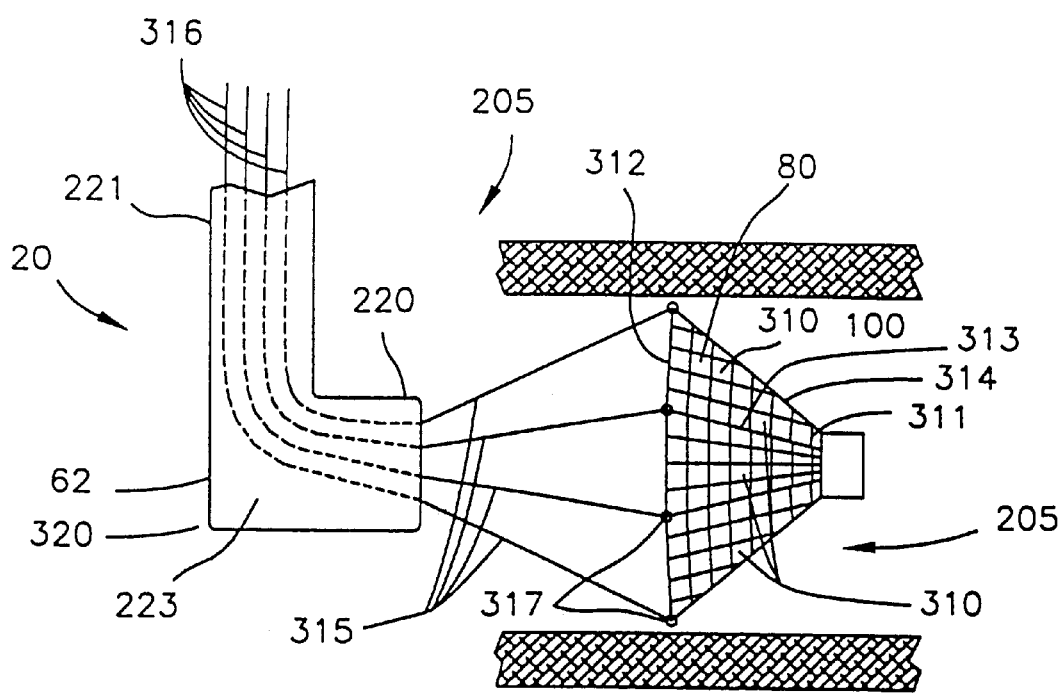
FIG. 35 is a lateral elevation of another embodiment of an adjustable filter device inside a vessel where the filter is deployed at an approximate right angle to the main lumen of the insertion device.

Other embodiments of the modular filter apparatus include basket-type filter configurations as depicted in FIGS. 35 and 36A–C. FIG. 35A depicts an embodiment of a modular filter apparatus 200 that includes a plurality of triangular-shaped filter mesh segments 310, each segment having an apex 311, a base 312, two sides 313, 314 and a mesh 80. The apices 311 of each segment are coupled together and each side 313 of a segment 310 is coupled to a side 314 of an adjacent segment 310 to form a conical configuration adjustable between a collapsed configuration, where the bases are drawn together (not shown), and an enlarged condition, as depicted in FIG. 35, where the bases 312 are flared apart. The filter also includes a plurality of wires 315, each having a proximal end 316 and a distal end 317. Each distal end 317 is coupled to the base 312 of a segment 310. The shaft 62 includes a lumen 223 that extends from an opening in the proximal end 221 to an opening in the distal end 220 and a curved distal region 320. The opening in the distal end 220 is adapted to slideably receive the filter frame 205 in a collapsed condition. The proximal end 316 of each wire is slideably inserted into the opening in the distal end 220 of the shaft 62, through the lumen 223 and out the opening in the proximal end 221 of the shaft. During use, the proximal ends 316 of the wires are pushed distally or pulled proximally to enlarge or contract the filter segments 310 to adjust to the size of the vessel 100 in which the filter resides.

Figure 36C:
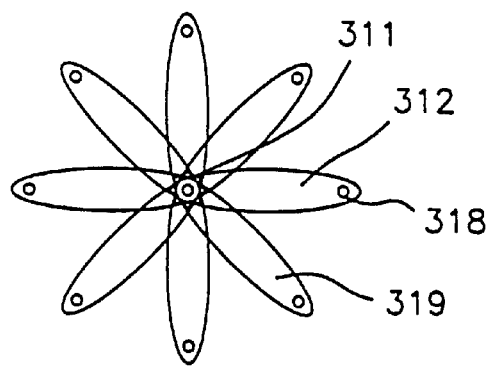
FIG. 36C shows an end elevation of the struts of the frame of the embodiment of FIG. 36A.
Figure 36A:
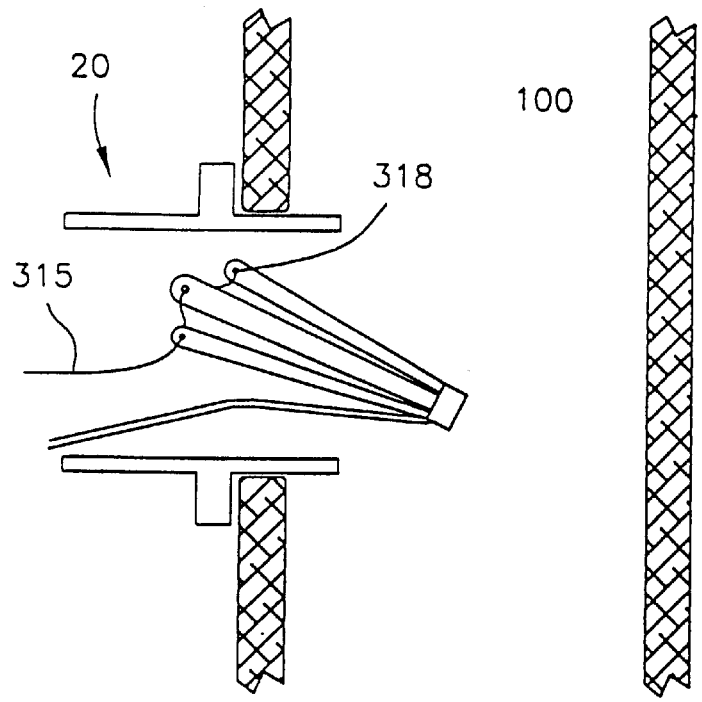
FIGS. 36A–B show lateral elevations of an adjustable frame filter device deployed inside a vessel, where the frame sizing mechanism allows the frame to collapse as it is retracted inside the insertion device.
Figure 36B:
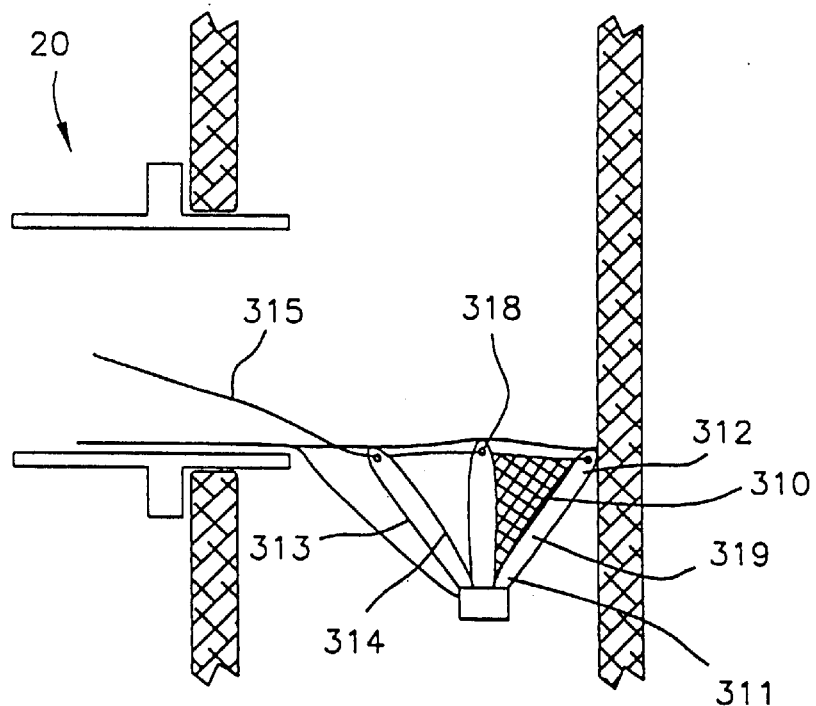

FIGS. 36A–C show another embodiment of the basket configuration of a modular filter apparatus. The filter includes a plurality of triangular-shaped filter mesh segments 310, each segment coupled to a strut 319 that has an apex 311, a base 312 that has a hole 318 in it, and two sides 313, 314. The apices 311 are coupled together and each side 313, 314 is coupled to the adjacent mesh segment 310 to form a conical configuration adjustable between a collapsed configuration, as depicted in FIG. 36A where the bases of the struts are drawn together and an enlarged condition, as depicted in FIG. 36B, where the bases are flared apart. The filter also includes a wire 315 that passes through the hole 318 in each strut. The shaft (not shown) further includes a lumen (not shown) that extends from an opening in the proximal end to an opening in the distal end. The distal opening is adapted to slideably receive the filter in a collapsed condition. Each end of the wire is slideably inserted into the distal region of the shaft, through the lumen of the shaft and out the proximal end. During use, the ends of the wire are pushed distally or pulled proximally to enlarge or contract the mesh segments in order to insert or remove the filter apparatus and also to adjust the apparatus to the size of the vessel in which the filter resides. FIG. 36C depicts an end view of the struts 319 as viewed from the apices 311 of the struts.

Figure 37:
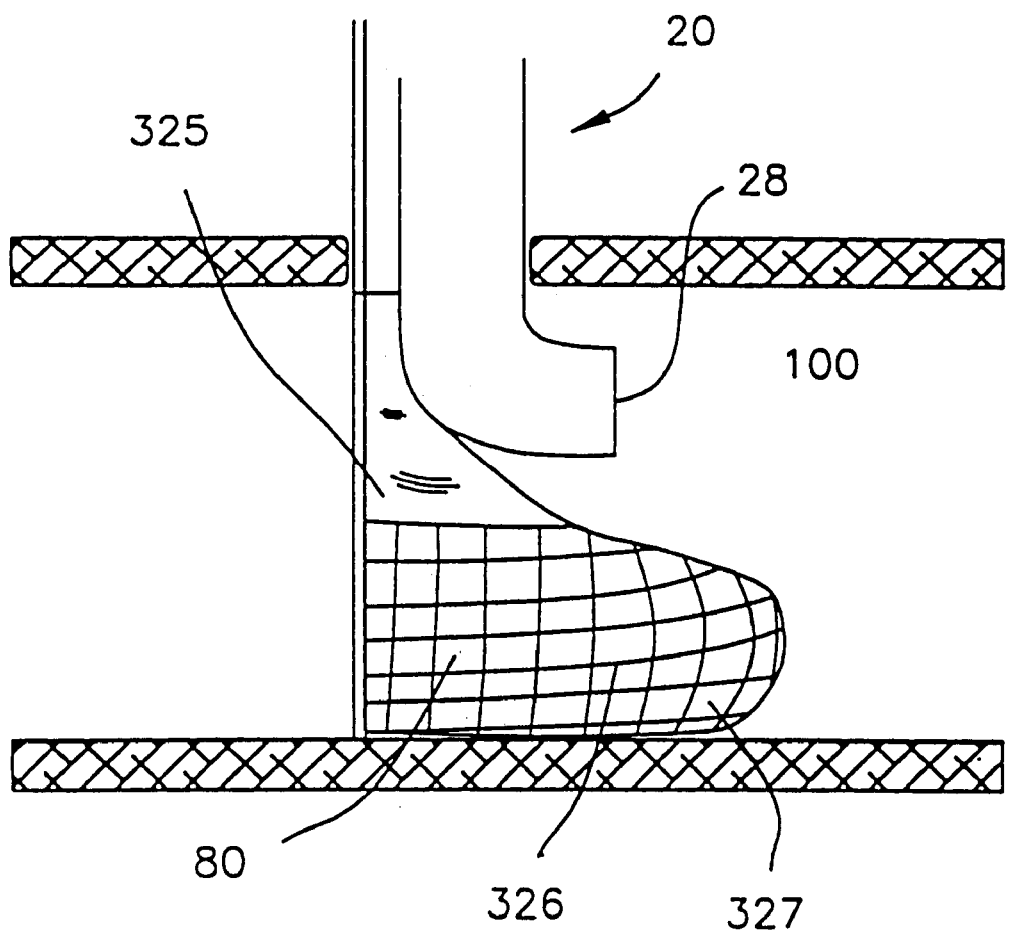
FIG. 37 shows a lateral elevation of an embodiment of a filter device where the upper portion of the filter is less permeable than the lower portion.

In certain embodiments, various portions of the mesh are occluded to guide the trapped embolic material to a predetermined region of the filter for easier removal. Occlusion techniques include reducing the mesh pore size, and thereby the permeability of the mesh, or coating or covering the mesh with a less permeable material. FIG. 37 depicts an embodiment of a mesh that has a generally elongated conical shape with an occluded portion. The mesh 80 has a proximal region 325 and a distal region 326 having an apex 327. The mesh in the proximal region 325 is occluded, causing the mesh in that region to divert blood to the distal more permeable region 326 thereby forcing embolic debris to become trapped in the apex 327 of the mesh.

Figure 38:
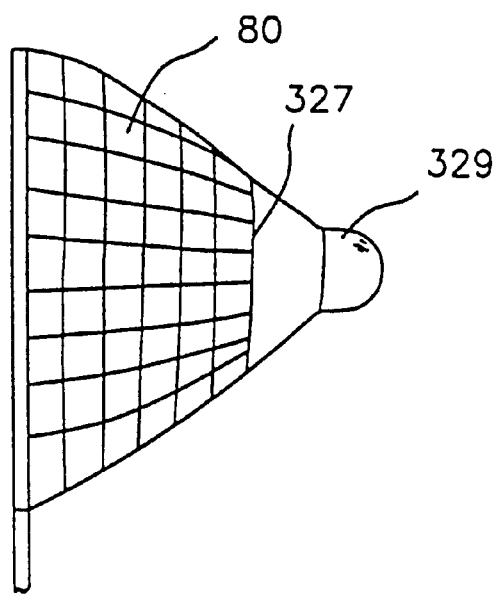
FIG. 38 shows a lateral elevation of an embodiment with a sac coupled to the apex of the filter mesh.

In other embodiments, the mesh of the apex is occluded to enhance trapping the embolic debris. FIG. 38 depicts an embodiment where the mesh is generally conical in shape and has an inner surface (not shown) and an apex 327. The apex 327 is coupled to a mesh-occluded sac 329 that has an inner surface (not shown). During use, embolic debris is trapped in the sac 329 for later removal.

Figure 39A:
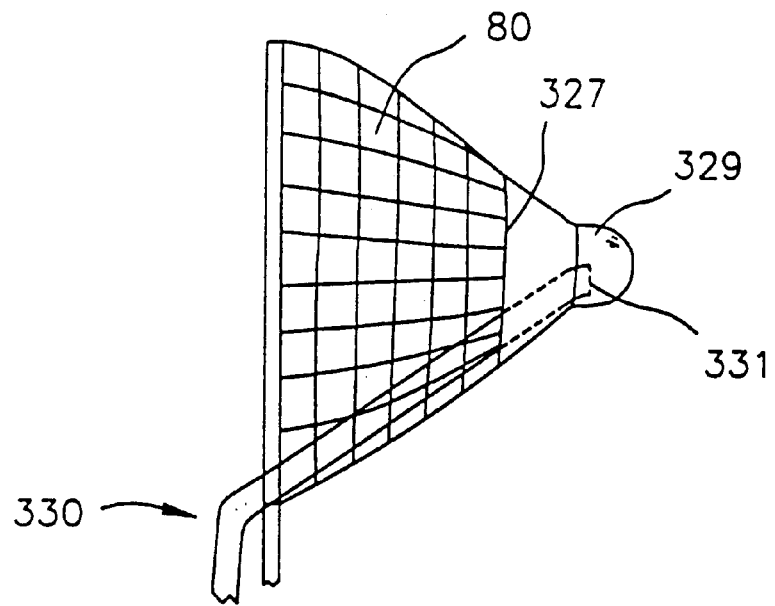
FIG. 39A shows the embodiment of FIG. 38 where the filter device includes an aspiration tube to remove debris from the sac.
Figure 39F:
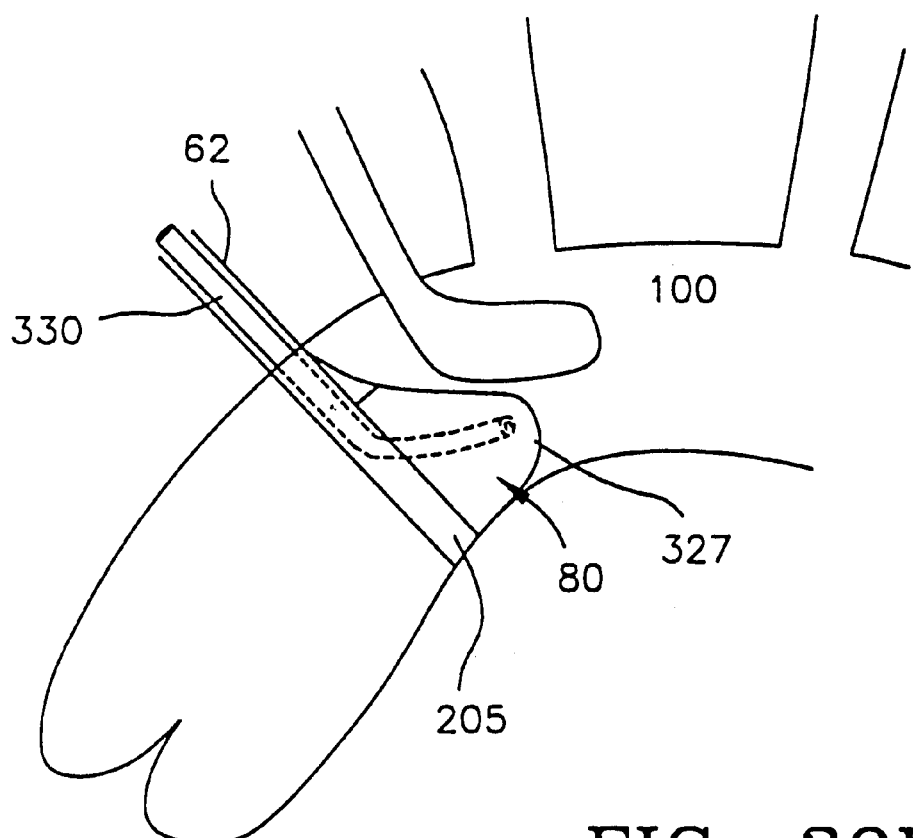
FIG. 39F shows an embodiment of a filter device with an aspiration tube positioned inside the aorta.

Embolic debris can be removed in a number of ways. In some embodiments, the embolic debris is captured in the filter and removed when the filter is removed from the vessel. In other embodiments, a device is inserted into the filter while it is in position in the vessel and the embolic debris is removed through the device. FIGS. 39A–F depict a method of aspirating debris from a filter. The modular filter apparatus includes a filter of the embodiment of FIG. 38 with a mesh occluded sac 329 coupled to the apex 327 of the mesh 80. The apparatus further includes an elongated aspiration tube 330 that has a proximal end 332, a distal end 331 and a lumen 333 extending from an opening in the proximal end 332 to an opening (not shown) in the distal end 331. The proximal end 332 is adapted to connect to an aspiration source (not shown), and the distal end 331 is insertable into the sac 329 or the apex of the filter mesh 80. During use, embolic debris is trapped in the sac 329 of FIG. 38 or the apex of FIG. 37 and is drawn into the aspiration tube 330 and removed from the filter when negative pressure is applied to the proximal end 332 of the tube. FIG. 39C is a detail view of the sac 329 area showing the direction of flow of the embolic debris out of the sac 329 and into the aspiration tube distal end 331. FIG. 39D shows a turbine 335 coupled to the distal end 331 of the aspiration tube to draw out embolic debris from the sac 329. FIG. 39E is a top elevation of an embodiment where the mesh is rotated as shown by the arrow to pull embolic debris into the sac 329 to facilitate its withdrawal into the aspiration tube 330. FIG. 39F shows an embodiment of the filter mesh 80 coupled to a frame 205 and the apparatus placed in a vessel 100 to capture embolic debris. The aspiration tube 330 is shown inserted through a lumen in the filter shaft 62 and into the apex 327 of the mesh 80 to remove debris. The vessel 100 of FIG. 39F is the aorta, although the device is adapted to insert in other vessels as well.

Figure 40A:
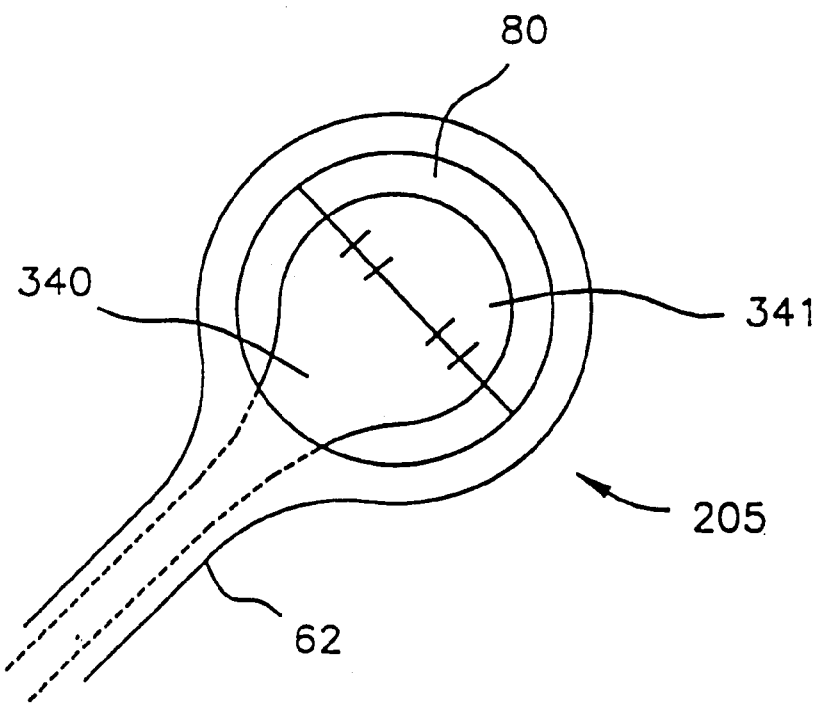
FIG. 40A is a top elevation of an embodiment of a filter device with a scraping device to physically move the debris toward the aspiration tube.
Figure 40B:
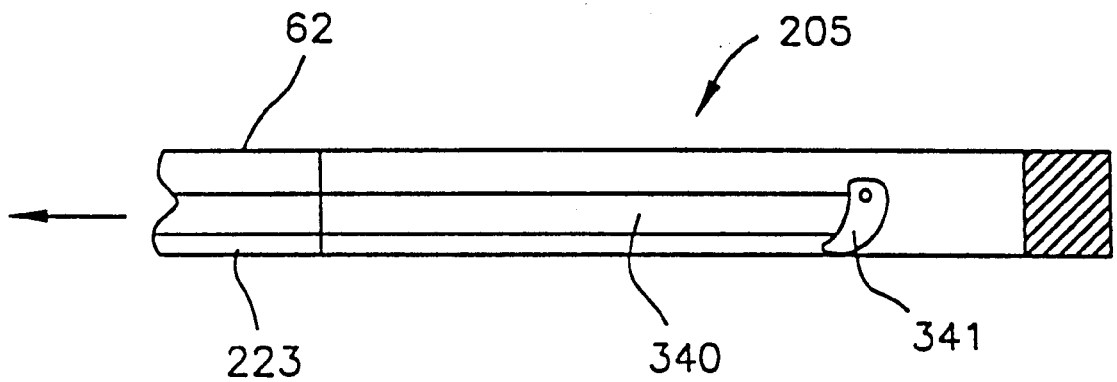
FIG. 40B is a lateral elevation of the device of FIG. 40A.

The embodiment of FIGS. 40A–B includes an elongated scraping device 340 that has a distal end 341 adapted to scrape embolic debris from the mesh 80 toward the distal end of the aspiration tube (not shown), and a proximal end (not shown) adapted to be operated outside the vessel. During use, the proximal end of the scraping device 340 is operated to cause the distal end 341 to scrape embolic debris trapped in a sac or mesh apex toward the distal end of an aspiration tube (not shown) where it can be drawn into the tube and removed from the filter mesh 80.

A method of temporarily filtering and aspirating embolic material from the blood in a blood vessel is also described. The method includes the steps of first providing an insertion device which can be a cannula or introducer or the like, where the insertion device has a distal end adapted to enter an artery and a proximal end adapted to receive a modular filter apparatus. A modular filter apparatus is also provided that has an adjustable filter frame capable of assuming enlarged or contracted conditions, a shaft having a proximal end, a distal end, and a lumen which extends from an opening in the proximal end to an opening in the distal end, and a filter mesh therein having an inner surface. An elongated aspiration tube is provided that has a proximal end, a distal end and a lumen extending from an opening in the proximal end to an opening in the distal end. The proximal end of the tube is adapted to connect to an aspiration source and the distal end is slideably insertable into the proximal end of the filter shaft. The distal end of the insertion device is introduced into a blood vessel. The modular filter apparatus is introduced into the port on the insertion device and is subsequently advanced through the insertion device into the blood vessel. The adjustable filter is then deployed in the vessel. The aspiration tube is slideably inserted through the shaft of the filter until the distal end of the tube lies near the inner surface of the filter mesh. Negative pressure is applied to the proximal end of the aspiration tube and embolic debris is drawn away from the inner surface of the mesh and into the tube. The aspiration tube is then removed from the vessel, embolic debris that was generated having already been removed before the aspiration tube is removed from the shaft. Some embodiments of the method just described include the additional step of re-inserting the aspiration tube into the filter shaft near the inner surface of the mesh after the step of removing the tube from the vessel and repeating the step of aspiration.

Figure 41A:
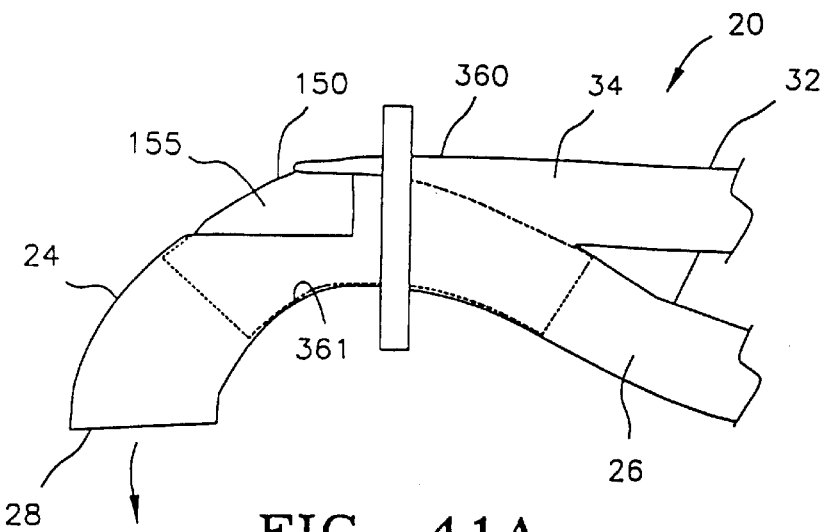
FIG. 41A is a lateral elevation of an embodiment of a cannula with a filter liner.
Figure 41B:
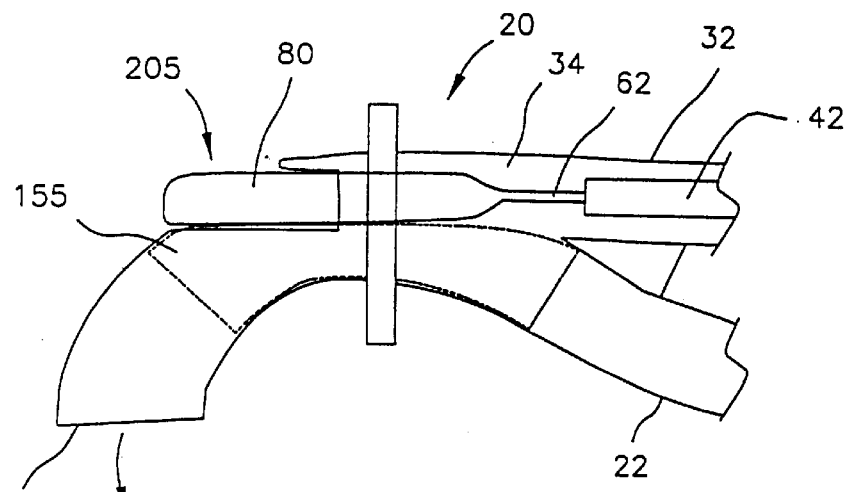
FIGS. 41B–C show the embodiment of FIG. 42A as the liner compresses into the lumen of the cannula to permit passage of the filter device.
Figure 41C:
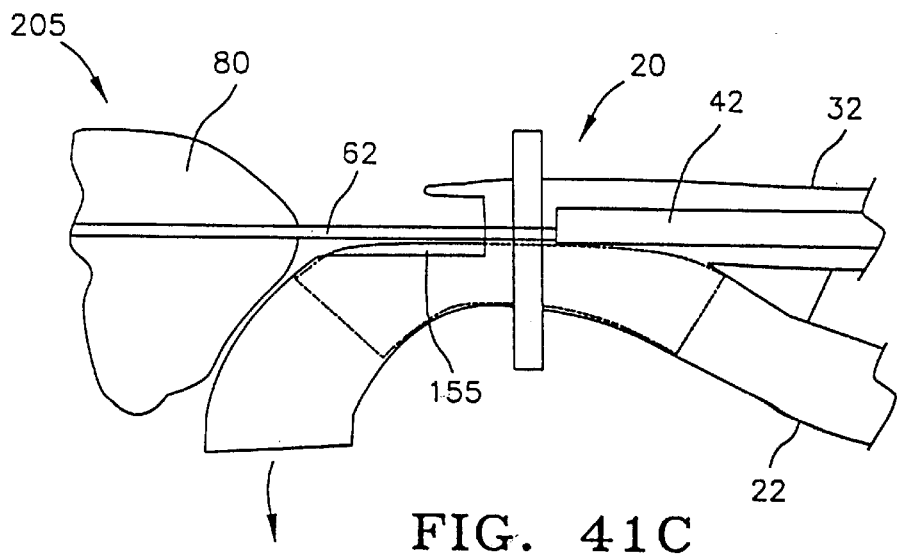

The embodiments of the modular filter apparatus described herein are slideably insertable into an arterial cannula. An embodiment of an arterial cannula capable of receiving a modular filter apparatus for capturing embolic material in a blood vessel is depicted in FIGS. 41A–C. The cannula 20 includes an outer surface 360, an inner surface 361, a curved distal end 24 adapted to enter an artery, a proximal end (not shown) adapted to receive blood from a bypass oxygenator machine, a lumen 26 which extends from the proximal end to an outlet on the distal end and an opening 150 in a region where the distal end of the cannula curves. The cannula 20 of FIGS. 41A–C also includes a port 32 on the outer surface 360 of the cannula for receiving a modular filter apparatus. The port has a proximal opening (not shown) and a passage 34 extending distally from the proximal opening along the cannula to the opening 150 in the distal curved region of the cannula.

Certain embodiments, such as the one shown in FIGS. 41A–C, also include a flexible, blood impermeable cannula liner 155 adapted to conform to the inner surface 361 of the cannula 20 and cover the opening 150 in the distal curved region 24 of the cannula when the cannula is free of the modular filter apparatus. During use, the liner 155 compresses away from the opening 150 in the distal curved region 24 of the cannula as the frame 205 and mesh 80 of the modular filter apparatus are inserted through the port 32 to allow passage of the filter apparatus, but not blood, out the opening 150 in the distal curved region 24 of the cannula 20. FIG. 41A shows the cannula 20 with the liner 155 in position when the cannula is free of the modular filter apparatus. FIG. 41B shows the modular filter apparatus advancing through the opening 150 in the distal region of the cannula and the liner 155 compressing away from the inner surface 361 of the cannula into the lumen 26 of the cannula. FIG. 41C shows the modular mesh 80 of the modular filter apparatus completely advanced through the opening 150 in the cannula and the liner 155 protecting the integrity of the lumen 26 of the cannula thus inhibiting the flow of blood out the opening 150.

Figure 45B:
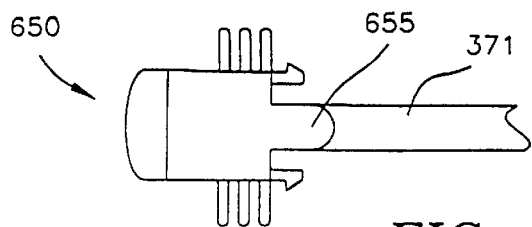
FIGS. 45A–D depict the embodiment of the obturator of FIG. 44.
Figure 45A:
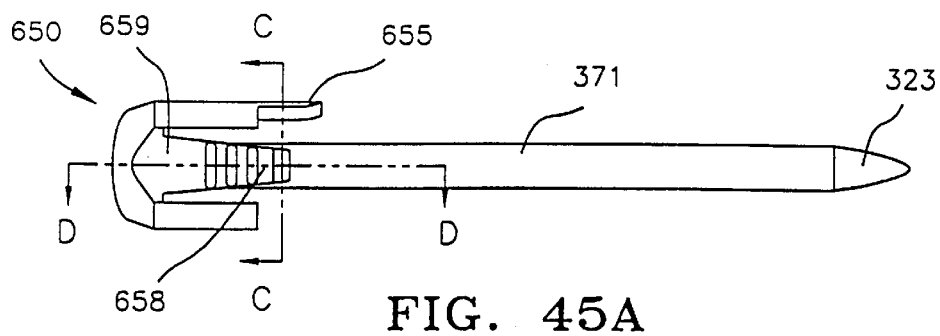
Figure 45C:
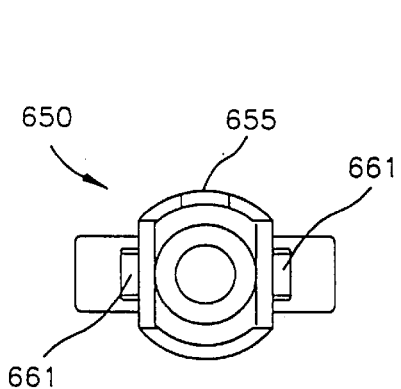
Figure 45D:
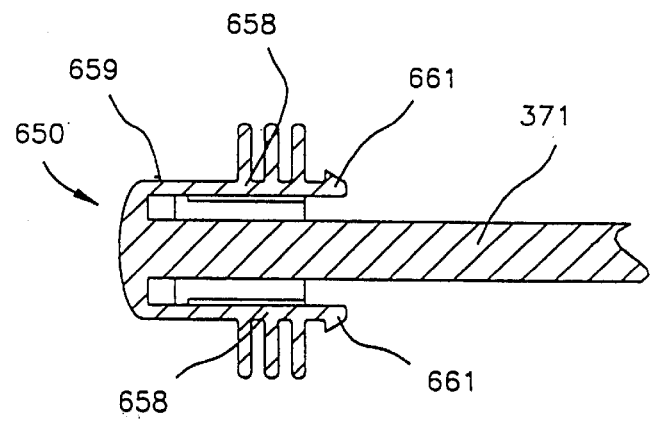
Figure 45E:
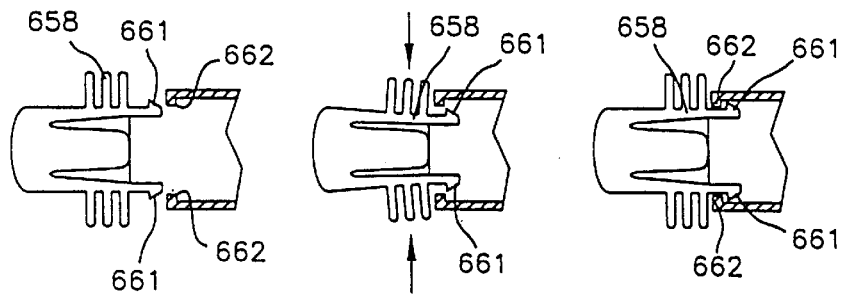
FIG. 45E shows a progression of the engagement of the indexing/locking mechanism of FIGS. 44 and 45.
Figure 46:
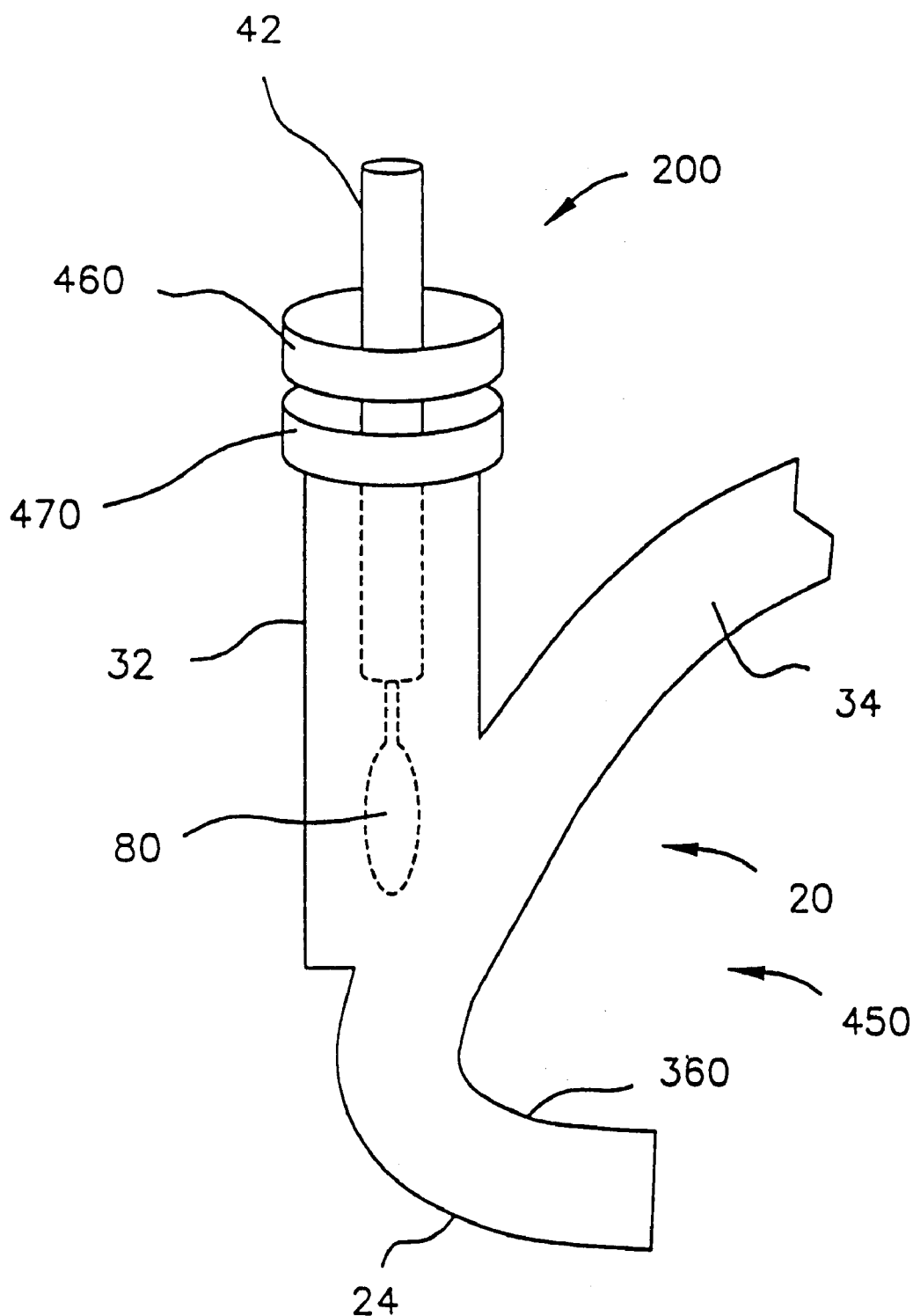
FIG. 46 is an embodiment of a blood filtering system.
Figure 47A:
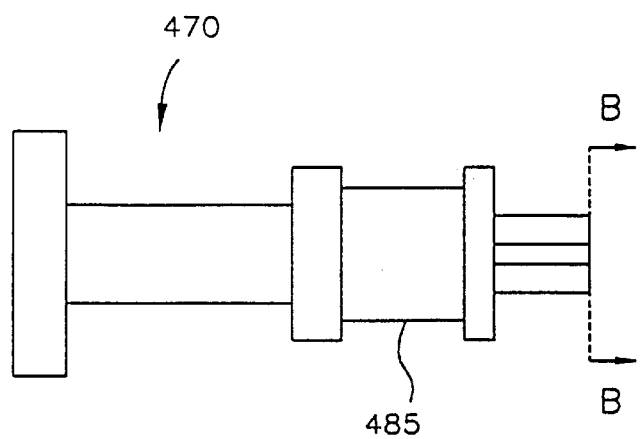
FIGS. 47A–G depicts another embodiment of an indexing/locking mechanism.
Figure 47B:
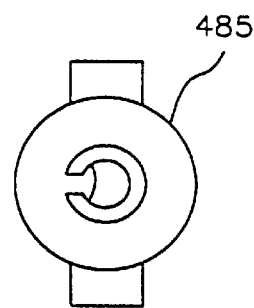
Figure 47D:
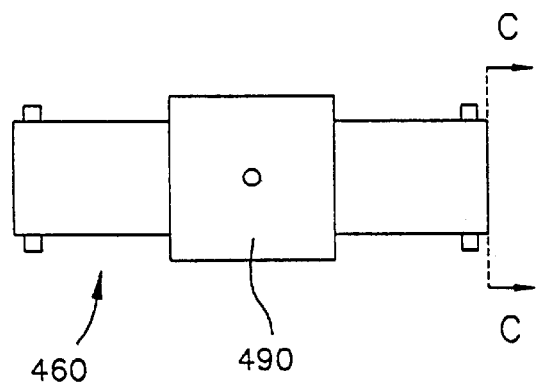
Figure 47C:
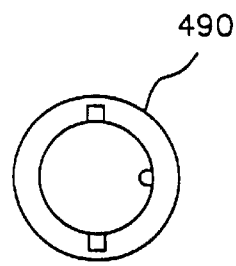
Figure 47G:
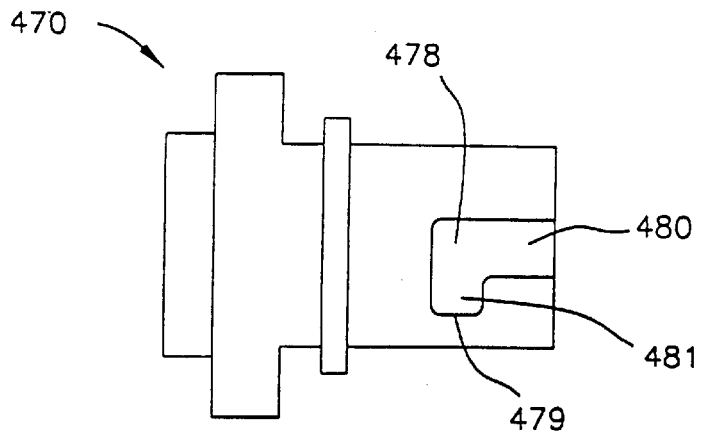
Figure 47E:
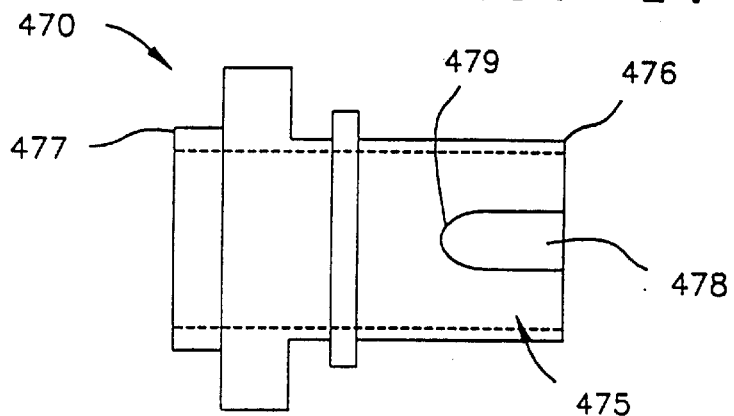
Figure 47F:
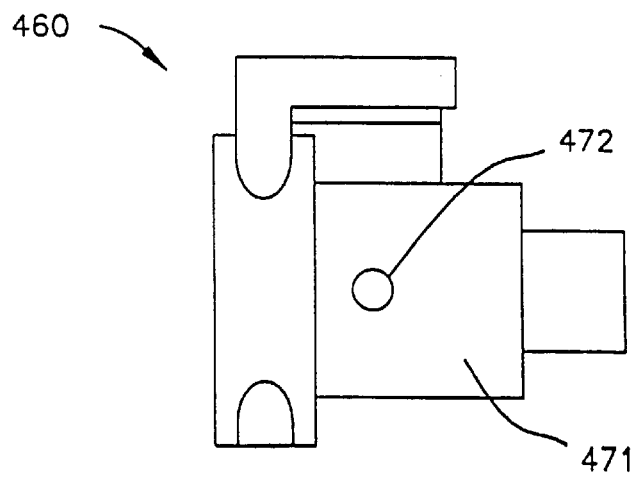

Blood filtering system are also described, and an embodiment is depicted in FIG. 46. The system 450 includes an arterial cannula 20 capable of receiving a modular filter apparatus 200 for capturing embolic material in a blood vessel. The arterial cannula 20 has an outer surface 360, a distal end 24 adapted to enter an artery, a proximal end (not shown) adapted to receive blood from a bypass oxygenator machine, and a lumen 34 which extends from the proximal end to the distal end, and a port 32 for receiving the modular filter apparatus 200. The system 450 also includes a modular filter apparatus 200 for insertion into the port 32 of the arterial cannula 20. The filter apparatus includes (as shown in previous figures) a shaft having a proximal end and a distal end, an adjustable frame disposed about the distal end of the shaft, which is expandable between a contracted condition and an enlarged condition, a frame sizing mechanism associated with the frame, and a filter mesh 80 coupled to the frame for capturing embolic material. The modular filter apparatus 200 is removably insertable into the arterial cannula 20, and, upon insertion through the cannula into the artery the frame sizing mechanism adjusts the diameter of the filter frame to conform to the inner lumen of the vessel. The embodiment of FIG. 45 also includes a filter cartridge 42 having a distal region 460. FIG. 45 also shows a proximal region 470 on the cannula port 32.

Certain embodiments further include various types of indexing and indexing/locking mechanisms to assure that the modular filter apparatus or other modular apparatus such as an obturator, is aligned properly and securely in the insertion device. Typical insertion devices include cannulas, introducers and the like. One embodiment of a blood filtering system with an indexing locking mechanism includes a tubular filter cartridge that is slideably insertable into an insertion device. The cartridge, as described before, is adapted to slideably receive the distal end of the filter shaft and protect the adjustable frame and mesh. The cartridge has a distal region, an outer surface and a guide mechanism coupled to the outer surface of the cartridge in the distal region. One embodiment of this guide mechanism is a guide pin. Another embodiment is a guide tab. The insertion device has a proximal end, a distal end, a proximal region, a circumference and a lumen which extends from an opening in the proximal end to an opening in said distal end. The device further includes a slot in the proximal region adapted to receive the guide mechanism of the cartridge when the cartridge is slideably inserted into the insertion device. This slot can also receive the guide mechanisms of other modular apparati such as obturators and the like. During use, the cartridge or obturator is rotated as it is advanced into the insertion device until the guide device of the cartridge or obturator aligns with and engages slot in the insertion device. The cartridge or obturator is thereby aligned with the insertion device.

Figure 44A:
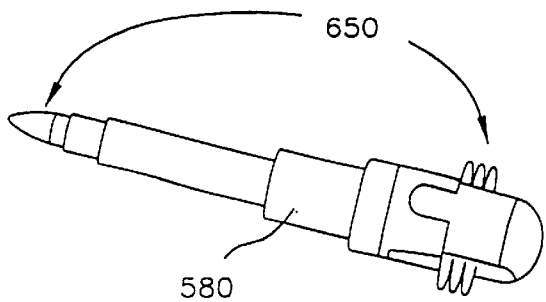
FIGS. 44A–F show an embodiment of an obturator with an indexing/locking mechanism coupled to an introducer.
Figure 44C:
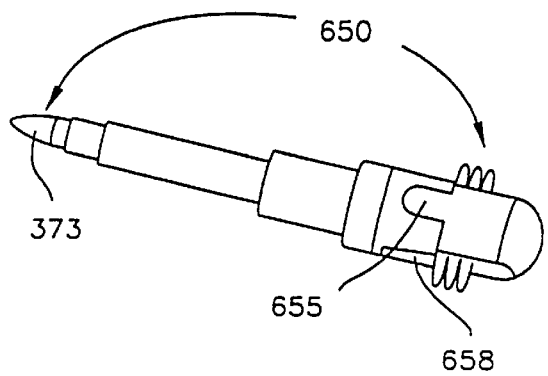
Figure 44B:
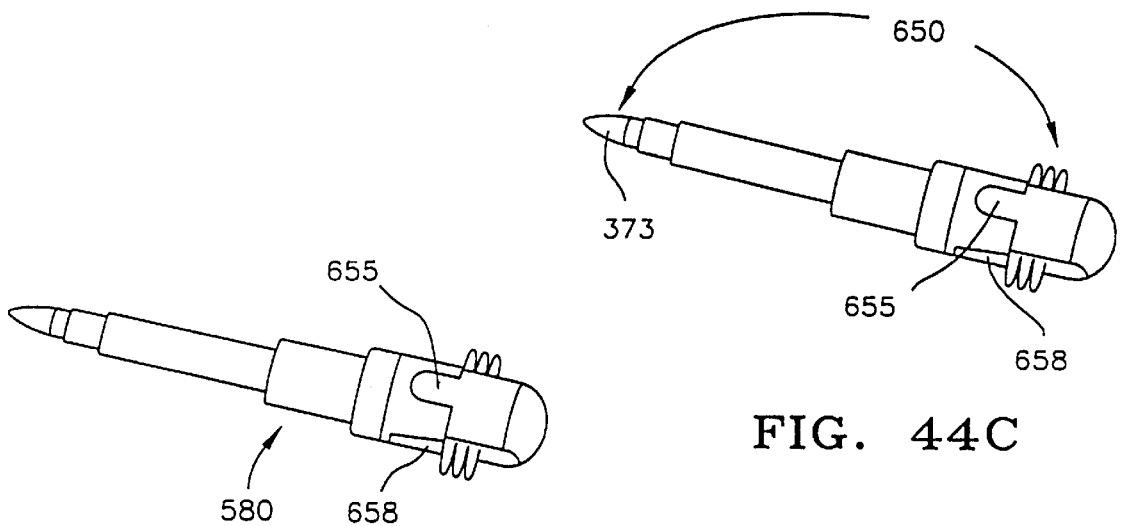
Figure 44D:
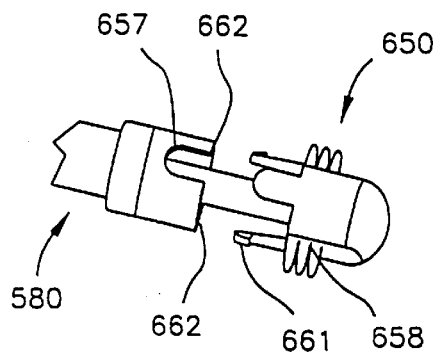
Figure 44E:
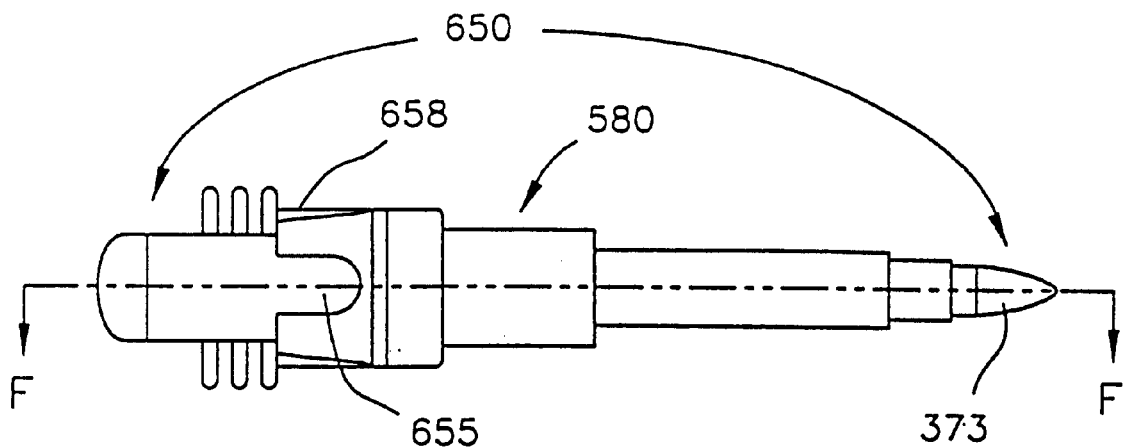
Figure 44F:
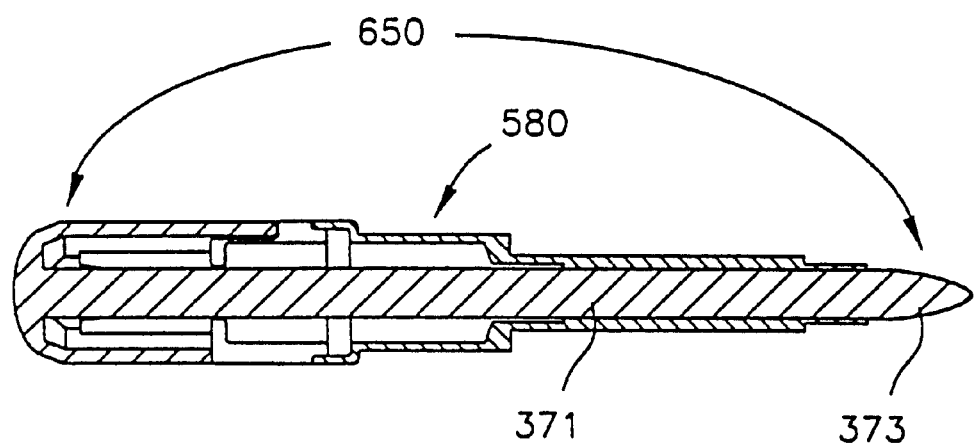
Figure 50:
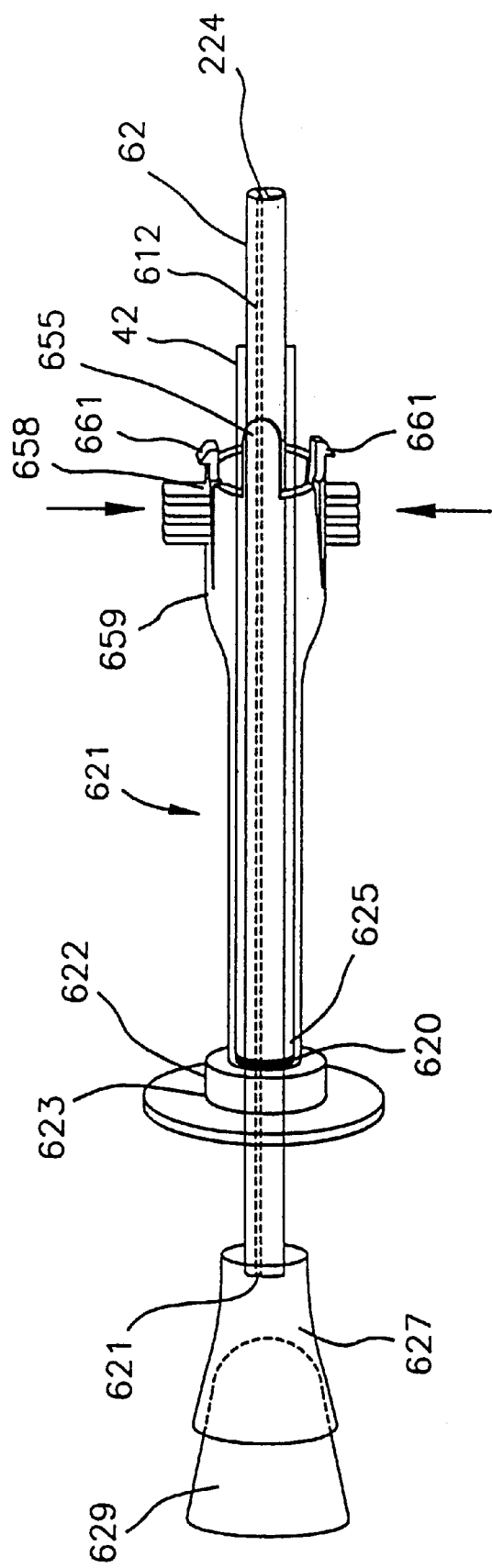
FIG. 50 is a lateral cross-section of the filter cartridge of FIG. 21 showing an embodiment of a vent hole and an indexing/locking mechanism.

FIGS. 44A–F show an embodiment of an indexing mechanism coupled to an introducer 580 and an obturator 650. In this embodiment, the guide mechanism is a guide tab 655 projecting axially and parallel to the outer surface of the obturator. FIG. 50 shows this embodiment of an indexing mechanism coupled to a filter cartridge 42, where the guide tab 655 projects axially and parallel to the outer surface of the cartridge 42. FIG. 44D shows the slot 657 in the indexing mechanism that is coupled to the introducer 580. In other embodiments, the slot is in the proximal region of the side port of a cannula.

Certain embodiments also include a locking mechanism to allow the modular filter apparatus, obturator or other apparatus to be locked into alignment once inserted into the introducer or cannula. These embodiments include an elongated member 658, as seen in FIGS. 44A–F, FIGS. 45A–E and FIG. 50 that has a proximal and a distal end. The proximal end 659 is coupled to the obturator 650 in FIGS. 44A–F and FIGS. 45A–E. In other embodiments, it is coupled to the outer surface of a filter cartridge or cartridge sleeve 621 in FIG. 50. The distal region of the elongated member has a hook 661. The insertion device has a shelf overhanging the opening in the proximal end that is adapted to engage the hook. In FIG. 44D and FIG. 45E, this shelf 662 can be seen overhanging the opening in the proximal end of the introducer 580. During use, the elongated member 658 of the cartridge, cartridge sheath or obturator 650 is operated to slide the hook 661 under the shelf 662 of the introducer 580 or cannula or other insertion device and lock the cartridge or obturator to the device. FIG. 45E shows the progression as the elongated member 658 is depressed and the hook 661 slides under the shelf 662. Once engaged, the elongated member can be operated to disengage the hook from said shelf and unlock the cartridge from the insertion device. The elongated member would once again be depressed allowing the cartridge or obturator to be pulled from the device. In a preferred embodiment, there is a plurality of elongated members and hooks, most preferably two.

Other embodiments of indexing and indexing/locking mechanisms are shown in FIG. 46 and FIGS. 47A–G. FIG. 46 shows an embodiment of a modular filter apparatus 200 that includes a tubular cartridge 42, slideably insertable into the arterial cannula, as described previously. The cartridge 42 has a distal region 460 that is shown in an enlarged view in FIG. 47F. The cartridge distal region 460 has an outer surface 471 and a guide mechanism that is a guide pin 472 coupled to the outer surface of the cartridge in the distal region 460. The guide pin 472 that projects radially from the outer surface 471 of the cartridge. The cannula port 32 (as depicted in previous figures) has a proximal end, a distal end and a proximal region 470 which is shown in an enlarged view in FIG. 47E. This view could also depict the proximal region of an introducer or other insertion device. The proximal region has a circumference and a lumen 475 that extends from an opening in the proximal end 476 to an opening in the distal end 477. The proximal region of the insertion device further includes a slot 478 open at the proximal end 476 and axially extending and terminating 479 at a pre-set length. The slot is adapted to receive the guide pin 472 of the cartridge when the cartridge is slideably inserted into the insertion device. During use, the cartridge 42 is rotated as it is advanced into the insertion device until the guide pin 472 of the cartridge aligns with and engages the open end of the slot 478. The cartridge is then further advanced as the guide pin 472 slides into the slot 478 aligning the cartridge with the insertion device.

In certain embodiments, as shown in FIG. 45G, the slot 478 on the insertion device is L-shaped, having a first region 480 extending axially from the opening at the proximal end and a second region 481 approximately orthogonal to the first region 480 extending partially around the circumference of the device until the second region terminates 479 at a pre-set distance. During use, the cartridge 42 is rotated as it is advanced into the insertion device until the guide pin 472 of the cartridge aligns with and engages the open end of the first region 480 of the slot. The cartridge is then further advanced with rotational pressure until it reaches the second region 481 of the slot and the rotational pressure causes the guide pin to advance to the terminal end 479 of the slot and lock into alignment.

Certain embodiments of the blood filtering system 450 include a BNC (Bayonette Navy Connector) type connector, as depicted in FIGS. 47A–D. This embodiment includes a modular filter apparatus that includes a tubular cartridge, as previously described, slideably insertable into an insertion device. The cartridge has a distal region 460 with a plug section 490 of a BNC coaxial connector coupled to it. The plug section 490 is shown in a lateral view in FIG. 47D and in an end view along line C—C in FIG. 47C. The insertion device has a proximal region 470 with a socket section 485 of a BNC coaxial connector coupled to the proximal region of the port. The socket section is depicted in a lateral view in FIG. 47A and in an end view along line B—B in FIG. 47B. The plug section 490 is adapted to insert into and engage the socket section 485 of the insertion device. During use, the cartridge 42 is rotated and advanced into the insertion device until the BNC plug section 490 of the cartridge engages the BNC socket section 485 of the insertion device, thereby aligning and locking the cartridge into alignment.

Methods of temporarily filtering embolic material from the blood in a blood vessel are also described. One embodiment is a method that includes the steps of providing an insertion device having a distal end adapted to enter an artery and a proximal end adapted to receive a modular filter apparatus. A modular filter apparatus is also provided, where the apparatus has an adjustable filter frame with a filter mesh, a frame sizing mechanism and a shaft having a proximal and a distal end. The adjustable filter frame is capable of being enlarged and contracted. The distal end of the insertion device is introduced into a blood vessel. The modular filter apparatus is then inserted into the device. The adjustable filter is advanced through the device into the blood vessel. Then the frame sizing mechanism is operated to enlarge or contract the adjustable filter frame to conform to the size of the vessel. The adjustable filter is then removed from the vessel, embolic material having been generated and already filtered before the expandable filter is removed from the vessel. In certain embodiments, the insertion device is a cannula and the filter apparatus is inserted through the side port. In other embodiments, the insertion device is an introducer.

In certain embodiments, the method includes the additional step of removing the modular filter apparatus from the insertion device. In other embodiments, the method includes the additional step of inserting a second modular filter into the insertion device after the step of removing the modular filter.

Figure 49A:
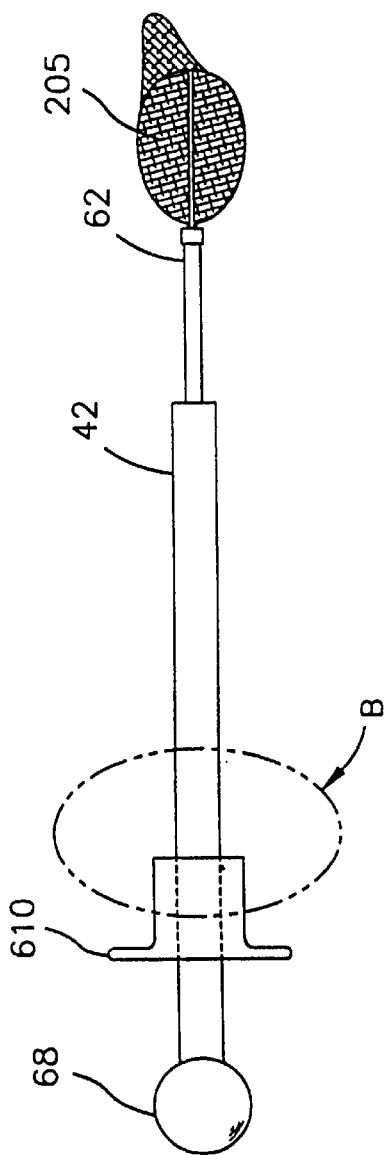
FIG. 49A is a lateral elevation of an embodiment of a filter cartridge with a vent hole.
Figure 49B:
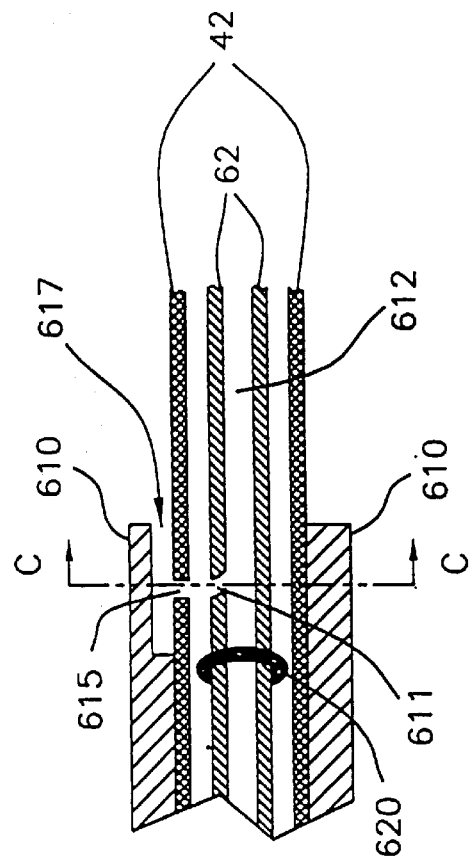
FIG. 49B is an expanded lateral cross-section of area "B" of the embodiment of FIG. 49A showing the vent hole.
Figure 49C:
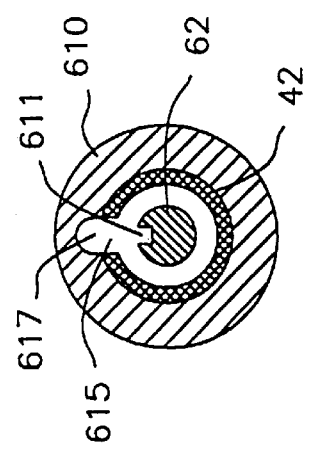
FIG. 49C is a cross-section of the embodiment of FIG. 47B along line C—C.

The embodiment of FIGS. 49A–C is a modular filter apparatus with a vent hole to allow blood and air to escape the apparatus. The filter shaft 62 has a proximal region with an opening 611 and a distal end with an opening (224 of FIG. 21I) and a lumen 612 in fluid communication with the openings. The cartridge 42 has a vent hole 615 in the proximal region. The embodiment of FIGS. 49A–C further includes a cartridge cap 610 that has a lumen running from an opening in the proximal end to an opening in the distal end. The cap 610 is adapted to sealably receive the proximal region of the cartridge 42. The distal opening in the cap has an enlarged region 617 that is not sealed to the cartridge 42 and is aligned over the cartridge vent hole 615. This enlarged region 617 is adapted to permit escape of blood from the vent hole 615. The embodiment of FIGS. 49A–C also includes a seal 620 disposed about the outer surface of the shaft 62 proximal to the opening 611 in the proximal region of the shaft. During use, the opening 611 in the proximal region of the shaft allows blood to escape the shaft lumen 612 and pass through the cartridge vent hole 615 and out the enlarged area 617 in the distal opening of the cartridge cap 610 when the seal 620 is proximal to the cartridge vent hole 615. When the seal 620 is distal to the vent hole 615, no blood escapes through the hole 615. In some embodiments, the seal is an O-ring. In certain embodiments, there is a recessed area surrounding the cartridge vent hole. In these embodiments, blood exits the vent hole with reduced jetting due to its deflection by the recess surrounding the hole, and the blood contacts the enlarged region of the cartridge cap with reduced splashing.

Another venting embodiment is depicted in FIG. 50. This embodiment has a filter shaft 62 with a lumen 612 running between a proximal end having an opening 621 and a distal end having an opening 224. The filter apparatus further includes a cartridge sleeve 621 with a lumen running between a proximal end with an opening and a distal end with an opening. The sleeve 621 is adapted to sealably receive the cartridge 42 with the proximal end 625 of the cartridge lying distal to the proximal region of the sleeve. A seal 620 is disposed about the outer surface of the proximal region of the shaft, proximal to the proximal end 625 of the cartridge 42 and distal to the proximal end 623 of the cartridge sleeve 621. The cartridge sleeve 621 slideably and sealably receives the shaft 62 in the region of the seal 620. The apparatus further includes a shaft cap 627 that has a lumen running between a proximal and a distal opening. The distal opening is adapted to sealably receive the proximal end of the shaft and the proximal opening is adapted to sealably receive a gas-permeable plug 629 which sealably inserts in the proximal end of the shaft cap 627. During use, the opening in the proximal end of the shaft 621 allows fluid to escape the shaft lumen 612 and pass into the shaft cap 627, and the gas-permeable plug 629 allows gas, but not liquid to escape the shaft cap 627. The embodiment of FIG. 50 also shows a shaft that is adapted to receive a demountable frame (not shown).

Figure 42:
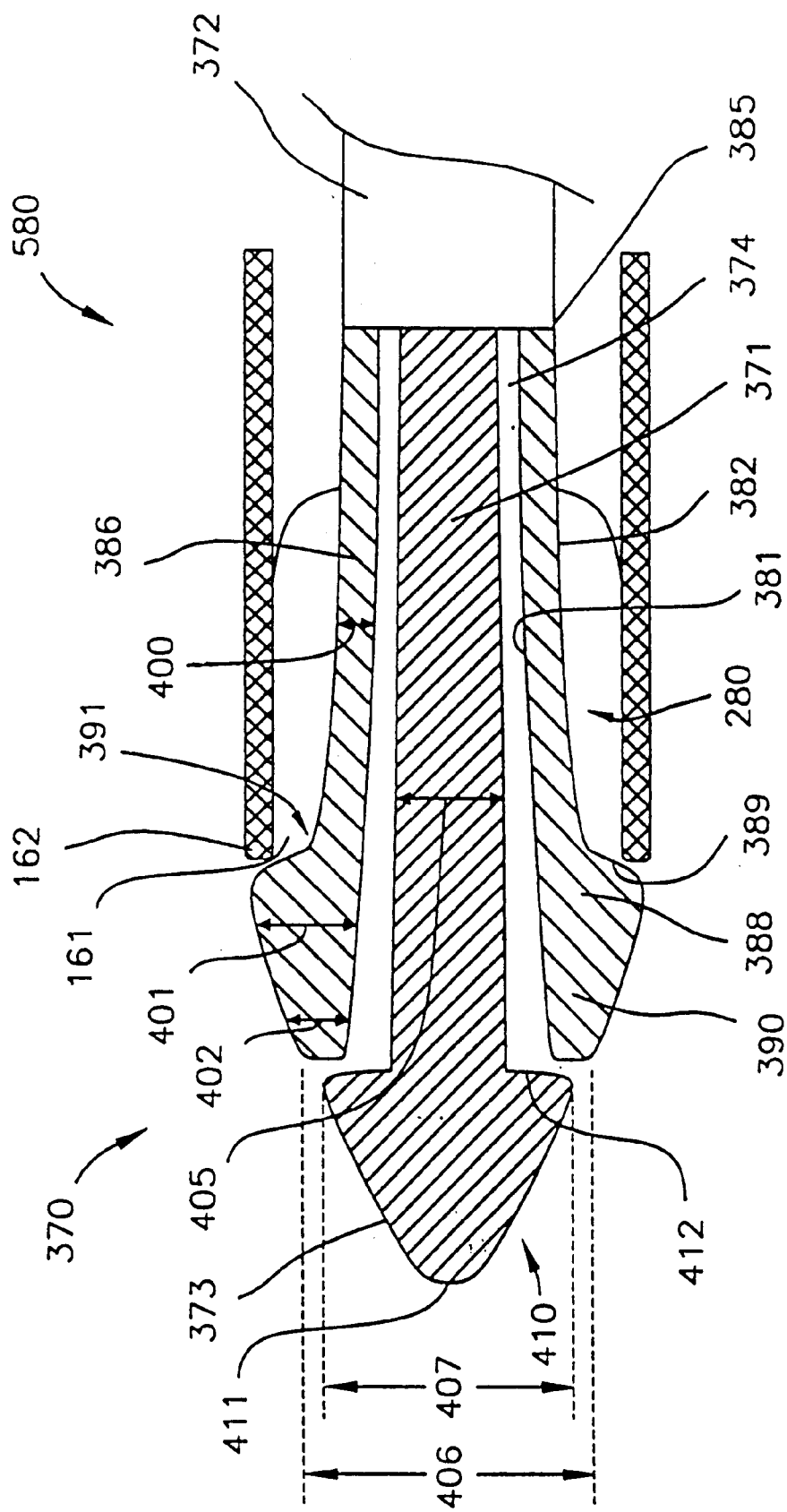
FIG. 42 shows a lateral cross-section of an embodiment of an expanding obturator expanded out of the distal end of an insertion device.

Also described are devices associated with the blood filtering system to assist in its use. Obturators and particularly, expandable obturators, are such devices and may be used to ease the insertion of a cannula or other insertion device into a vessel. FIG. 42 depicts an embodiment of an expandable obturator 370 that is removably insertable through a lumen of a hollow vessel insertion device 580 to reduce trauma as the insertion end 162 of the device enters a vessel. The obturator includes an obturator shaft 371, that has a proximal end (not shown), a tapered distal end 373, a distal region 372 and an outer surface 374. The obturator also includes a plurality of spaced collet segments 380 arranged coaxially around the distal region 372 of the obturator shaft 371. Each segment 380 is expandable between a contracted condition and an expanded condition. The segments each have an inner surface 381 that conforms to the outer surface 374 of the obturator shaft 371, an outer surface 382, a proximal end 385 coupled to the distal region 372 of the obturator shaft 371, an outwardly flaring elongated member 386 that is expandable away from the outer surface 374 of the obturator shaft and has a first thickness 400 between the inner surface and the outer surface. The elongated member 386 forms a collet head 388 at the distal end of the collet segment 380. The collet head 388 has a proximal end 389 and a distal end 390. The proximal end 389 of the collet head 388 gradually thickens to a second thickness 401 that is greater than the first thickness 400 of the elongated member. The gradual thickening of the collet head 388 forms a recess 391 in the region where the elongated member is associated with the collet head. The distal end 390 of the collet head is tapered to a third thickness 402 that is less than the second thickness 401 at the proximal end of the collet head. During use, as the obturator 370 is slideably inserted into the hollow vessel insertion device 580, past the opening in the distal end of the device 161, and the collet segments 380 flare outwardly covering the insertion end 162 of the device as is rests in the recess 391 behind the collet head 388. The distal region of the obturator shaft 373 and the associated collet heads 388 form an overall tapered configuration to ease entry of the device into the vessel.

In the embodiment of FIG. 42, the shaft 371 of the expandable obturator has a first diameter 405, the collet segments collectively have a second diameter 406 at the distal end of the collet heads 388 when the collet segments are in an expanded condition. The obturator shaft further includes a conical tip 410 that extends beyond the distal end of the collet heads, the conical tip 410 having a distal rounded apex 411 and a proximal base 412 where the base has a third diameter 407. The third diameter 407 of the base 412 is greater than the first diameter 405 of the obturator shaft 371, and the third diameter 407 of the base 412 is approximately equal to the second diameter 406 of the collet segments. As a result, the obturator 370 tapers smoothly from the apex of the conical tip 411 to the proximal end 389 of the collet heads 388. There could be 10 or even 20 or more collet segments; however, in a preferred embodiment, there are four collet segments.

Another embodiment of an expandable obturator is depicted in FIGS. 43A–C. This embodiment includes a plurality of spaced head segments 680 arranged coaxially around the distal region of the obturator shaft 371. Each head segment 680 is expandable between a contracted condition and an expanded condition as shown in the progression of FIG. 43A through FIG. 43C as the obturator is advanced through a hollow vessel insertion device 580. Each head segment has an inner surface that conforms to the outer surface of the obturator shaft, an outer surface, a distal end 681 associated with the distal end of the obturator shaft and an outwardly flaring tapered proximal end 682 that is expandable away from the outer surface of the obturator shaft 371. During use, as the obturator is slideably inserted into the hollow vessel insertion device, past an opening in the distal end of the device, the proximal end 682 of the head segments 680 flare outwardly forming an overall tapered configuration to case entry of the device into the vessel.

Another embodiment of an obturator is depicted in FIGS. 44–45. The obturator 650 is slideably insertable into a hollow vessel insertion device, and includes an obturator shaft 371 with a tapered distal end 373. The embodiment of FIGS. 44–45 also includes an embodiment of an indexing locking mechanism as previously described.

A method of introducing an insertion device into a vessel using an expanding obturator to reduce trauma as the device enters the vessel is also disclosed. The method includes the steps of first providing an insertion device having a distal end adapted to enter a vessel and a proximal end adapted to slideably receive an obturator, and a lumen that extends from the proximal end to the distal end. Next, an expandable obturator having an obturator shaft with a tapered distal end, and a plurality of spaced collet segments arranged coaxially around the distal region of the obturator shaft is provided. Each segment is expandable between a contracted condition and an expanded condition, each segment has a proximal end coupled to the distal region of the obturator shaft, an outwardly flaring elongated member that is expandable away from the outer surface of the obturator and a collet head at the distal end of the collet segment. The proximal end of the collet head is gradually thickened to a thickness greater than the thickness of the elongated member, forming a recess in the region where the elongated member is associated with the collet head. The distal end of the collet head is tapered to a thickness less than the thickness at the proximal end of the collet head. When the collet segments are in an expanded condition, the obturator tapers smoothly from the distal tip to the proximal end of the collet head. Next, the obturator is slideably inserted into the proximal end of the insertion device causing the collet segments of the obturator to contract. Then, the obturator is advanced through the lumen of the insertion device until the collet heads of the obturator are advanced just beyond the distal end of the device. At this point, the collet segments flare to an expanded condition and the distal end of the device rests in the recesses formed behind the collet heads. Next, the insertion device and associated obturator are advanced through an incision in the vessel until the distal end of the device enters the vessel. The methods of using the obturator include embodiments where, after the step of advancing the device and the associated obturator into the vessel, the method further includes the steps of pulling the proximal end of the obturator shaft and causing the gradually thickened proximal end of each collet head to slide under the distal end of the device thereby forcing the collet segments into a contracted condition. Then the obturator is slideably removed from the device. The insertion device may be an introducer or a cannula or any other insertion device.

Figures 48A, 48B, 48C:
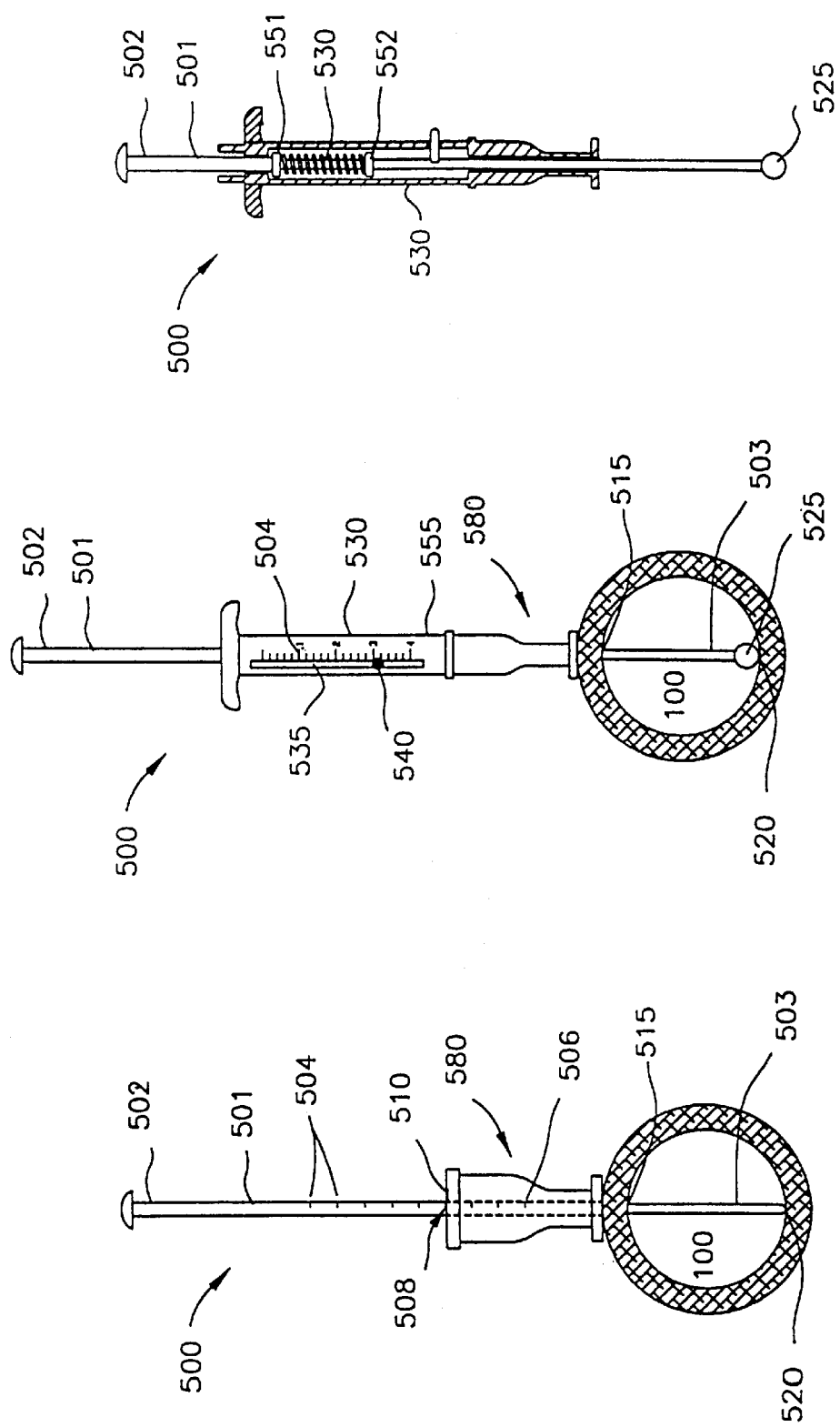
FIG. 48A is a lateral elevation of an embodiment of a vessel sizing tool inserted through an insertion device and into a vessel.
FIG. 48B is a lateral elevation of an embodiment of a vessel sizing tool that includes a vessel sizing cartridge.
FIG. 48C is a lateral cross-section of the embodiment of FIG. 46A.

When adjustable filters are used, it is helpful to know in advance the size of the vessel into which the filters are to be introduced. Embodiments of a tool for sizing a vessel are also disclosed. The tool is used to determine the diameter of a vessel into which an insertion device is inserted. FIGS. 48A–C depicts an embodiment of a vessel sizing tool 500 that includes a vessel sizing shaft 501, slideably insertable into a hollow vessel insertion device 580. The hollow vessel insertion device can be a cannula, an introducer or a hollow needle or the like. The shaft 501 has a proximal end 502, a distal end 503 and a plurality of visible markings 504 along the shaft indicating units of distance. The most distal 506 such visible marking aligns with an indicator 510 at a predetermined distance on the insertion device 580 when the distal end 503 of the shaft has advanced to a region 515 where the insertion device enters the vessel. During use, the vessel sizing tool 500 is inserted into the insertion device 580 and advanced until the distal end has reached the inner wall 520 of the vessel opposite the region where the insertion device enters the vessel, and the visible marking 508 that now align with the indicator 510 on the insertion device 580 denotes the depth of the shaft in the vessel and thus the vessel diameter. In other embodiments, the vessel sizing shaft 501 is inserted directly into an incision in the vessel without the aid of a hollow vessel insertion device.

Some embodiments, as depicted in FIG. 48B, also include a non-traumatic tip at the distal end of the shaft. The embodiment of FIG. 48B also includes a tubular sizing cartridge 530 adapted to slideably receive the distal end of the sizing shaft 503, the cartridge being removably insertable into the insertion device 580 and having an outer surface 555. In some embodiments, the tubular sizing cartridge provides a hemostatic seal between the sizing shaft and the insertion device into which the cartridge is inserted. Certain embodiments also includes an indicator on the cartridge which aligns with a visible marking on the shaft of the sizing tool when the distal end of the shaft has advanced to region where the insertion device enters the vessel. The embodiment of FIG. 48B includes a plurality of visible markings 504 on the cartridge indicating distance and a transparent region 535 where a visible indicator 540 on the sizing shaft 501 can be viewed. During use, the vessel sizing tool 500 is inserted into the insertion device and advanced until the distal end 525 has reached the inner wall 520 of the vessel opposite the region where the insertion device enters the vessel. The visible indicator 540 on the shaft 501 that aligns with the visible markings 504 on the cartridge 530 denotes the depth of the shaft in the vessel and thus the vessel diameter.

Certain embodiments of the vessel sizing tool 500 include a spring 550 expandable between a compressed condition and an expanded condition, such as depicted in FIG. 48C. The spring has two ends, a first end 551 coupled to the vessel sizing shaft 501, and a second end 552 coupled to the sizing cartridge 530. During use, the shaft 501 is advanced into the lumen of the vessel. The spring 550 compresses as pressure is applied to the proximal end 502 of the shaft, until the distal end 525 of the shaft touches the vessel wall opposing the insertion region. After the visible marking aligned with the indicator is noted, the pressure on the proximal end 502 of the shaft 501 is released, the spring 550 expands and the sizing shaft withdraws from the vessel lumen. In a preferred embodiment, the vessel to be sized is an artery. The spring also prevents over insertion of the tool, because when a certain force is reached at the distal tip, for instance, when the tip engages the arterial wall, the spring compresses.

A method of determining the approximate diameter of a vessel is also described. The method includes the steps of first providing a hollow vessel insertion device having a distal end adapted to enter a vessel, a proximal end adapted to receive a vessel sizing tool, a lumen that extends from the proximal end to the distal end and an indicator marking at a predetermined location. Also provided is a vessel sizing tool that includes a shaft that is slideably insertable into the insertion device. The shaft has a proximal end, a distal end and a plurality of visible markings along the shaft indicating units of distance, the most distal such visible marking aligning with the indicator marking on the insertion device when the distal end of the shaft has advanced to a region where the shaft enters the vessel. The distal end of the insertion device is then introduced into the vessel. Next, the distal end of the vessel sizing tool is slideably inserted into the proximal end of the insertion device. Then the vessel sizing tool is advanced into the insertion device until the most distal marking on the tool aligns with the indicator on the insertion device, indicating that the distal end of the tool has just entered the vessel. Next, the tool is advanced until the distal end of the tool engages the vessel wall opposite the incision. It is then noted which visible marking now aligns with the indicator on the insertion device, this visible marking denoting the depth of the tool in the vessel and thus the vessel diameter.

Certain embodiments of the method further include the step of pulling on the proximal end of the vessel sizing tool and slideably removing the tool from the insertion device following the step of noting the depth of the tool in the vessel.

Other embodiments of the method further include the steps of providing a vessel sizing tool that additionally includes a tubular sizing cartridge adapted to slideably receive the distal end of the sizing shaft. The cartridge is removably insertable into the insertion device. The cartridge has a plurality of visible markings indicating distance and a transparent region where a visible marking on the sizing shaft can be viewed and compared to the visible marking on the cartridge. The tool further includes a spring, expandable between a compressed condition and an expanded condition. The spring has two ends, one end coupled to the vessel sizing shaft and the other end coupled to the sizing cartridge. Next, pressure is applied to the proximal end of the vessel sizing shaft thereby advancing the shaft into the lumen of the vessel as the spring compresses until the distal end of the shaft touches the vessel wall opposite the incision. Pressure on the proximal end of the shaft is maintained while noting which visible marking on the sizing cartridge now aligns with the indicator mark on the shaft. Then the pressure on the proximal end of the shaft is released, whereupon the spring expands and the sizing shaft withdraws from the vessel lumen. Certain embodiments of the method further include the step of pulling and slideably removing the vessel sizing tool from the insertion device.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A filter comprising:
   an adjustable frame which is adjustable between a contracted condition and an enlarged condition, the adjustable frame having a diameter and an interior area;
   a frame sizing mechanism associated with the adjustable frame, wherein the adjustable frame automatically self-adjusts to fit the lumen of the vessel; and
   a filter mesh coupled to the adjustable frame for capturing embolic material,
   wherein the filter is removably insertable into a hollow vessel and, upon insertion into the vessel, the frame sizing mechanism adjusts the diameter of the adjustable frame to conform to the inner lumen of the vessel.

2. The filter of claim 1, wherein the adjustable frame has a proximal region and a distal region, the filter further comprising a cantilever beam having a proximal end, a distal end and a cross-section, the distal end of the cantilever beam associated with the distal region of the adjustable frame and the proximal end of the cantilever beam removably mountable on an insertion device.

3. The filter of claim 1, wherein the frame sizing mechanism is self-adjusting upon advancement of the adjustable frame into the lumen of the vessel.

4. The filter of claim 2, wherein the insertion device is a shaft and the proximal region of the adjustable frame is associated with the distal end of the shaft.

5. The filter of claim 2, wherein the proximal region of the adjustable frame is associated with the proximal end of the cantilever beam.

6. The filter of claim 4, wherein the proximal end of the cantilever beam is coupled to the distal end of the shaft.

7. The filter of claim 4, wherein the proximal end of the cantilever beam is slideably insertable into an opening in the distal end of the shaft.

8. The filter of claim 7, wherein the shape of the cross-section of the cantilever beam is selected from the group consisting of oval, rectangular and triangular, the shape conforming to the opening in the distal end of the shaft, and wherein, during use, the shape of the opening in the distal end of the shaft and the shape of the cross-section of the cantilever beam inhibit rotation of the cantilever beam in the lumen of the shaft.

9. The filter of claim 1, wherein the filter mesh has an apex, the filter further comprising a mesh-occluded sac having an inner surface, the mesh-occluded sac coupled to the apex of the filter mesh, and wherein, during use, embolic debris is trapped in the filter mesh-occluded sac.

10. The filter of claim 2, wherein the insertion device is an arterial cannula.

11. The filter of claim 1, wherein the filter is removably mountable on the end of an insertion device.

12. The filter of claim 2, wherein the insertion device is an introducer.

13. A method of temporarily filtering embolic material from the blood in a blood vessel, the method comprising the steps of:
   providing an insertion device having a distal end adapted to receive a filter;
   providing a filter which is removably mountable on the distal end of the insertion device, the filter having an adjustable frame, a frame sizing mechanism, and a filter mesh therein, the adjustable frame capable of being enlarged and contracted;
   mounting the filter on the distal end of the insertion device;
   contracting the filter;
   introducing the distal end of the insertion device having the filter thereon into a vessel; and
   adjusting the frame sizing mechanism to expand the frame to conform to the inner lumen of the vessel.

14. The method of claim 13, wherein following the step of adjusting the frame sizing mechanism to expand the frame, the method further comprises the step of adjusting the frame sizing mechanism to collapse the frame.

15. The method of claim 14, further comprising the step of removing the filter from the vessel, wherein embolic material is trapped in the filter before the filter is removed from the vessel.

16. A method of temporarily filtering embolic material from the blood in a blood vessel, the method comprising the steps of:

provICE an insertion device having a distal end adapted to receive a filter;

providing a filter which is removably mountable on the distal end of the insertion device, the filter having an adjustable frame, a frame sizing mechanism, and a filter mesh therein, the adjustable frame biased to assume an expanded condition and capable of being contracted;

mounting the filter on the distal end of the insertion device;

adjusting the frame sizing mechanism to contract the filter;

introducing the distal end of the insertion device having the filter thereon into a vessel; and allowing the frame to expand to conform to the inner lumen of the vessel.

17. The method of claim 16, wherein following the step of allowing the frame to expand, the method further comprises the step of adjusting the frame sizing mechanism to collapse the frame.

18. The method of claim 17, further comprising the step of removing the filter from the vessel, wherein embolic material is trapped in the filter before the filter is removed from the vessel.

* * * * *